US011566064B2

United States Patent
Manceur et al.

(10) Patent No.: US 11,566,064 B2
(45) Date of Patent: Jan. 31, 2023

(54) HEMAGGLUTININ-SPECIFIC ANTIBODIES AND USES THEREOF

(71) Applicant: National Research Council of Canada, Ottawa (CA)

(72) Inventors: Aziza Manceur, Montreal (CA); Anne Marcil, Pierrefonds (CA); Wei Zou, Ottawa (CA); Amine Kamen, Montreal (CA); Christine Gadoury, Montreal (CA)

(73) Assignee: National Research Council of Canada, Ottawa (CA)

( * ) Notice: Subject to any disclaimer, the term of this patent is extended or adjusted under 35 U.S.C. 154(b) by 194 days.

(21) Appl. No.: 16/480,727

(22) PCT Filed: Jan. 26, 2018

(86) PCT No.: PCT/IB2018/050493
§ 371 (c)(1),
(2) Date: Jul. 25, 2019

(87) PCT Pub. No.: WO2018/138681
PCT Pub. Date: Aug. 2, 2018

(65) Prior Publication Data
US 2019/0352376 A1 Nov. 21, 2019
US 2020/0331988 A9 Oct. 22, 2020

Related U.S. Application Data

(60) Provisional application No. 62/451,230, filed on Jan. 27, 2017.

(51) Int. Cl.
*A61P 31/16* (2006.01)
*C07K 16/10* (2006.01)
*G01N 33/569* (2006.01)
*A61K 39/00* (2006.01)

(52) U.S. Cl.
CPC .......... *C07K 16/1018* (2013.01); *A61P 31/16* (2018.01); *G01N 33/56983* (2013.01); *A61K 2039/505* (2013.01); *C07K 2317/76* (2013.01); *C07K 2317/92* (2013.01); *G01N 2333/11* (2013.01)

(58) Field of Classification Search
None
See application file for complete search history.

(56) References Cited

U.S. PATENT DOCUMENTS

2010/0074916 A1\* 3/2010 Nabel .................. C07K 14/005
424/189.1

FOREIGN PATENT DOCUMENTS

| WO | WO 1995/004069 A1 | 2/1995 |
| WO | WO 2003/046560 A2 | 6/2003 |
| WO | WO 2004/076670 A1 | 9/2004 |
| WO | WO 2008/028946 A1 | 3/2008 |
| WO | WO 2013/007770 A1 | 1/2013 |
| WO | WO 2013/011347 A1 | 1/2013 |

OTHER PUBLICATIONS

Manceur et al. at the Jun. 12-17, 2016 Conference Program on Vaccine Technology VI at the Grande Real Santa Eulalia Hotel in Albufeira, Portugal, Titled: Pan-HA antibodies for influenza detection and quantification.\*
PCT/IB2018/050493, Apr. 16, 2018, International Search Report and Written Opinion.
PCT/IB2018/050493, Aug. 8, 2019, International Preliminary Report on Patentability.
Chothia et al., Canonical structures for the hypervariable regions of immunoglobulins. J Mol Biol. 1987;196(4):901-917. doi:10.1016/0022-2836(87)90412-8.
Chun et al., Universal antibodies and their applications to the quantitative determination of virtually all subtypes of the influenza A viral hemagglutinins. Vaccine. 2008;26(48):6068-6076. doi:10.1016/j.vaccine.2008.09.015.
Corti et al., A neutralizing antibody selected from plasma cells that binds to group 1 and group 2 influenza A hemagglutinins. Science. 2011;333(6044):850-856. doi:10.1126/science.1205669.
De Kruif et al., Leucine zipper dimerized bivalent and bispecific scFv antibodies from a semi-synthetic antibody phage display library. J Biol Chem. 1996;271(13):7630-7634. doi:10.1074/jbc.271.13.7630.
Dreyfus et al., Highly conserved protective epitopes on influenza B viruses. Science. 2012;337(6100):1343-1348. doi:10.1126/science.1222908.
Eisenberg et al., Analysis of membrane and surface protein sequences with the hydrophobic moment plot. J Mol Biol. 1984;179(1):125-142. doi:10.1016/0022-2836(84)90309-7.
Ekiert et al., A highly conserved neutralizing epitope on group 2 influenza A viruses. Science. 2011;333(6044):843-850. doi:10.1126/science.1204839.
Fenner et al., Rapid and Reliable Diagnostic Algorithm for Detection of Clostridium difficile. J Clin Microbiol. Jan. 2008;46(1):328-30. doi: 10.1128/JCM.01503-07.
Gonzales et al., Minimizing the immunogenicity of antibodies for clinical application. Tumour Biol. 2005;26(1):31-43. doi:10.1159/000084184.
Hashem et al., Universal antibodies against the highly conserved influenza fusion peptide cross-neutralize several subtypes of influenza A virus. Biochem Biophys Res Commun. 2010;403(2):247-251. doi:10.1016/j.bbrc.2010.11.030.
Jones et al., Replacing the complementarity-determining regions in a human antibody with those from a mouse. Nature. 1986;321(6069):522-525. doi:10.1038/321522a0.

(Continued)

*Primary Examiner* — Benjamin P Blumel
(74) *Attorney, Agent, or Firm* — Wolf, Greenfield & Sacks, P.C.

(57) ABSTRACT

The present invention relates to hemagglutinin-specific antibodies, fragments thereof, and uses thereof. More specifically, these antibodies and fragments thereof are able to recognize antigen from multiple influenza strains.

19 Claims, 17 Drawing Sheets

Specification includes a Sequence Listing.

(56) References Cited

OTHER PUBLICATIONS

Kabat et al., Identical V region amino acid sequences and segments of sequences in antibodies of different specificities. Relative contributions of VH and VL genes, minigenes, and complementarity-determining regions to binding of antibody-combining sites. J Immunol. 1991;147(5):1709-1719.

Kang et al., Novel vaccines against influenza viruses. Virus Res. 2011;162(1-2):31-38. doi:10.1016/j.virusres.2011.09.037.

Lefranc et al., IMGT unique numbering for immunoglobulin and T cell receptor variable domains and Ig superfamily V-like domains. Dev Comp Immunol. 2003;27(1):55-77. doi:10.1016/s0145-305x(02)00039-3.

Li et al., A simple slot blot for the detection of virtually all subtypes of the influenza A viral hemagglutinins using universal antibodies targeting the fusion peptide. Nat Protoc. 2010;5(1):14-19. doi:10.1038/nprot.2009.200.

Li et al., Pandemic H1N1 influenza vaccine induces a recall response in humans that favors broadly cross-reactive memory B cells. Proc Natl Acad Sci U S A. 2012;109(23):9047-9052. doi:10.1073/pnas.1118979109.

Merritt et al., AB5 toxins. Curr Opin Struct Biol. 1995;5(2):165-171. doi:10.1016/0959-440x(95)80071-9.

Musher et al., Detection of Clostridium difficile Toxin: Comparison of Enzyme Immunoassay Results with Results Obtained by Cytotoxicity Assay. J Clin Microbiol. Aug. 2007; 45(8): 2737-2739. EPub Jun. 13, 2007. doi: 10.1128/JCM.00686-07.

Nicaise et al., Affinity transfer by CDR grafting on a nonimmunoglobulin scaffold. Protein Sci. Jul. 2004; 13(7): 1882-1891. doi: 10.1110/ps.03540504.

Nielsen et al. Targeting of bivalent anti-ErbB2 diabody antibody fragments to tumor cells is independent of the intrinsic antibody affinity. Cancer Res. 2000;60(22):6434-6440.

Okuno et al., A common neutralizing epitope conserved between the hemagglutinins of influenza A virus H1 and H2 strains. J Virol. 1993;67(5):2552-2558. doi:10.1128/JVI.67.5.2552-2558.1993.

Padlan et al., A possible procedure for reducing the immunogenicity of antibody variable domains while preserving their ligand-binding properties. Mol Immunol. 1991;28(4-5):489-498. doi:10.1016/0161-5890(91)90163-e.

Planche et al., Diagnosis of Clostridium difficile infection by toxin detection kits: a systematic review. Lancet Infect Dis. 2008;8(12):777-784. doi:10.1016/S1473-3099(08)70233-0.

Queen et al., A humanized antibody that binds to the interleukin 2 receptor. Proc Natl Acad Sci U S A. Dec. 1989; 86(24): 10029-10033. doi: 10.1073/pnas.86.24.10029.

Riechmann et al., Reshaping human antibodies for therapy. Nature. 1988;332(6162):323-327. doi:10.1038/332323a0.

Ridgway et al., 'Knobs-into-holes' engineering of antibody CH3 domains for heavy chain heterodimerization. Protein Eng. 1996;9(7):617-621. doi:10.1093/protein/9.7.617.

Rüssmann et al., Evaluation of three rapid assays for detection of Clostridium difficile toxin A and toxin B in stool specimens. Eur J Clin Microbiol Infect Dis. 2007;26(2):115-119. doi:10.1007/s10096-006-0251-7.

Sloan et al., Comparison of real-time PCR for detection of the tcdC gene with four toxin immunoassays and culture in diagnosis of Clostridium difficile infection. J Clin Microbiol. 2008;46(6):1996-2001. doi:10.1128/JCM.00032-08.

Sui et al., Structural and functional bases for broad-spectrum neutralization of avian and human influenza A viruses. Nat Struct Mol Biol. 2009;16(3):265-273. doi:10.1038/nsmb.1566.

Tempest et al., Reshaping a human monoclonal antibody to inhibit human respiratory syncytial virus infection in vivo. Biotechnology (N Y). 1991;9(3):266-271. doi:10.1038/nbt0391-266.

Throsby et al., Heterosubtypic neutralizing monoclonal antibodies cross-protective against H5N1 and H1N1 recovered from human IgM+ memory B cells. PLoS One. 2008;3(12):e3942. doi:10.1371/journal.pone.0003942.

Tsurushita et al., Design of humanized antibodies: from anti-Tac to Zenapax. Methods. 2005;36(1):69-83. doi:10.1016/j.ymeth.2005.01.007.

Turgeon et al., Six rapid tests for direct detection of Clostridium difficile and its toxins in fecal samples compared with the fibroblast cytotoxicity assay. J Clin Microbiol. 2003;41(2):667-670. doi:10.1128/jcm.41.2.667-670.2003.

Yoshida et al., Cross-protective potential of a novel monoclonal antibody directed against antigenic site B of the hemagglutinin of influenza A viruses. PLoS Pathog. 2009;5(3):e1000350. doi:10.1371/journal.ppat.1000350.

Zhu et al., COMBODY: one-domain antibody multimer with improved avidity. Immunol Cell Biol. 2010;88(6):667-675. doi:10.1038/icb.2010.21.

Manceur et al., Generation of monoclonal pan-hemagglutinin antibodies for the quantification of multiple strains of influenza. PLoS One. Jun. 29, 2017;12(6):e0180314. doi:10.1371/journal.pone.0180314. 18 pages.

* cited by examiner

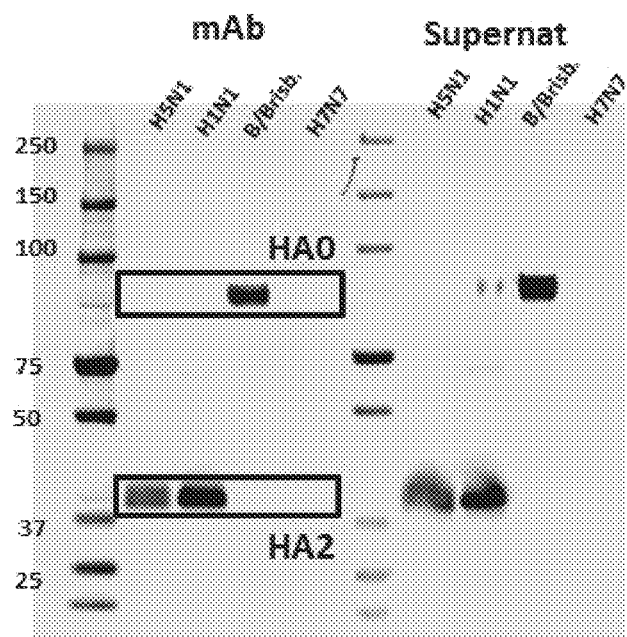
FIGURE 5A (11H12)
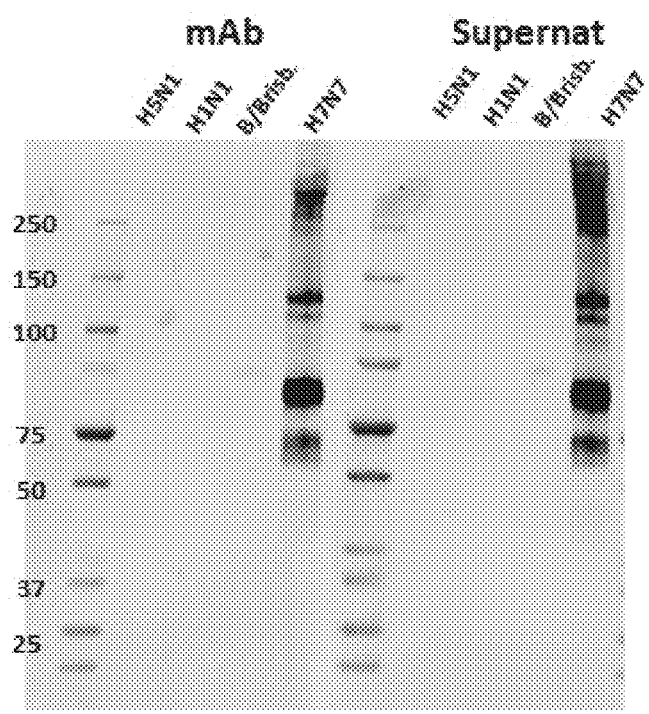
FIGURE 5B (10A9)

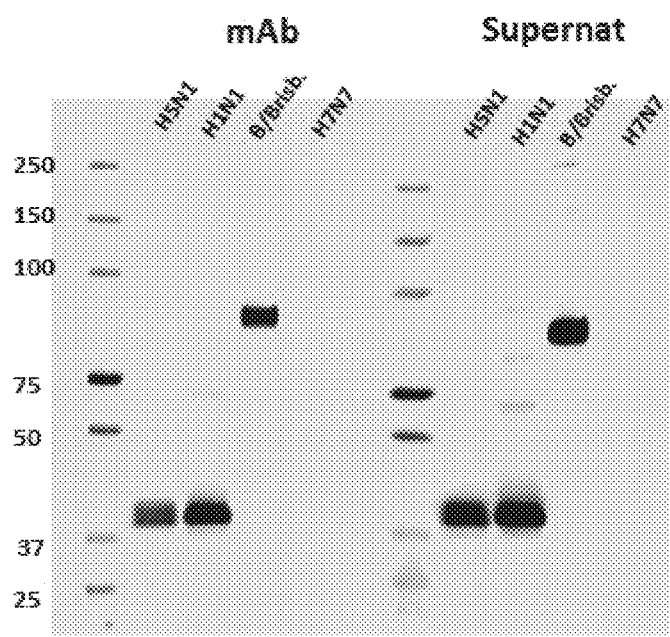
FIGURE 5C (9D1)
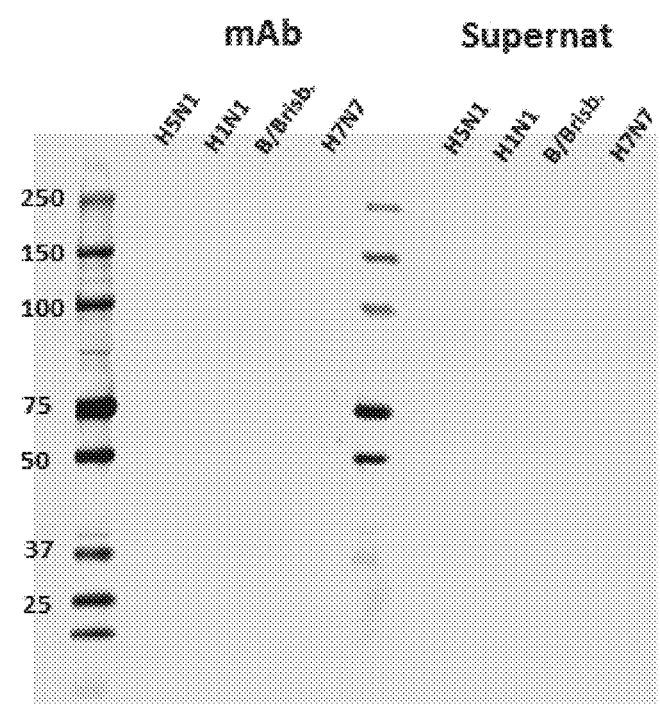
FIGURE 5D (anti-GFP)

(9D1)　　　　　(10A9)　　　　 (11H12)

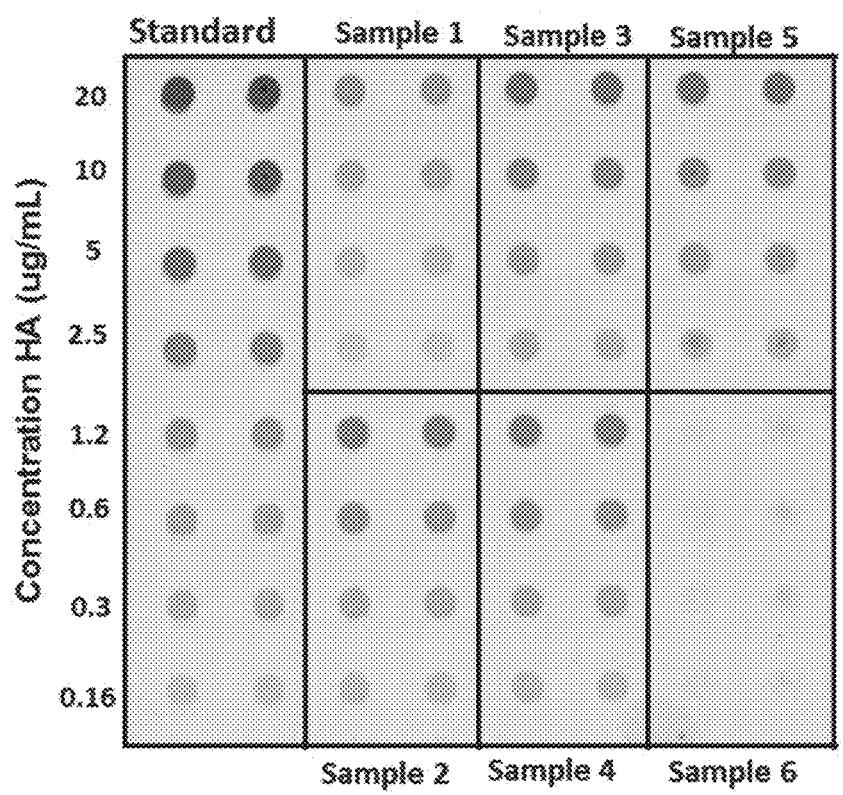
FIGURE 9A
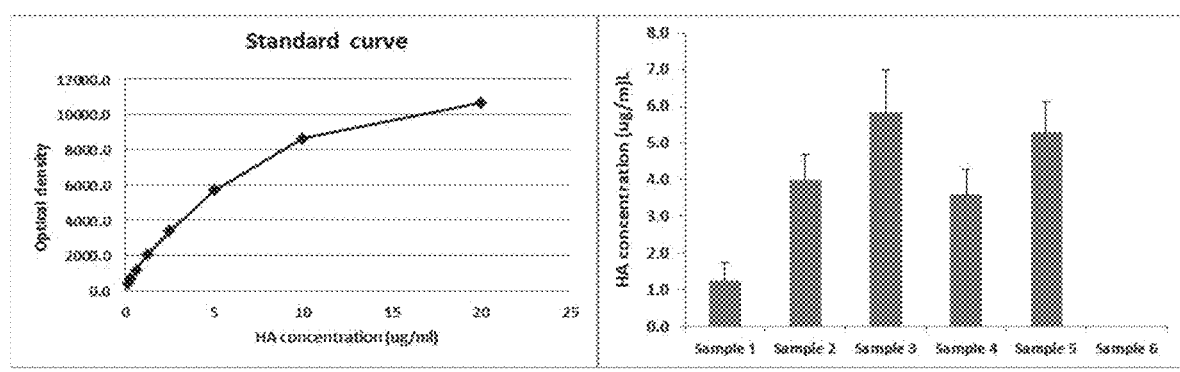
FIGURE 9B
FIGURE 9C

F211-11H12-2 sequence coverage: heavy chain (SEQ ID NO. 29) and light chain (SEQ ID NO.30)

Matched peptides shown in *bold red*.

```
      Signal sequence
  1 | RMKVLSLLYL  LTAIPGFLS|Q  VQLQESGPGL  VKPSQSLSLT  CSVTGYSITS
 51   DYYWNWIRQF  PGNKLEWMAY  IGYDGTNNYN  PSLKNRISIT  RDTSKNQFFL
101   KMSVTTDDT   ATYYCTRDRA  NHDDYFDYWG  QGTTLTVSSA  KTTAPSVYPL
151   APVCGDTTGS  SVTLGCLVKG  YFPEPVTLTW  NSGSLSSGVH  TFPAVLQSDL
201   YTLSSSVTVT  SSTWPSQSIT  CNVAHPASST  KVDKKIEPRG  PTIKPCPPCK
251   CPAPNLLGGP  SVFIFPPKIK  DVLMISLSPI  VTCVVVDVSE  DDPDVQISWF
301   VNNVEVHTAQ  TQTHREDYNS  TLRVVSALPI  QHQDWMSGKE  FKCKVNNKDL
351   PAPIERTISK  PKGSVRAPQV  YVLPPPEEEM  TKKQVTLTCM  VTDFMPEDIY
401   VEWTNNGKTE  LNYKNTEPVL  DSDGSYFMYS  KLRVEKKNWV  ERNSYSCSVV
451   HEGLHNHHTT  KSFSRTPGK
```

```
      Signal sequence
  1 | VLMLLLLWVS  GTC|DIVMSQ  SPSSLAVSVG  EKVTMSCKSS  QSLLNSRNQK
 51   NHLAWYQQKP  GQSPKLLIYW  ASTRESGVPD  RFTGSGSGTD  FTLTISSVKA
101   EDLAVYYCQQ  YYTYRTFGGG  TKLEIKRADA  APTVSIFPPS  SEQLTSGGAS
151   VVCFLNNFYP  KDINVKWKID  GSERQNGVLN  SWTDQDSKDS  TYSMSSTLTL
201   TKDEYERHNS  YTCEATHKTS  TSPIVKSFNR  NEC
```

FIGURE 13A

F211-10A9-2 sequence coverage: heavy chain (SEQ ID NO. 31) and light chain (SEQ ID NO.32)

```
Signal sequence
  1 AGVHQIQLQ  QSGPELVKPG  APVKISCKAS  GYTFTDYYIH  WVRQRPGQGL
 51 EWIGTIYPGN  GHTVTNQKFK  VRATLTADNF  SSTAYLQLNS  LTSEDSGVYF
101 CAYDLFNYWG  QGTLVTVSAA  KTTAPSVYPL  APVCGDTTGS  SVTLGCLVKG
151 YFPEPVTLTW  NSGSLSSGVH  TFPAVLQSDL  YTLSSSVTVT  SSTWPSQSIT
201 CNVAHPASST  KVDKKIEPRG  PTIKPCPPCK  CPAPNLLGGP  SVFIFPPKIK
251 DVLMISLSPI  VTCVVVDVSE  DDPDVQISWF  VNNVEVHTAQ  TQTHREDYNS
301 TLRVVSALPI  QHQDWMSGKE  FKCKVNNKDL  PAPIERTISK  PKGSVRAPQV
351 YVLPPPEEEM  TKKQVTLTCM  VTDFMPEDIY  VEWTNNGKTE  LNYKNTEPVL
401 DSDGSYFMYS  KLRVEKKNWV  ERNSYSCSVV  HEGLHNHHTT  KSFSRTPGK
```

```
Signal sequence
  1 VSGACDIVM   TQSPSSLAMS  VGQKVTMSCK  SSQSLLNSDT  QKNFLANYQQ
 51 KPGQSPKILV  YFASTRESGV  PDRFIGSGSG  TDFTLTITSV  QAEDLADYFC
101 QQYYSIPLTT  GAGTKLELKR  ADAAPTVSIF  PPSSEQLTSG  GASVVCFLNN
151 FYPKDINVKW  KIDGSERQNG  VLNSWTDQDS  KDSTYSMSST  LTLTKDEYER
201 HNSYTCEATH  KTSTSPIVKS  FNRNEC
```

FIGURE 13B

F211-9D1-2 sequence coverage: heavy chain (SEQ ID NO. 33) and light chain (SEQ ID NO.34)

```
      Signal sequence
  1 |RMKVLSLLYL LTAIPGFL|D VQLQESGPGL VKPSQSLSLT CSVTGYSITS
 51  DYYWNWIRQF PGNKLEWMAY IGYDGSNYN  PSLKNRISIT RDTSKNQFFL
101  KLNSVTTEDT ATYYCTRDRA HDDYFDYWG  QGTTLTVSSA KTTAPSVYPL
151  APVCGDTTGS SVTLGCLVKG YFPEPVTLTW NSGSLSSGVH TFPAVLQSDL
201  YTLSSSVTVT SSTWPSQSIT CNVAHPASST KVDKKIEPRG PTIKPCPPCK
251  CPAPNLLGGP SVFIFPPKIK DVLMISLSPI VTCVVVDVSE DDPDVQISWF
301  VNNVEVHTAQ TQTHREDYNS TLRVVSALPI QHQDWMSGKE FKCKVNNKDL
351  PAPIERTISK PKGSVRAPQV YVLPPPEEEM TKKQVTLTCM VTDFMPEDIY
401  VEWTNNGKTE LNYKNTEPVL DSDGSYFMYS KLRVEKKNWV ERNSYSCSVV
451  HEGLHNHHTT KSFSRTPGK
```

```
      Signal sequence
  1 |VLMLLLLWVS GTCG|DIVMSQ SPSSLAVSVG EKVTMSCKSS QSLLNSRNQK
 51  NYLAWYQQKP GQSPKLLIYW ASTRESGVPD RFSGSGSGTD FTLTISSVKA
101  EDLAVYYCQQ YYSYRTFGGG TKLEIKRADA APTVSIFPPS SEQLTSGGAS
151  VVCFLNNFYP KDINVKWKID GSERQNGVLN SWTDQDSKDS TYSMSSTLTL
201  TKDEYERHNS YTCEATHKTS TSPIVKSFNR NEC
```

FIGURE 13C

10A9 full protein sequence

METDTLLLWVLLLWVPGSTGQIQLQQSGPELVKPGAPVKISCKASGYTFTDYYIHWVNQR
PGQGLEWIGYIYPGNGHTVYNQKFKVRATLTADNPSSTAYLQLNSLTSEDSGVYFCAYDL
FNYWGQGTLVTVSAAKTTAPSVYPLAPVCGDTTGSSVTLGCLVKGYFPEPVTLTWNSGSL
SSGVHTFPAVLQSDLYTLSSSVTVTSSTWPSQSITCNVAHPASSTKVDKKIEPRGPTIKP
CPPCKCPAPNLLGGPSVFIFPPKIKDVLMISLSPIVTCVVVDVSEDDPDVQISWFVNNVE
VHTAQTQTHREDYNSTLRVVSALPIQHDWMSGKEFKCKVNNKDLPAPIERTISKPKGSV
RAPQVYVLPPPEEEMTKKQVTLTCMVTDFMPEDIYVEWTNNGKTELNYKNTEPVLDSDGS
YFMYSKLRVEKKNWVERNSYSCSVVHEGLHNHHTTKSFSRTPGRKRRAPVKQTLNFDLLK
LAGDVESNPGPMETDTLLLWVLLLWVPGSTGDIVMTQSPSSLAMSVGQKVTMSCKSSQSL
LNSDTQKNFLAWYQQKPGQSPKILVYFASTKESGVPDRFIGSGSGTDFTLTITSVQAEDL
ADYFCQQYYSIPLTFGAGTKLELKRADAAPTVSIFPPSSEQLTSGGASVVCFLNNFYPKD
INVKWKIDGSERQNGVLNSWTDQDSKDSTYSMSSTLTLTKDEYERHNSYTCEATHKTSTS
PIVKSFNRNEC*

FIGURE 14A

11H12 full protein sequence

METDTLLLWVLLLWVPGSTGDVQLQESGPGLVKPSQSLSLTCSVTGYSITSDYYWNWIRQ
FPGNKLEWMAYIGYDGTKNYNPSLKNRISITRDTSKNQFFLKLNSVTTDDTATYYCTRDR
ANWDDYFDYWGQGTTLTVSSAKTTAPSVYPLAPVCGDTTGSSVTLGCLVKGYFPEPVTLT
WNSGSLSSGVHTFPAVLQSDLYTLSSSVTVTSSTWPSQSITCNVAHPASSTKVDKKIEPR
GPTIKPCPPCKCPAPNLLGGPSVFIFPPKIKDVLMISLSPIVTCVVVDVSEDDPDVQISW
FVNNVEVHTAQTQTHREDYNSTLRVVSALPIQHDWMSGKEFKCKVNNKDLPAPIERTIS
KPKGSVRAPQVYVLPPPEEEMTKKQVTLTCMVTDFMPEDIYVEWTNNGKTELNYKNTEPV
LDSDGSYFMYSKLRVEKKNWVERNSYSCSVVHEGLHNHHTTKSFSRTPGRKRRAPVKQTL
NFDLLKLAGDVESNPGPMETDTLLLWVLLLWVPGSTGDIVMSQSPSSLAVSVGEKVTMSC
KSSQSLLNSRNQKNHLAWYQQKPGQSPKLLIYWASTRESGVPDRFTGDGSGTDFTLTISS
VKAEDLAVYYCQQYYTYRTFGGGTKLEIKRADAAPTVSIFPPSSEQLTSGGASVVCFLNN
FYPKDINVKWKIDGSERQNGVLNSWTDQDSKDSTYSMSSTLTLTKDEYERHNSYTCEATH
KTSTSPIVKSFNRNEC*

FIGURE 14B

HEMAGGLUTININ-SPECIFIC ANTIBODIES AND USES THEREOF

RELATED APPLICATIONS

This application is a national stage filing under 35 U.S.C. § 371 of International Patent Application Serial No. PCT/IB2018/050493, filed on Jan. 26, 2018, which claims benefit under 35 U.S.C § 119(e) from U.S. Provisional Application No. 62/451,230, filed on Jan. 27, 2017, the entire contents of each of which are incorporated herein by reference.

FIELD OF THE INVENTION

The present invention relates to hemagglutinin-specific antibodies, fragments thereof, and uses thereof. More specifically, the present invention relates to hemagglutinin-specific antibodies and fragments thereof able to recognize antigen from multiple influenza strains.

BACKGROUND OF THE INVENTION

Influenza is an infectious disease caused by the influenza virus which belongs to the Orthomyxoviridae family. Based on their core proteins, influenza viruses are classified into types A, B, and C. The two main types of influenza virus responsible for seasonal flu epidemics are types A and B. Influenza A virus can be further characterized by serotype based on the hemagglutinin (HA) and neuraminidase (NA) proteins on the viral surface. Currently, there are 18 known subtypes of HA and 11 subtypes of NA. Based on HA subtypes, influenza A viruses are further divided into two phylogenetic groups: group 1 (H1, H2, H5, H6, H8, H9, H11, H12, H13, H16, H17 and H18) and group 2 (H3, H4, H7, H10, H14 and H15). Point mutations in the viral genome RNA of a given HA subtype already in circulation, or a new subtype of HA that arises through antigenic shift (Kang et al., 2011) can result in an influenza pandemic.

According to the World Health Organization (WHO), the influenza virus is responsible for up to 500,000 deaths per year worldwide. In order to combat the potential fatal effect of influenza virus, vaccines are produced yearly and administered to global populations. However, there are thousands of influenza virus strains. Presently, each strain requires a specific antibody for detection and quantification of HA, the most abundant protein expressed at the surface of the virus. Regulatory agencies such as the WHO are responsible for producing and distributing the antibodies used to quantify new vaccine lots throughout the world. Antibody production can take from 3 up to 16 weeks, which causes significant delays for the vaccine industry.

Generally, quantification of new vaccine lots is the bottleneck in vaccine distribution. Quantification of HA is currently performed using an assay called the Single Radial Immunodiffusion (SRID) assay. However, this assay is lengthy, laborious, and highly variable depending on the operator. In addition, standardised reagents necessary for SRID (polyclonal sera and antigen), need to be updated every year, which takes 12-16 weeks and is reliant on obtaining purified HA antigen. While the SRID assay is the only quantification method that is officially accepted by regulatory agencies, alternative quantification methods such as Enzyme-Linked Immunosorbent Assays (ELISA) could be more efficient.

Currently, specific antibodies against each strain are generated by injecting animals with isolates from each strain. However, the use of strain-specific antibodies can cause delays in releasing new vaccine lots. Using antibodies with broad specificity can speed up the detection and quantification of new influenza strains. To date, only two pan-HA antibodies are able to recognize all 3 groups of influenza commonly circulating in humans (type A group 1, type A group 2, and type B).

CR9114 is a human monoclonal antibody that was isolated using combinatorial display library derived from human B cells of subjects exposed to influenza (Dreyfus et al, 2012). CR9114 was shown to detect 10 influenza B viruses, as well as five HA belonging to influenza A (three from group 1 and two from group 2), but was not tested against all subtypes. However, its ability to recognize all HA subtypes remains untested.

Uni-1 was raised at Health Canada against a peptide sequence that is known to be highly conserved among influenza strains: GLFGAIAGFIEGGW (SEQ ID NO:29). The peptide sequence was derived from the HA fusion peptide, which was selected using bioinformatics analyses. Notably, Uni-1 was able to detect 13 different HA subtypes (H1 to H13) as well as B/Malaysia/2506/2004 by western blot (Chun et al, 2008).

Unfortunately, the main constraint with Uni-1 is that the antibodies are polyclonal rabbit antibodies, which result in high lot to lot variations. Additionally, the peptide used to raise Uni-1 was unable to elicit an immune response in mice, which has prevented production of monoclonal antibodies.

Thus, while some success has been achieved in the influenza field to generate antibodies with broad specificity to influenza HA, it is limited and not without drawbacks. The influenza community continues to seek faster and more accurate quantification methods to improve or replace the SRID assay, which could speed up the vaccine production and delivery system.

SUMMARY OF THE INVENTION

The present invention relates to hemagglutinin-specific antibodies, fragments thereof, and uses thereof. More specifically, the present invention relates to hemagglutinin-specific antibodies and fragments thereof able to recognize antigen from multiple influenza strains.

The present invention provides an isolated or purified antibody or fragment thereof, comprising:

a) a light chain comprising a complementarity determining region (CDR) L1 sequence of QSLLNSX$_1$X$_2$QKNX$_3$ (SEQ ID NO:1) where X$_1$=R or D, X$_2$=N or T, X$_3$=H or F; a CDR L2 sequence of X$_1$AS where X$_1$=W or F; and a CDR L3 sequence of QQYYX$_1$X$_2$X$_3$X$_4$T (SEQ ID NO:2) where X$_1$=T or S, X$_2$=Y or I, X$_3$=P or no amino acid, X$_4$=R or L, and b) a heavy chain comprising a complementarity determining region (CDR) H1 sequence of GYX$_1$X$_2$TX$_3$DYY (SEQ ID NO:3) where X$_1$=S or T, X$_2$=I or F, X$_3$=S or no amino acid;

a CDR H2 sequence selected from the group consisting of IGYDGX$_1$K (SEQ ID NO:4) where X$_1$=S or T, and IYPGNGHT (SEQ ID NO:5), and a CDR H3 sequence selected from the group consisting of TRDRANWDDYFDY (SEQ ID NO:6) and AYDLFNY (SEQ ID NO:7).

In one non-limiting example, the isolated or purified antibody or fragment described above may comprise a CDR L1 that is selected from the group consisting of QSLLNSRNQKNH (SEQ ID NO:8) and QSLLNSDTQKNF (SEQ ID NO:9).

In another non-limiting example, the isolated or purified antibody or fragment thereof as previously described may comprise a CDR L2 that is selected from the group consisting of WAS and FAS.

In another non-limiting example, the isolated or purified antibody or fragment thereof as described above may comprise a CDR L3 that is selected from the group consisting of QQYYTYXRT (SEQ ID NO:10) where X is P or no amino acid and QQYYSIPLT (SEQ ID NO:11).

In yet another non-limiting example, the isolated or purified antibody or fragment thereof as described above may comprise a CDR H1 selected from the group consisting of GYSITSDYY (SEQ ID NO:12) and GYTFTDYY (SEQ ID NO:13).

In a more specific example, the isolated or purified antibody or fragment thereof may comprise a sequence that may be selected from the group consisting of:
 a) a light chain comprising CDR L1 of sequence QSLLNSRNQKNH (SEQ ID NO:8), CDR L2 of sequence WAS, and CDR L3 of sequence QQYYTYRT (SEQ ID NO:14); and a heavy chain comprising CDR H1 of sequence GYSITSDYY (SEQ ID NO:12), CDR H2 of sequence IGYDGSK (SEQ ID NO:15), and CDR H3 of sequence TRDRANWDDYFDY (SEQ ID NO:6);
 b) a light chain comprising CDR L1 of sequence QSLLNSRNQKNH (SEQ ID NO:8), CDR L2 of sequence WAS, and CDR L3 of sequence QQYYTYRT (SEQ ID NO:14); and a heavy chain comprising CDR H1 of sequence GYSITSDYY (SEQ ID NO:12), CDR H2 of sequence IGYDGTK (SEQ ID NO:16), and CDR H3 of sequence TRDRANWDDYFDY (SEQ ID NO:6); and
 c) a light chain comprising CDR L1 of sequence QSLLNSDTQKNF (SEQ ID NO:9), CDR L2 of sequence FAS, CDRL3 of sequence QQYYSIPLT (SEQ ID NO:11); and a heavy chain comprising CDR H1 of sequence GYTFTDYY (SEQ ID NO:13), CDR H2 of sequence IYPGNGHT (SEQ ID NO:5), and CDR H3 of sequence AYDLFNY (SEQ ID NO:7).

More specifically, the isolated or purified antibody or fragment thereof may comprise a variable light (VL) domain having a sequence of:
DIVMX$_1$QSPSSLAX$_2$SVGX$_3$KVTMSCKSSQSLLNSX$_4$X$_5$QKNX$_8$LAWYQQKPGQS PKX$_7$LX$_8$YX$_9$ASTX$_{10}$ESGVPDRFX$_{11}$GX$_{12}$GSGTDFTLTIX$_{13}$SVX$_{14}$AEDLAX$_{15}$YX$_{16}$C QQYYX$_{17}$X$_{18}$X$_{19}$X$_{20}$TFGX$_{21}$GTKLEIK (SEQ ID NO:17), where X$_1$=S or T, X$_2$=V or M, X$_3$=E or O, X$_4$=R or D, X$_5$=N or T, X$_6$=H or F, X$_7$=L or I, X$_8$=I or V, X$_9$=W or F, X$_{10}$=R or K, X$_{11}$=S or I, X$_{12}$=D or S, X$_{13}$=S or T, X$_{14}$=K or Q, X$_{15}$=V or D, X$_{16}$=Y or F, X$_{17}$=T or S, X$_{18}$=Y or I, X$_{19}$=P or no amino acid, X$_{20}$=R or L, X$_{21}$=G or A.

In an even more specific example, the variable light (VL) domain may comprise a sequence selected from the group consisting of:
 DIVMSQSPSSLAVSVGEKVTMSCKSSQSLLNSRNQKNHLAWYQQKPGQSPKL LIYWASTRESGVPDRFX$_1$GDGSGTDFTLTISSVKAEDLAVYYCQQYYTYRTFGG GTKLEIK (SEQ ID NO:18) where X$_1$=S or T;
 DIVMTQSPSSLAMSVGQKVTMSCK SSQSLLNSDTQKNFLAWYQQKPGQSPKIL VYFASTKESGVPDRFIGSGSGTDFTLTITSVQAE DLADYFCQQYYSIPLTFGAGT KLELK (SEQ ID NO:19); and
 a sequence substantially identical thereto.

In the isolated or purified antibody or fragment as described above, the variable heavy (VH) domain may comprise a sequence selected from the group consisting of:
 DVQLQESGPGLVKP-SQSLSLTCSVTGYSITSDYYWNWIRQFPGN-KLEWMAYIG YDGX$_1$KNYNPSLKNRISITRDTSKNQFFLKLNS-VTTDDTATYYCTRDRANWDDY FDYWGQGT-TLTVSS (SEQ ID NO:20) where X$_1$=S or T;
 QIQLQQSGPELVKPGAPVKISCK-ASGYTFTDYYIHWVNQRPGQGLEWIGYIYPG NGHTVYNQKFKVRATLTADNPSSTAYLQLNSLT-SEDSGVYFCAYDLFNYWGQ GTLVTVSA (SEQ ID NO:21); and
a sequence substantially identical thereto.

In specific, non-limiting examples, the isolated or purified antibody or fragment thereof may comprise:
 a) a variable light (V$_L$) domain of sequence:

```
                                        (SEQ ID NO: 22)
DIVMSQSPSSLAVSVGEKVTMSCKSSQSLLNSRNQKNHLAWYQQKPGQS

PKLLIYWASTRESGVPDRFSGDGSGTDFTLTISSVKAEDLAVYYCQQYY

TYRTFGGGTKLEIK;
``` and variable heavy (V$_H$) domain of sequence:

```
                                        (SEQ ID NO: 24)
DVQLQESGPGLVKPSQSLSLTCSVTGYSITSDYYWNWIRQFPGNKLEWM

AYIGYDGSKNYNPSLKNRISITRDTSKNQFFLKLNSVTTDDTATYYCTR

DRANWDDYFDYWGQGTTLTVSS;
``` or b) a variable light (V$_L$) domain of sequence:

```
                                        (SEQ ID NO: 23)
DIVMSQSPSSLAVSVGEKVTMSCKSSQSLLNSRNQKNHLAWYQQKPGQS

PKLLIYWASTRESGVPDRFTGDGSGTDFTLTISSVKAEDLAVYYCQQYY

TYXRTFGGGTKLEIK;
``` and variable heavy (V$_H$) domain of sequence:

```
                                        (SEQ ID NO: 25)
DVQLQESGPGLVKPSQSLSLTCSVTGYSITSDYYWNWIRQFPGNKLEWM

AYIGYDGTKNYNPSLKNRISITRDTSKNQFFLKLNSVTTDDTATYYCTR

DRANWDDYFDYWGQGTTLTVSS;
``` or c) a variable light (V$_L$) domain of sequence:

```
                                        (SEQ ID NO: 19)
DIVMTQSPSSLAMSVGQKVTMSCKSSQSLLNSDTQKNFLAWYQQKPGQS

PKILVYFASTKESGVPDRFIGSGSGTDFTLTITSVQAEDLADYFCQQYY

SIPLTFGAGTKLELK;
``` and variable heavy (V$_H$) domain of sequence:

(SEQ ID NO: 21)
QIQLQQSGPELVKPGAPVKISCKASGYTFTDYYIHWVNQRPGQGLEWIGY

IYPGNGHTVYNQKFKVRATLTADNPSSTAYLQLNSLTSEDSGVYFCAYDL

FNYWGQGTLVTVSA;

or d) a sequence substantially identical thereto.

The antibody or fragment thereof of the present invention, as defined above, may specifically bind hemagglutinin.

The isolated or purified antibody or fragment thereof as described herein may be a full-length IgG, Fv, scFv, Fab, or F(ab')$_2$ fragments; the antibody or fragment thereof may also comprise framework regions from IgA, IgD, IgE, IgG, or IgM. The isolated or purified antibody or fragment thereof of the present invention may be chimeric; or example, and without wishing to be limiting, such a chimeric antibody or fragment thereof may comprise the V$_L$ and V$_H$ domains from mouse and framework regions (constant domains) from human IgG1, more specifically human kappa 1 light chain and human IgG1 heavy chain.

The present invention also provides a nucleic acid molecule encoding the isolated or purified antibody or fragment thereof as described herein. A vector comprising the nucleic acid molecule as herein described is also provided.

The isolated or purified antibody or fragment thereof as described herein may be immobilized onto a surface, or may be linked to a cargo molecule. The cargo molecule may be a detectable agent, a therapeutic agent, a drug, a peptide, an enzyme, a growth factor, a cytokine, a receptor trap, an antibody or fragment thereof (e.g., IgG, scFv, Fab, V$_H$H, etc) a chemical compound, a carbohydrate moiety, DNA-based molecules (anti-sense oligonucleotide, microRNA, siRNA, plasmid), a neutralizing agent, viral vector (adeno-, lenti-, retro-), one or more liposomes or nanocarriers loaded with any of the previously recited types of cargo molecules, or one or more nanoparticle, nanowire, nanotube, or quantum dots. In a specific, non-limiting example, the cargo molecule is a neutralizing agent.

Additionally, the present invention provides a composition comprising one or more than one isolated or purified antibody or fragment thereof as described herein and a pharmaceutically-acceptable carrier, diluent, or excipient.

An in vitro method of detecting hemagglutinin is also provided, the method comprising the steps of:
a) contacting a tissue sample with an (one or more than one) isolated or purified antibody or fragment thereof as described herein linked to a detectable agent; and
b) detecting the detectable agent linked to the antibody or fragment thereof bound to hemagglutinin in the tissue sample.

In the method described above, the method may detect hemagglutinin in circulating cells and the sample may be a serum sample, lung tissue sample, neuroepithelium tissue sample, or other tissue from the respiratory system. In the method as described, the step of detecting (step b)) may be performed using optical imaging, immunohistochemistry, molecular diagnostic imaging, immunoassays such as ELISA, Western blot, dot blot, slot blot, or other suitable method.

Hemagglutinin is a protein expressed at the surface of the influenza virus. Due to antigenic drift and shift, each new strain of influenza generally requires a specific antibody for its recognition. Presently, three novel antibodies [11H12 (SEQ ID NO. 36), 10A9 (SEQ ID NO. 35) and 9D1] have been identified that specifically bind hemagglutinin. The novel antibodies described herein are able to detect and bind multiple strains encompassing 13 HA subtypes. They can be used for detection, quantification, and neutralization. Furthermore, these antibodies are monoclonal, and thus can be produced in a reproducible and scalable fashion.

The antibodies of the present invention may be use to speed up or improve the accuracy of quantification methods, which would ease the bottleneck in vaccine distribution. The antibodies could also be used with in-process and crude samples in order to optimise the bioprocess used to generate vaccines.

The present invention may also provide a method for the prevention or treatment of influenza in a subject, comprising administering an (one or more than one) isolated or purified antibody or fragment thereof as described herein to the subject Alternatively, there is also provided an isolated or purified antibody or fragment thereof as described herein for use in preventing or treating influenza in a subject.

Additional aspects and advantages of the present invention will be apparent in view of the following description. The detailed descriptions and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein:

FIG. 2A) light chains: 11H12 (SEQ ID NO:23); 10A9 (SEQ ID NO:19); and 9D1 (SEQ ID NO:22). FIG. 2B) heavy chains: 11H12 (SEQ ID NO:25); 10A9 (SEQ ID NO:21); and 9D1 (SEQ ID NO:24).

FIGS. 5A-5D show Western blot results of the reactivity of the mAb 11H12 (FIG. 5A), 10A9 (FIG. 5B), and 9D1 (FIG. 5C), as well as an anti-GFP negative control (FIG. 5D), for recombinant HA proteins. For each set of data, the purified mAb (mAb) or the unpurified hybridoma supernatant (Supernat) was used. The molecular weight of the rHA is 75KDa when uncleaved (HA$_0$). When cleaved, the fragments have a molecular weight of 45KDa (HA$_1$) and 25KDa (HA$_2$), as indicated in FIG. 5A. Each mAb was assayed against H5N1/A/Indonesia/05/2005 (H5N1); H1N1

A/Puerto Rico/08/1934 (H1N1); B/Brisbane/60/2008 (B/Brisb.); and H7N7 A/Netherlands/219/2003 (H7N7).

Figure 6A:
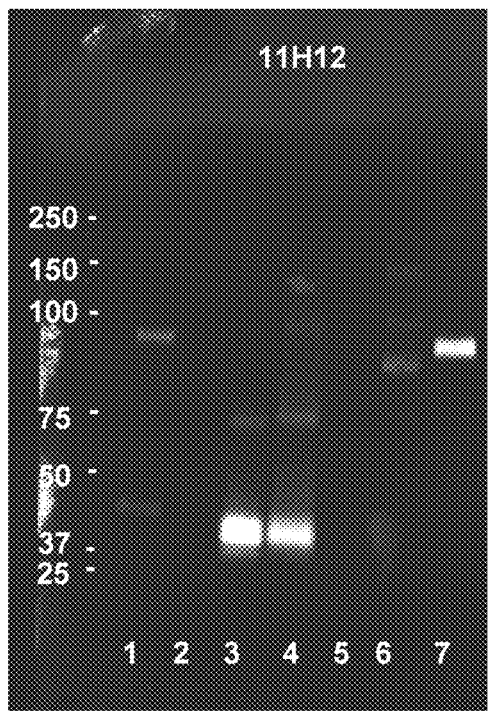
Figure 6B:
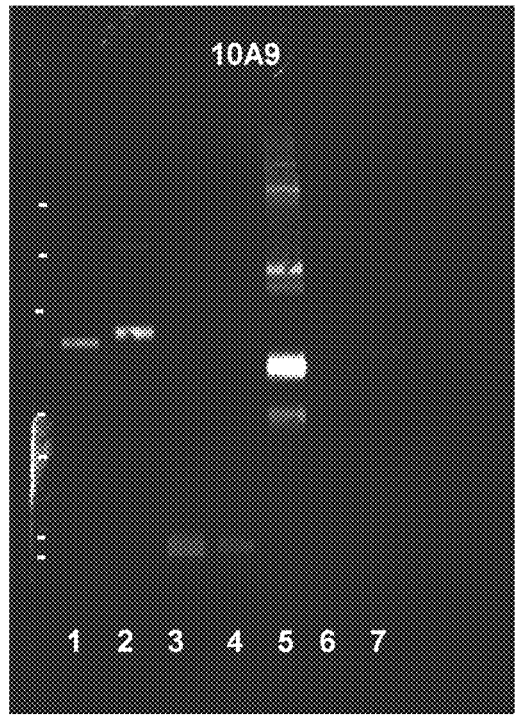
Figure 6C:
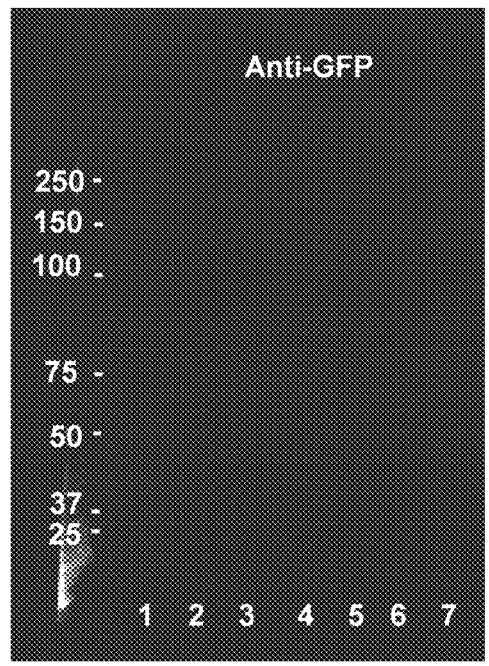
Figure 6D:
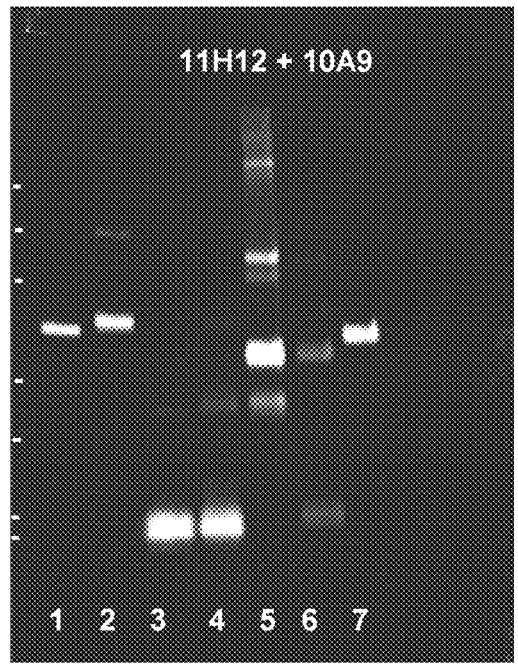

FIGS. 6A-6C show results of a second Western blot analysis of the reactivity of the 11H12 mAb (FIG. 6A), the 10A9 mAb (FIG. 6B), a mixture of the two antibodies (FIG. 6D), and an anti-GFP negative control (FIG. 6C). Lane 1, H1N1/A/California/06/2008; Lane 2, H3N2/A/Brisbane/10/2007; Lane 3, H5N1/A/Indonesia/05/2005; Lane 4, H5N1/A/Vietnam/1203/2004; Lane 5, H7N7/A/Netherlands/219/2003; Lane 6, H9N2/A/Hong Kong/1073/1999; Lane 7, B/Brisbane/60/2008.

Figure 7A:
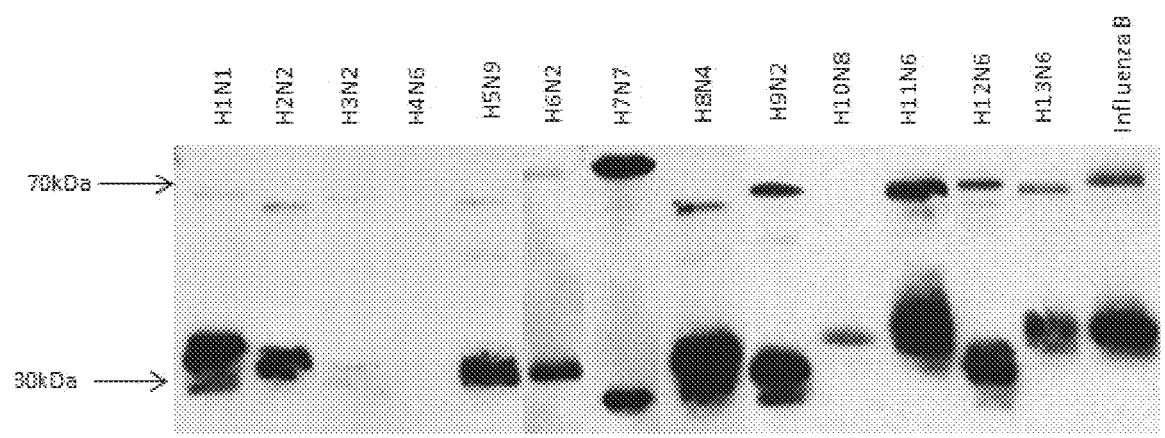
Figure 7B:
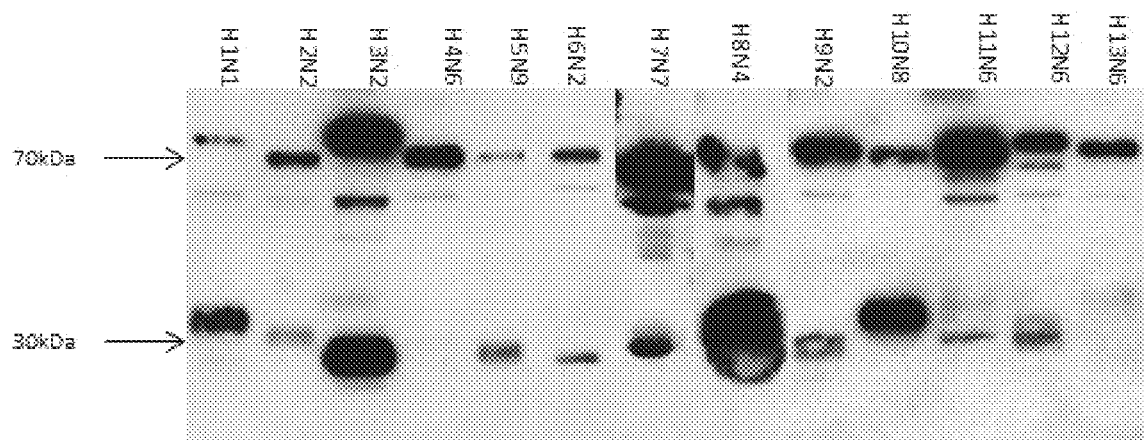

FIGS. 7A-7B show Western blot results of the reactivity of the 11H12 (FIG. 7A) and 10A9 (FIG. 7B) mAb with viruses produced in eggs. Full names of the virus strains are shown in Table 6.

Figure 8A:
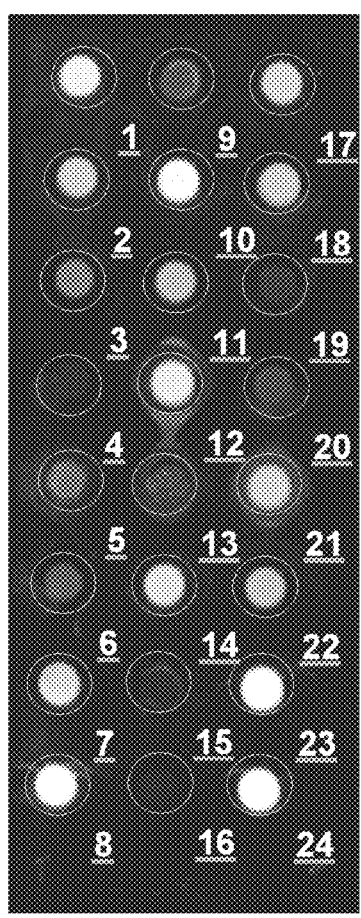
Figure 8B:
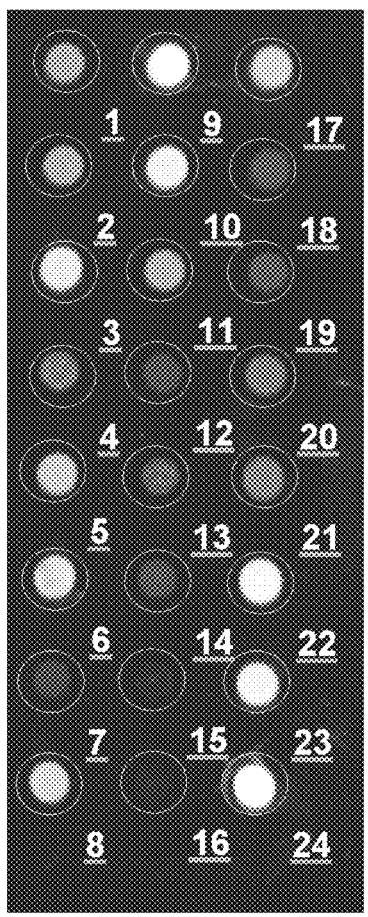
Figure 8C:
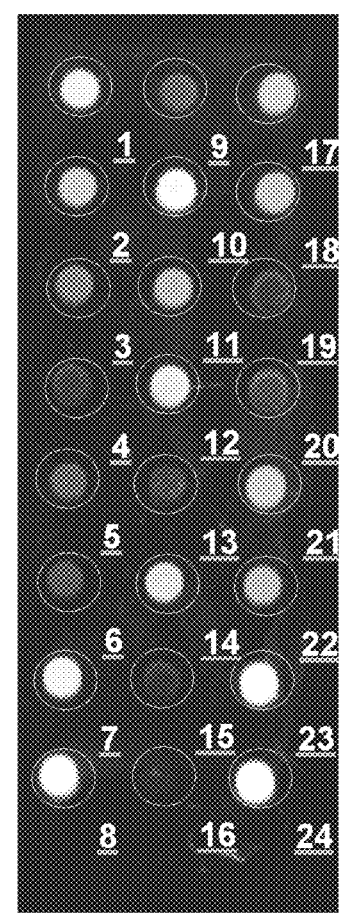

FIGS. 8A-8C show dot blot analysis of the 3mAbs: 9D1 (FIG. 8A), 10A9 (FIG. 8B) and 11H12 (FIG. 8C), tested against HA from different strains as summarized in Table 7. Values corresponding to the optical densities of each dot are also reported in Table 7.

FIGS. 9A-9C show the results of quantitative dot blot analysis with 11H12. A representative dot blot is shown in FIG. 9A. H1N1 A/Puerto Rico/8/34 virus produced in HEK293 cells were quantified by generating a standard curve (FIG. 9B). Samples were serially diluted and 4 concentrations were assayed. Sample 6 was obtained from non-infected cells and was used as a negative control (FIG. 9C).

Figure 10:
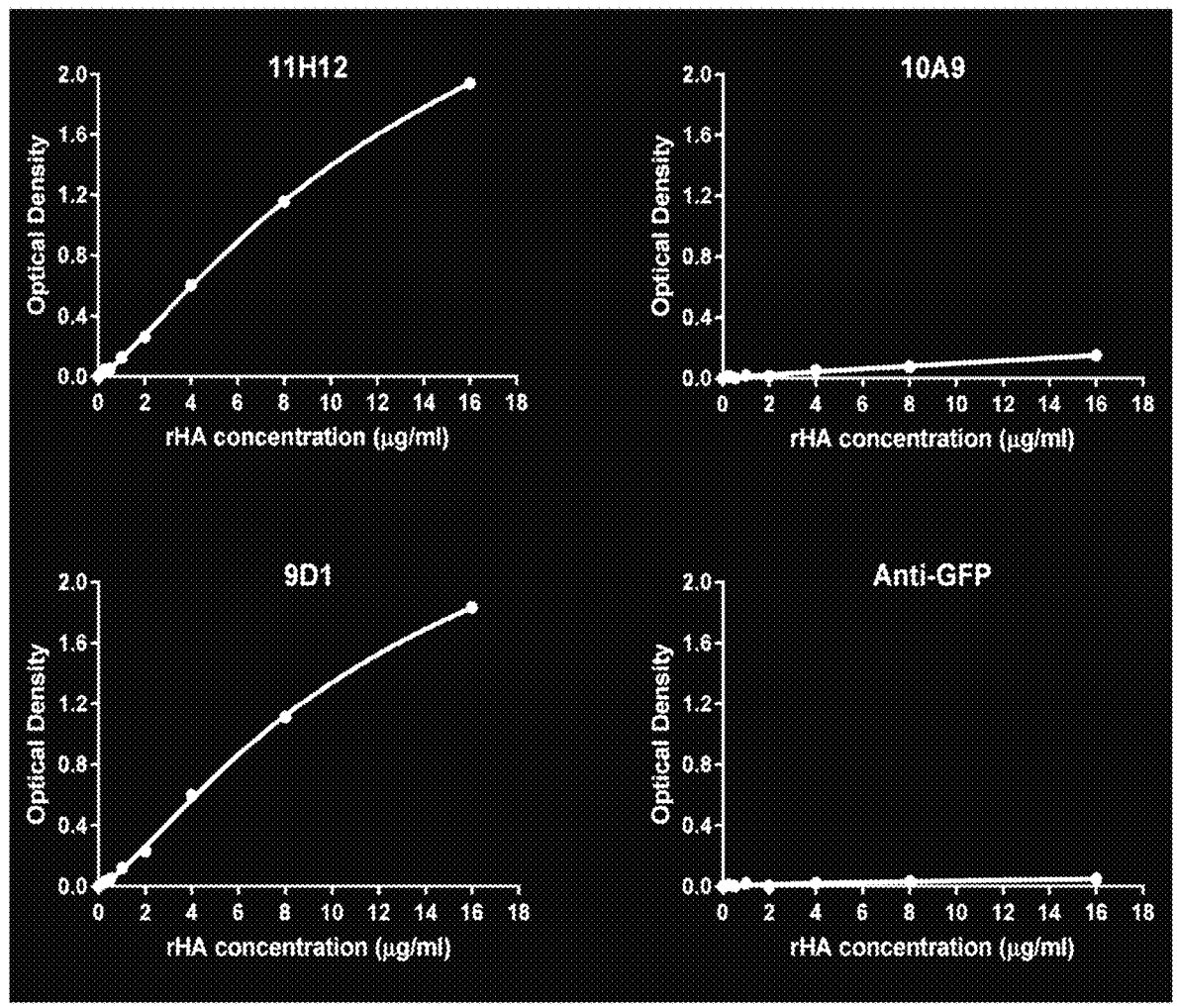

FIG. 10 shows the results of ELISA analysis of 10A9, 11H12, and 9D1. A direct ELISA was performed with the antibodies against the rHA from H5N1 A/Indonesia/05/2005. A non-related antibody (anti-GFP) was used as a negative control.

Figure 11A:
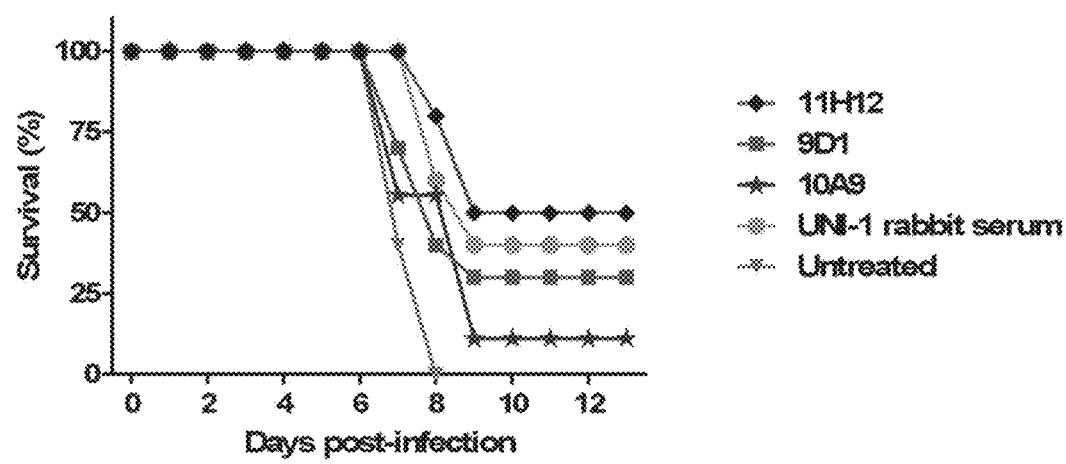
Figure 11B:
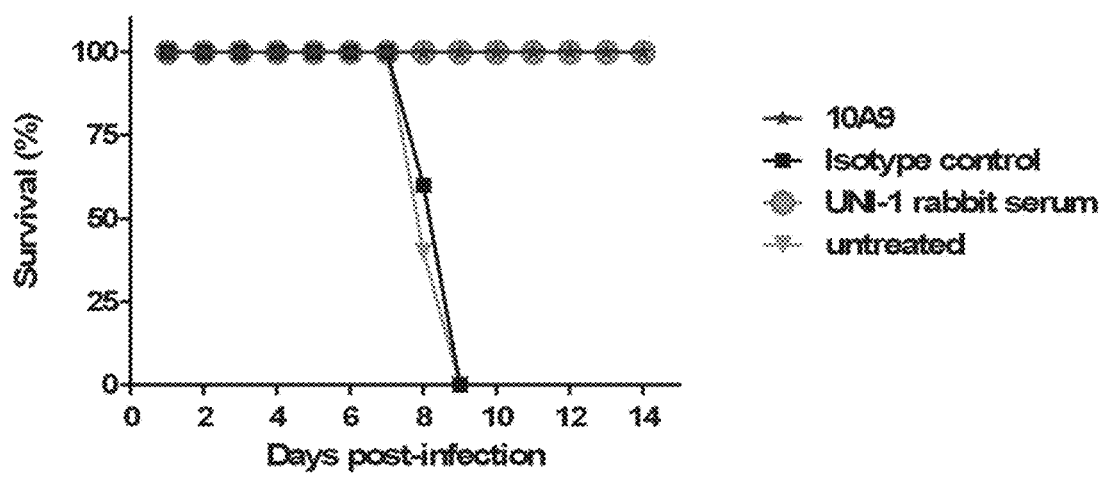

FIGS. 11A-11B show in vivo results of challenges with lethal concentrations of influenza viruses, along with several doses of antibodies to evaluate their protective/neutralizing capacity. In FIG. 11A, mice were infected intra-nasally with 750 PFU of H1N1 A/Puerto Rico/8/34; antibodies were injected at three different time points: 2 hours before infection, 4 hours post-infection and 24 hours post-infection. In FIG. 11B, mice were infected intra-nasally with $10^4$ PFU of H3N2 A/Hong Kong/8/68; antibodies were injected at 4 different time points: 24 hours before infection, 2 hours before infection, 24 hours post-infection and 72 hours post-infection.

Figure 12A:
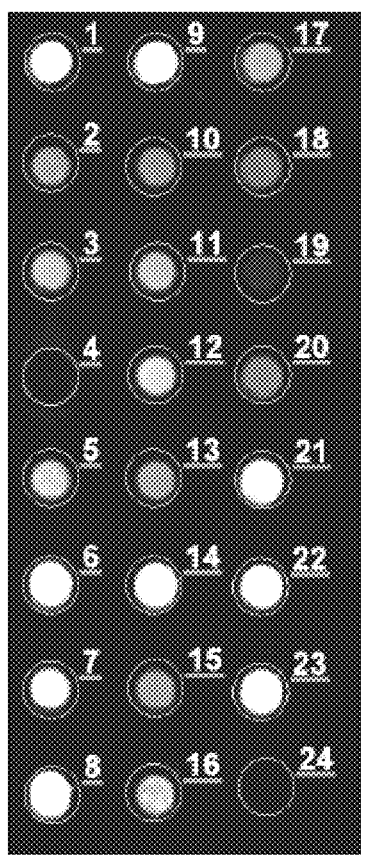
Figure 12B:
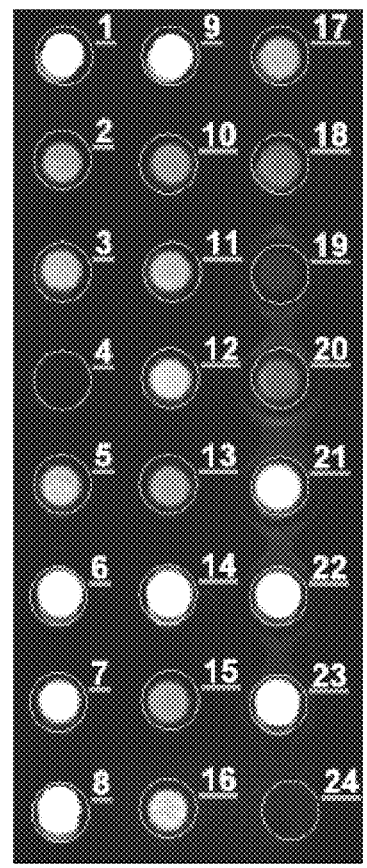

FIGS. 12A-12B. Dot blot results with a pan-HA cocktail obtained from mouse hybridomas (FIG. 12A) and CHO pools (FIG. 12B). Each dot represents a different strain as indicated in Table 9. Recombinant proteins and plant VLPs were loaded at a final concentration of 2.5 μg while the viruses and standard antigens were loaded at a concentration of 5 μg.

FIGS. 13A-13O. Primary amino acid sequence comparison analysis of IgGs: 11H12 (FIG. 13A); 10A9 (FIG. 13B); and 9D1 (FIG. 13C). Amino acid sequences identified with a Mascot score >30 are highlighted in bold.

FIGS. 14A-14B. Full protein sequences of recombinant monoclonal antibodies: 10A9 (FIG. 14A); and 11H12 (FIG. 14B).

DETAILED DESCRIPTION OF THE INVENTION

Abbreviations

DT: diphteria toxin; HA: hemagluttinin; KLH: Keyhole limpet hemocyanin; NA: neuraminidase; TT: tetanus toxoid.

Definitions

As used herein the singular forms "a", "and", and "the" include plural referents unless the context clearly dictates otherwise. Thus, for example, reference to "an antibody" includes "one or more than one" antibodies and reference to "the antibody" includes reference to one or more than one antibodies and equivalents thereof known to those skilled in the art, and so forth. All technical and scientific terms used herein have the same meaning as commonly understood to one of ordinary skill in the art to which this invention belongs unless clearly indicated otherwise.

The term "about" as used herein refers to a margin of + or – 10% of the number indicated. For sake of precision, the term about when used in conjunction with, for example: 90% means 90%+/–9% i.e. from 81% to 99%. More precisely, the term about refer to + or –5% of the number indicated, where for example: 90% means 90%+/–4.5% i.e. from 86.5% to 94.5%. When used in the context of a pH, the term "about" means+/–0.5 pH unit.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used herein, the terms "disease" may be used interchangeably or may be different in that the particular disorder, infection or condition may not have a known causative agent (so that etiology has not yet been worked out) and it is therefore not yet recognized as a disease but only as an undesirable condition or syndrome, wherein a more or less specific set of symptoms have been identified by clinicians.

The term "subject" as used herein refers to an animal, preferably a mammal or a bird, who is the object of administration, treatment, observation or experiment. "Mammal" includes humans and both domestic animals such as laboratory animals and household pets, (e.g. cats, dogs, swine, cattle, sheep, goats, horses, rabbits), and non-domestic animals such as wildlife, fowl, birds and the like. More particularly, the mammal is a rodent. Still, most particularly, the mammal is a human.

The antibody(ies) described herein can be formulated as pharmaceutical compositions by formulation with additives such as pharmaceutically acceptable excipients, pharmaceutically acceptable carriers, and pharmaceutically acceptable vehicles.

As used herein, the term "pharmaceutically acceptable" refers to molecular entities and compositions that are physiologically tolerable and do not typically produce an allergic or similar unwanted reaction, such as gastric upset, dizziness and the like, when administered to human. Preferably, as used herein, the term "pharmaceutically acceptable" means approved by regulatory agency of the federal or state government or listed in the U.S. Pharmacopeia or other generally recognized pharmacopeia for use in animals, and more particularly in humans.

The terms "carrier," "diluent" or "excipient" each refers to a vehicle with which the antibodies of the present invention may be administered. Sterile water or aqueous saline solutions and aqueous dextrose and glycerol solutions may be employed as carrier, particularly for injectable solutions. Suitable pharmaceutical carriers are described in "Remington's Pharmaceutical Sciences" by E. W. Martin.

If administered as a medicinal preparation, the antibodies can be administered, either as a prophylaxis or treatment, to a patient by a number of methods. The present compositions may be administered alone or in combination with other pharmaceutical antibodies and can be combined with a physiologically acceptable carrier thereof. The effective amount and method of administration and aim of the present formulation can vary based on the individual subject, the stage of the disease or condition, and other factors apparent to one skilled in the art. In the case of a pharmaceutical formulation, during the course of the treatment, the concentration of the present compositions may be monitored (for example, blood antibody levels may be monitored) to ensure that the desired response is obtained.

Detailed Description of Particular Embodiments

The present invention relates to hemagglutinin-specific antibodies, fragments thereof, and uses thereof. More specifically, the present invention relates to hemagglutinin-specific antibodies and fragments thereof able to recognize antigen from multiple influenza strains.

The present invention provides an isolated or purified antibody or fragment thereof, comprising:

a) a light chain comprising a complementarity determining region (CDR) L1 sequence of QSLLNS$X_1X_2$QKN$X_3$ (SEQ ID NO:1) where $X_1$=R or D, $X_2$=N or T, $X_3$=H or F; a CDR L2 sequence of $X_1$AS where $X_1$=W or F; and a CDR L3 sequence of QQYY$X_1X_2X_3X_4$T (SEQ ID NO:2) where $X_1$=T or S, $X_2$=Y or I, $X_3$=P or no amino acid, $X_4$=R or L, and b) a heavy chain comprising a complementarity determining region (CDR) H1 sequence of GY$X_1X_2$T$X_3$DYY (SEQ ID NO:3) where $X_1$=S or T, $X_2$=l or F, $X_3$=S or no amino acid;

a CDR H2 sequence selected from the group consisting of IGYDG$X_1$K (SEQ ID NO:4) where $X_1$=S or T and IYPGNGHT (SEQ ID NO:5); and a CDR H3 sequence selected from the group consisting of TRDRANWDDYFDY (SEQ ID NO:6) and AYDLFNY (SEQ ID NO:7).

The term "antibody", also referred to in the art as "immunoglobulin" (Ig), as used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant (CO domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen-binding determinants of the molecule, and thus determines the specificity of an antibody for its target antigen. The majority of sequence variability occurs in six hypervariable regions, three each per variable heavy ($V_H$) and light ($V_L$) chain; the hypervariable regions combine to form the antigen-binding site, and contribute to binding and recognition of an antigenic determinant. The specificity and affinity of an antibody for its antigen is determined by the structure of the hypervariable regions, as well as their size, shape, and chemistry of the surface they present to the antigen. Various schemes exist for identification of the regions of hypervariability, the two most common being those of Kabat and of Chothia and Lesk. Kabat et al (1991) define the "complementarity-determining regions" (CDR) based on sequence variability at the antigen-binding regions of the $V_H$ and $V_L$ domains. Chothia and Lesk (1987) define the "hypervariable loops" (H or L) based on the location of the structural loop regions in the $V_H$ and $V_L$ domains. As these individual schemes define CDR and hypervariable loop regions that are adjacent or overlapping, those of skill in the antibody art often utilize the terms "CDR" and "hypervariable loop" interchangeably, and they may be so used herein. A more recent scheme is the IMGT numbering system (Lefranc et al., 2003), which was developed to facilitate comparison of variable domains. In this system, conserved amino acids (such as Cys23, Trp41, Cys104, Phe/Trp118, and a hydrophobic residue at position 89) always have the same position. Additionally, a standardized delimitation of the framework regions (FR1: positions 1 to 26; FR2: 39 to 55; FR3: 66 to 104; and FR4: 118 to 129) and of the CDR (CDR1: 27 to 38, CDR2: 56 to 65; and CDR3: 105 to 117) is provided.

The CDR/loops are referred to herein according to the IMGT numbering system for all CDR. The CDR of the antibodies of the present invention are referred to herein as CDR L1, L2, L3 for CDR in the light chain, and CDR H1, H2, H3 for CDR in the heavy chain.

An "antibody fragment" as referred to herein may include any suitable antigen-binding antibody fragment known in the art. The antibody fragment may be a naturally-occurring antibody fragment, or may be obtained by manipulation of a naturally-occurring antibody or by using recombinant methods. For example, an antibody fragment may be selected from the group consisting of, but is not limited to a Fv, single-chain Fv (scFv; a molecule consisting of $V_L$ and $V_H$ connected with a peptide linker), Fab, $F(ab')_2$, and multivalent presentations of any of these. Antibody fragments such as those herein described may require linker sequences, disulfide bonds, or other type of covalent bond to link different portions of the fragments; those of skill in the art will be familiar with various approaches.

The terms "antibody" and "antibody fragment" ("fragment thereof") as defined above may be from any selected from the group consisting of source, human, mouse, or other; may be any isotype selected from the group consisting of IgA, IgD, IgE, IgG, and IgM; and may be any type of fragment, including but not limited to Fv, scFv, Fab, and $F(ab')_2$.

In one non-limiting example, the isolated or purified antibody or fragment described above may comprise a CDR L1 that is selected from the group consisting of QSLLNSRNQKNH (SEQ ID NO:8) and QSLLNSDTQKNF (SEQ ID NO:9).

In another non-limiting example, the isolated or purified antibody or fragment thereof as previously described may comprise a CDR L2 that is selected from the group consisting of WAS and FAS.

In another non-limiting example, the isolated or purified antibody or fragment thereof as described above may comprise a CDR L3 that is selected from the group consisting of QQYYTYXRT (SEQ ID NO:10) where X is P or no amino acid, and QQYYSIPLT (SEQ ID NO:11).

In yet another non-limiting example, the isolated or purified antibody or fragment thereof as described above may comprise a CDR H1 is selected from the group consisting of GYSITSDYY (SEQ ID NO:12) and GYTFTDYY (SEQ ID NO:13).

In a more specific example, the isolated or purified antibody or fragment thereof may be selected from the group consisting of:
a) a light chain comprising CDR L1 of sequence QSLLNSRNQKNH (SEQ ID NO:8), CDR L2 of sequence WAS, and CDR L3 of sequence QQYYTYRT (SEQ ID NO:14); and a heavy chain comprising CDR H1 of sequence GYSITSDYY (SEQ ID NO:12), CDR H2 of sequence IGYDGSK (SEQ ID NO:15), and CDR H3 of sequence TRDRANWDDYFDY (SEQ ID NO:6);
b) a light chain comprising CDR L1 of sequence QSLLNSRNQKNH (SEQ ID NO:8), CDR L2 of sequence WAS, and CDR L3 of sequence QQYYTYRT (SEQ ID NO:17); and a heavy chain comprising CDR H1 of sequence GYSITSDYY (SEQ ID NO:12), CDR H2 of sequence IGYDGTK (SEQ ID NO:16), and CDR H3 of sequence TRDRANWDDYFDY (SEQ ID NO:6); and
c) a light chain comprising CDR L1 of sequence QSLLNSDTQKNF (SEQ ID NO:9), CDR L2 of sequence FAS, CDRL3 of sequence QQYYSIPLT (SEQ ID NO:11); and a heavy chain comprising CDR H1 of sequence GYTFTDYY (SEQ ID NO:13), CDR H2 of sequence IYPGNGHT (SEQ ID NO:5), and CDR H3 of sequence AYDLFNY (SEQ ID NO:7).

More specifically, the isolated or purified antibody or fragment thereof may comprise a variable light (VL) domain having a sequence of:
DIVMX$_1$QSPSSLAX$_2$SVGX$_3$KVTMSCKSSQSLLNSX$_4$X$_5$QKNX$_6$LAWYQQKPGQS PKX$_7$LX$_8$YX$_9$ASTX$_{10}$ ESGVPDRFX$_{11}$GX$_{12}$GSGTDFTLTIX$_{13}$SVX$_{14}$AEDLAX$_{15}$YX$_{16}$C QQYYX$_{17}$X$_{18}$X$_{19}$X$_{20}$TFGX$_{21}$GTKLEIK (SEQ ID NO:17) where X$_1$=S or T, X$_2$=V or M, X$_3$=E or O, X$_4$=R or D, X$_5$=N or T, X$_6$=H or F, X$_7$=L or I, X$_8$=l or V, X$_6$=W or F, X$_{10}$=R or K, X$_{11}$=S or I, X$_{12}$=D or S, X$_{13}$=S or T, X$_{14}$=K or Q, X$_{15}$=V or D, X$_{16}$=Y or F, X$_{17}$=T or S, X$_{18}$=Y or I, X$_{19}$=P or no amino acid, X$_{20}$=R or L, X$_{21}$=G or A.

In a more specific example, the variable light (VL) domain may comprise a sequence selected from the group consisting of:
a) DIVMSQSPSSLAVSVGEKVTMSCKSSQSLLNSRNQKNHLAWYQQKPGQS PKWYWASTRESGVPDRFX$_1$GDGSGTDFTLTISSVKAEDLAVYYCQQYYTY RTFGGGTKLEIK (SEQ ID NO:18) where X$_1$=S or T;
b) DIVMTQSPSSLAMSVGQKVTMSCKSSQSLLNSDTQKNFLAWYQQKPGQS PKILVYFASTKESGVPDRFIGSGSGTDFTLTITSVQAEDLADYFCQQYYSIPL TFGAGTKLELK (SEQ ID NO:19); and
c) a sequence substantially identical thereto.

In the isolated or purified antibody or fragment as described above, the variable heavy (VH) domain may comprise a sequence selected from the group consisting of:
a) DVQLQESGPGLVKPSQSLSLTCSVTGYSITSDYYWNWIRQFPGNKLEWMA YIGYDGX$_1$KNYNPSLKNRISITRDTSKNQFFLKLNSVTTDDTATYYCTRDRAN WDDYFDYWGQGTTLTVSS (SEQ ID NO:20) where X$_1$=S or T;
b) QIQLQQSGPELVKPGAPVKISCKASGYTFTDYYIHWVNQRPGQGLEWIGYI YPGNGHTVYNQKFKVRATLTADNPSSTAYLQLNSLTSEDSGVYFCAYDLFN YWGQGTLVTVSA (SEQ ID NO:21); and
c) a sequence substantially identical thereto.

In specific, non-limiting examples, the isolated or purified antibody or fragment thereof may comprise:
a) a variable light (V$_L$) domain of sequence:

```
                                              (SEQ ID NO: 22)
DIVMSQSPSSLAVSVGEKVTMSCKSSQSLLNSRNQKNHLAWYQQKPGQSP

KLLIYWASTRESGVPDRFSGDGSGTDFTLTISSVKAEDLAVYYCQQYYTY

RTFGGGTKLEIK
``` and variable heavy (V$_H$) domain of sequence:

```
                                              (SEQ ID NO: 24)
DVQLQESGPGLVKPSQSLSLTCSVTGYSITSDYYWNWIRQFPGNKLEWMA

YIGYDGSKNYNPSLKNRISITRDTSKNQFFLKLNSVTTDDTATYYCTRDR

ANWDDYFDYWGQGTTLTVSS;
``` or
b) a variable light (V$_L$) domain of sequence:

```
                                              (SEQ ID NO: 23)
DIVMSQSPSSLAVSVGEKVTMSCKSSQSLLNSRNQKNHLAWYQQKPGQSP

KLLIYWASTRESGVPDRFTGDGSGTDFTLTISSVKAEDLAVYYCQQYYTY

XRTFGGGTKLEIK;
``` and variable heavy (V$_H$) domain of sequence:

```
                                              (SEQ ID NO: 25)
DVQLQESGPGLVKPSQSLSLTCSVTGYSITSDYYWNWIRQFPGNKLEWMA

YIGYDGTKNYNPSLKNRISITRDTSKNQFFLKLNSVTTDDTATYYCTRDR

ANWDDYFDYWGQGTTLTVSS;
``` or
c) a variable light (V$_L$) domain of sequence:

```
                                              (SEQ ID NO: 19)
DIVMTQSPSSLAMSVGQKVTMSCKSSQSLLNSDTQKNFLAWYQQKPGQSP

KILVYFASTKESGVPDRFIGSGSGTDFTLTITSVQAEDLADYFCQQYYSI

PLTFGAGTKLELK;
``` and variable heavy (V$_H$) domain of sequence:

```
                                              (SEQ ID NO: 21)
QIQLQQSGPELVKPGAPVKISCKASGYTFTDYYIHWVNQRPGQGLEWIGY

IYPGNGHTVYNQKFKVRATLTADNPSSTAYLQLNSLTSEDSGVYFCAYDL

FNYWGQGTLVTVSA;
``` or
d) a sequence substantially identical thereto.

A substantially identical sequence may comprise one or more conservative amino acid mutations. It is known in the art that one or more conservative amino acid mutations to a reference sequence may yield a mutant peptide with no substantial change in physiological, chemical, physico-chemical or functional properties compared to the reference sequence; in such a case, the reference and mutant sequences would be considered "substantially identical" polypeptides. A conservative amino acid substitution is defined herein as the substitution of an amino acid residue for another amino acid residue with similar chemical properties (e.g. size, charge, or polarity). These conservative amino acid mutations may be made to the framework regions of the antibody or fragment thereof while maintaining the CDR sequences listed above and the overall structure of the antibody or fragment; thus, the specificity and binding of the antibody are maintained.

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), or any other appropriate software that is known in the art.

The substantially identical sequences of the present invention may be at least 90% identical; in another example, the substantially identical sequences may be at least 90, 91, 92, 93, 94, 95, 96, 97, 98, 99, or 100% identical, or any percentage therebetween, at the amino acid level to sequences described herein. Importantly, the substantially identical sequences retain the activity and specificity of the reference sequence. In a non-limiting embodiment, the difference in sequence identity may be due to conservative amino acid mutation(s). In a non-limiting example, the present invention may be directed to an antibody or fragment thereof comprising a sequence at least 95%, 98% or 99% identical to that of the antibodies described herein.

The antibodies as described herein may comprise the $V_L$ and $V_H$ domains as described above and one or more than one constant regions from mouse IgG2a.

The present invention further encompasses an antibody or fragment thereof that is chimeric (or chimerized), veneered, or humanized. The antibody or fragment thereof as described herein may be chimeric, in that the antibody or fragment thereof is a combination of protein sequences originating from more than one species. As is known to those of skill in the art, a chimeric antibody is produced by combining genetic material from a nonhuman source (for example but not limited to a mouse) with genetic material from a human. For example, and without wishing to be limiting, human constant domains can be fused to mouse $V_H$ and $V_L$ sequences (see Gonzales et al 2005). Veneering, also referred to in the art as "variable region resurfacing", of antibodies involves replacing solvent-exposed residues in the framework region of the native antibody or fragment thereof with the amino acid residues in their human counterpart (Padlan, 1991; Gonzales et al 2005); thus, buried non-humanized residues, which may be important for CDR conformation, are preserved while the potential for immunological reaction against solvent-exposed regions is minimized. Humanization of an antibody or antibody fragment comprises replacing an amino acid in the sequence with its human counterpart, as found in the human consensus sequence, without loss of antigen-binding ability or specificity; this approach reduces immunogenicity of the antibody or fragment thereof when introduced into human subjects. In this process, one or more than one of the CDR defined herein may be fused or grafted to a human variable region ($V_H$, or $V_L$), to other human antibody (IgA, IgD, IgE, IgG, and IgM), to human antibody fragment framework regions (Fv, scFv, Fab), or to human proteins of similar size and nature onto which CDR can be grafted (Nicaise et al, 2004). In such a case, the conformation of said one or more than one hypervariable loop is likely preserved, and the affinity and specificity of the sdAb for its target (i.e., *C. difficile* LTA) is likely minimally affected. As is known by those of skill in the art, it may be necessary to incorporate certain native amino acid residues into the human framework in order to retain binding and specificity. Humanization by CDR grafting is known in the art (for example, see Tsurushita et al, 2005; Jones et al, 1986; Tempest et al, 1991; Riechmann et al, 1988; Queen et al, 1989; all reviewed in Gonzales et al, 2005—see also references cited therein), and thus persons of skill would be amply familiar with methods of preparing such humanized antibody or fragments thereof.

The isolated or purified antibody or fragment thereof of the present invention may be a chimeric antibody or fragment thereof may comprise the $V_L$ and $V_H$ domains from mouse and framework regions (constant domains) from human IgG1, more specifically human kappa 1 light chain and human IgG1 heavy chain.

The antibody or fragment thereof of the present invention specifically binds to the influenza hemagglutinin (HA) protein. The hemagglutinin protein binds sialic acid present on the surface of target host cells and plays a key role in entry of the viral genome into the target cell. Currently, 18 types HA protein are known. The antibody or fragment thereof of the present invention may bind one subtype or multiple subtypes of HA; when binding multiple subtypes of HA, the antibody or fragment thereof may bind different subtypes with varying affinity.

The present application further provides a novel influenza HA antigen. The HA antigen comprises a peptide originating from the N-terminus of HA2, GLFGAIAGFIEGGW (SEQ ID NO:26) functionalized with O-beta-lactosyl-serine and its N-terminus and thio-Cys at its C-terminus; the C-terminus of the functionalized antigen is conjugated to Keyhole Limpet Hemocyanin (KLH), which is one of a plurality of carrier molecules that can be used for conjugating to antigenic epitope to provoke or increase the immune response thereof (such as, for example the tetanus toxin (TT)). The carrier protein, such as KLH in this case, may also comprises multiple epitopes conjugated to its surface. A schematic of the antigen is shown in FIG. 1A and in the following formula (I)

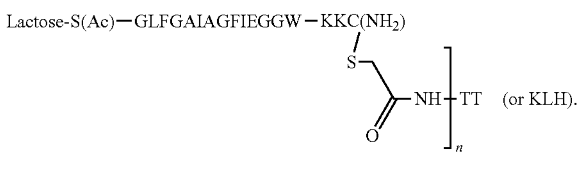

The antibody or fragment thereof of the present invention may bind to the novel antigen as described above.

The antibody or fragment thereof of the present invention may also comprise additional sequences to aid in expression, detection or purification of a recombinant antibody or fragment thereof. Any such sequences or tags known to those of skill in the art may be used. For example, and without wishing to be limiting, the antibody or fragment thereof may comprise a targeting or signal sequence, a detection/purification tag (for example, but not limited to c-Myc, Hiss, Hiss, or HissG), or a combination thereof. In another example, the signal peptide may be MVLQTQVFISLLLWISGAYG (SEQ ID NO.27) or MDWTWRILFLVAAATGTHA (SEQ ID NO.28). In a further example, the additional sequence may be a biotin recognition site such as that described by Cronan et al in WO 95/04069 or Voges et al in WO/2004/076670. As is also known to those of skill in the art, linker sequences may be used in conjunction with the additional sequences or tags, or may serve as a detection/purification tag.

The antibody or fragment thereof of the present invention may also be in a multivalent display format, also referred to herein as multivalent presentation. Multimerization may be achieved by any suitable method of known in the art. For example, and without wishing to be limiting in any manner, multimerization may be achieved using self-assembly molecules such as those described in WO2003/046560, where pentabodies are produced by expressing a fusion protein comprising the antibody or fragment thereof of the present invention and the pentamerization domain of the B-subunit of an ABs toxin family (Merritt & Hol, 1995). A multimer may also be formed using the multimerization domains described by Zhu et al. (2010); this form, referred to herein as a "combody" form, is a fusion of the antibody or fragment of the present invention with a coiled-coil peptide resulting in a multimeric molecule. Other forms of multivalent display are also encompassed by the present invention. For example, and without wishing to be limiting, the antibody or fragment thereof may be presented as a dimer, a trimer, or any other suitable oligomer. This may be achieved by methods known in the art, for example direct linking connection (Nielsen et al, 2000), c-jun/Fos interaction (de Kruif & Logtenberg, 1996), "Knob into holes" interaction (Ridgway et al, 1996).

Each subunit of the multimers described above may comprise the same or different antibodies or fragments thereof of the present invention, which may have the same or different specificity. Additionally, the multimerization domains may be linked to the antibody or antibody fragment using a linker, as required; such a linker should be of sufficient length and appropriate composition to provide flexible attachment of the two molecules, but should not hamper the antigen-binding properties of the antibody. For example, and without wishing to be limiting in any manner, the antibody or fragments thereof may be presented in a bi-specific antibody.

The invention also encompasses the antibody or fragment thereof as described above linked to a cargo molecule. The cargo molecule may be any suitable molecule. For example, and without wishing to be limiting in any manner, the cargo molecule may be a detectable agent, a therapeutic agent, a drug, a peptide, an enzyme, a growth factor, a cytokine, a receptor trap, an antibody or fragment thereof (e.g., IgG, scFv, Fab, $V_HH$, $V_H$, $V_L$, etc) a chemical compound, a carbohydrate moiety, DNA-based molecules (anti-sense oligonucleotide, microRNA, siRNA, plasmid), a neutralizing agent, viral vector (adeno-, lenti-, retro-), one or more liposomes or nanocarriers loaded with any of the previously recited types of cargo molecules, or one or more nanoparticle, nanowire, nanotube, or quantum dots. The antibody or fragment thereof may be linked to the cargo molecule using any method known in the art (recombinant technology, chemical conjugation, etc.).

In one non-limiting example, the cargo molecule may be a detectable label, a radioisotope, a paramagnetic label such as gadolinium or iron oxide, a fluorophore, a fluorescent agent, Near Infra-Red (NIR) fluorochrome or dye (such as Cy5.5), an echogenic microbubble, an affinity label (for example biotin, avidin, etc), a detectable protein-based molecule, nucleotide, quantum dot, nanoparticle, nanowire, or nanotube or any other suitable agent that may be detected by imaging methods. In a specific, non-limiting example, the anti-hemagglutinin or fragment thereof may be linked to a near infrared fluorescence (NIRF) imaging dye, for example and not wishing to be limiting Cy5.5, Alexa680, Dylight680, or Dylight800.

In another specific, non-limiting embodiment, the antibody or fragment thereof as described herein is linked to a drug, thus providing an antibody-drug conjugate (ADC). The drug may be any type of drug, for example but not limited to a neutralizing agent. The neutralizing agent may include, but is not limited to anti-microtubule agents (such as taxanes, maytansines and auristatins), DNA damaging agents (such as calicheamicin and duocarmydin), RNA polymerase inhibitors (such as alpha-amantin), and other potent neutralizing drugs (such as anthracyclines). As is known to those of skill in the art, the antibody-drug conjugate allows for targeted delivery of a drug, thus limiting systemic exposure. In this construct, the antibody or fragment thereof as described herein binds to the extracellular domain of hemagglutinin; the drug linked to the antibody or fragment thereof is thus internalized. Upon internalization DM1 is released within the target cells upon degradation of the human hemagglutininantibody-DM1 complex in lysosomes. Depending on the intracellular concentration of DM1 accumulated in cancer cells, rapid apoptosis occurs.

The cargo molecule as described herein may be linked, also referred to herein as "conjugated", to the antibody or fragment thereof by any suitable method known in the art. For example, and without wishing to be limiting, the cargo molecule may be linked to the peptide by a covalent bond or ionic interaction. The linkage may be achieved through a chemical cross-linking reaction, or through fusion using recombinant DNA methodology combined with any peptide expression system, such as bacteria, yeast or mammalian cell-based systems. When conjugating the cargo molecule to the antibody or fragment thereof, a suitable linker may be used. Methods for linking an antibody or fragment thereof to a cargo molecule such as a therapeutic or detectable agent would be well-known to a person of skill in the art.

The present invention also encompasses nucleic acid sequences encoding the molecules as described herein. Given the degeneracy of the genetic code, a number of nucleotide sequences would have the effect of encoding the desired polypeptide, as would be readily understood by a skilled artisan. The nucleic acid sequence may be codon-optimized for expression in various micro-organisms. The present invention also encompasses vectors comprising the nucleic acids as just described. Furthermore, the invention encompasses cells comprising the nucleic acid and/or vector as described.

The present invention further encompasses the isolated or purified antibody or fragments thereof immobilized onto a surface using various methodologies; for example, and without wishing to be limiting, the antibody or fragment may be linked or coupled to the surface via His-tag coupling, biotin binding, covalent binding, adsorption, and the like. Immobilization of the antibody or fragment thereof of the present invention may be useful in various applications for capturing, purifying or isolating proteins. The solid surface may be any suitable surface, for example, but not limited to the well surface of a microtiter plate, channels of surface plasmon resonance (SPR) sensorchips, membranes, beads (such as magnetic-based or sepharose-based beads or other chromatography resin), glass, plastic, stainless steel, a film, biosensors (such as those used in Biolayer Interferometry), or any other useful surface such as nanoparticles, nanowires and cantilever surfaces. A purified antibody or fragment thereof immobilized onto a surface may be used in a variety of methods, including diagnostic methods.

Thus, the present invention further provides an in vitro method of detecting influenza HA, comprising contacting a tissue sample with one or more than one isolated or purified antibody or fragment thereof of the present invention linked to a detectable agent. The HA-antibody complex can then be detected using detection and/or imaging technologies known in the art. The tissue sample in the method as just described may be any suitable tissue sample, for example but not limited to a serum sample, a vascular tissue sample such as lung tissue sample, neuroepithelium tissue sample, nasal aspirates, nasopharyngeal aspirates or swabs, nasal washes or swabs, throat swabs, endotracheal aspirates, bronchoalveolar lavage, or other tissue from the respiratory system; the tissue sample may be from a human or animal subject. The step of contacting is done under suitable conditions, known to those skilled in the art, for formation of a complex between the antibody or fragment thereof and HA. The step of detecting may be accomplished by any suitable method known in the art, for example, but not limited to optical imaging, immunohistochemistry, molecular diagnostic imaging, ELISA, or other suitable method. For example, and without wishing to be limiting in any manner, the isolated or purified antibody or fragment thereof linked to a detectable agent may be used in immunoassays (IA) including, but not limited to enzyme IA (EIA), ELISA, "rapid antigen capture", "rapid chromatographic IA", and "rapid EIA". (For example, see Planche et al, 2008; Sloan et al, 2008; Rüssmann et al, 2007; Musher et al, 2007; Turgeon et al, 2003; Fenner et al, 2008). Other immunoassay techniques in which the antibodies of the present invention may be used include Western blot, dot blot, and slot blot analysis. In a specific, non-limiting embodiment, the in vitro method is for detection of HA in nasal wash or swab. The one or more than one isolated or purified antibody or fragment thereof of the present invention could be used for detection in a Rapid Influenza Diagnosis Test (RIDT), also known as Point-of-Care Test (POCT) or dipsticks; these assays are used in the clinic to provide rapid diagnosis (less than 15 minutes) of patients with flu-like symptoms. The presence of viral antigens (HA) in a specimen (nasal wash or swab) is analysed in a lateral flow immunoassay and result in a colorimetric change when detected by the anti-HA antibodies.

The present invention also provides a method of preventing or treating influenza in a subject. The method comprises administering one or more than one isolated or purified antibody or fragment thereof as described herein to the subject. The one or more than one isolated or purified antibody or fragment thereof may be linked to one or more than one cargo molecule, as described herein. The subject may be a human or animal subject. The administration may be by any suitable method, for example parenteral administration, including but not limited to intravenous (iv), subcutaneous (sc), and intramuscular (im) administration.

The present invention also encompasses a composition comprising one or more than one isolated or purified antibody or fragment thereof as described herein. The composition may comprise a single antibody or fragment as described above, or may be a mixture of antibodies or fragments. Furthermore, in a composition comprising a mixture of antibodies or fragments of the present invention, the antibodies may have the same specificity, or may differ in their specificities; for example, and without wishing to be limiting in any manner, the composition may comprise antibodies or fragments thereof specific to hemagglutinin (same or different epitope). The composition may also comprise one or more than one antibody or fragments of the present invention linked to one or more than one cargo molecule.

The composition may also comprise a pharmaceutically acceptable diluent, excipient, or carrier. The diluent, excipient, or carrier may be any suitable diluent, excipient, or carrier known in the art, and must be compatible with other ingredients in the composition, with the method of delivery of the composition, and is not deleterious to the recipient of the composition. The composition may be in any suitable form; for example, the composition may be provided in suspension form, powder form (for example, but limited to lyophilised or encapsulated), capsule or tablet form. For example, and without wishing to be limiting, when the composition is provided in suspension form, the carrier may comprise water, saline, a suitable buffer, or additives to improve solubility and/or stability; reconstitution to produce the suspension is effected in a buffer at a suitable pH to ensure the viability of the antibody or fragment thereof. Dry powders may also include additives to improve stability and/or carriers to increase bulk/volume; for example, and without wishing to be limiting, the dry powder composition may comprise sucrose or trehalose. In a specific, non-limiting example, the composition may be so formulated as to deliver the antibody or fragment thereof to the gastrointestinal tract of the subject. Thus, the composition may comprise encapsulation, time-release, or other suitable technologies for delivery of the antibody or fragment thereof. It would be within the competency of a person of skill in the art to prepare suitable compositions comprising the present antibodies or fragments thereof.

The present invention further provides an isolated or purified antibody or fragment thereof as described herein for use in preventing or treating influenza in a subject.

The present invention also encompasses a cocktail comprising both mAbs 10A9 (SEQ ID NO. 35) and 11H12 (SEQ ID NO.36) for the detection, prevention or treatment of influenza.

The present invention further provides a kit for the identification of influenza in a sample, the kit comprising a support (such as nitrocellulose) and one or more than one isolated or purified antibody or fragment thereof as described herein. The one or more than one isolated or purified antibody or fragment thereof may be immobilized onto the nitrocellulose. The nitrocellulose support may be placed inside a plastic housing (also referred to herein as cassette), or may be adhered to a paper support (also referred to herein as card). The kit may also contain a swab for collecting the sample.

Particularly, the sample is a biological sample such as for example, blood, serum, nasal wash, nasal swab, saliva or sputum.

The present invention also provides a kit for the prevention or treatment of influenza in a subject, the kit comprising a container; and an isolated or purified antibody or fragment thereof contained therein. The kit may also contain a syringe for injecting the antibodies or fragments thereof to the subject.

The present invention will be further illustrated in the following examples. However, it is to be understood that these examples are for illustrative purposes only and should not be used to limit the scope of the present invention in any manner.

Example 1: Production and Purification of Antigen

A fusion peptide was prepared to use for immunization of mice. The fusion protein comprised a conserved peptide sequence from the N-terminal region of HA2 (GLFGAIAGFIEGGW; SEQ ID NO:26), functional groups on the peptide sequence, and keyhole limpet hemocyanin (KLH).

Figure 1A:
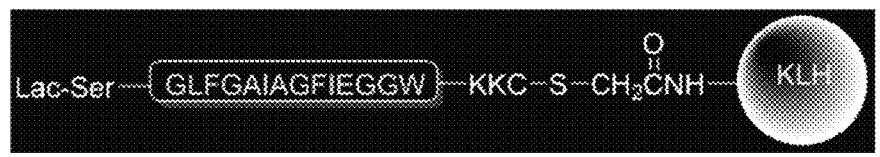
FIG. 1A is a schematic diagram of the conjugate structure used for mouse immunizations. The universal peptide epitope is shown in a box; Lac-Ser is 0-beta-lactosyl-serine; —S— is thio-Cys; KLH is Keyhole Limpet Hemocyanin.

Conjugate structure. The peptide conjugate shown in FIG. 1A, was designed by using a conserved peptide sequence at the N-terminus of HA2 that was previously identified: GLFGAIAGFIEGGW (SEQ ID NO:26). The peptide epitope was functionalized with lactose and conjugated to Keyhole Limpet Hemocyanin (KLH) to obtain a conjugate of formula (I):

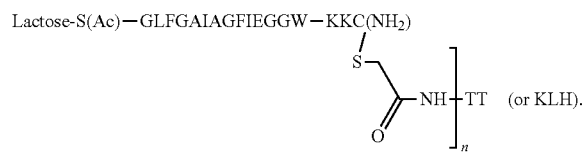

The KLH portion of the conjugate also comprised multiple epitopes conjugated to its surface.

Figure 1B:
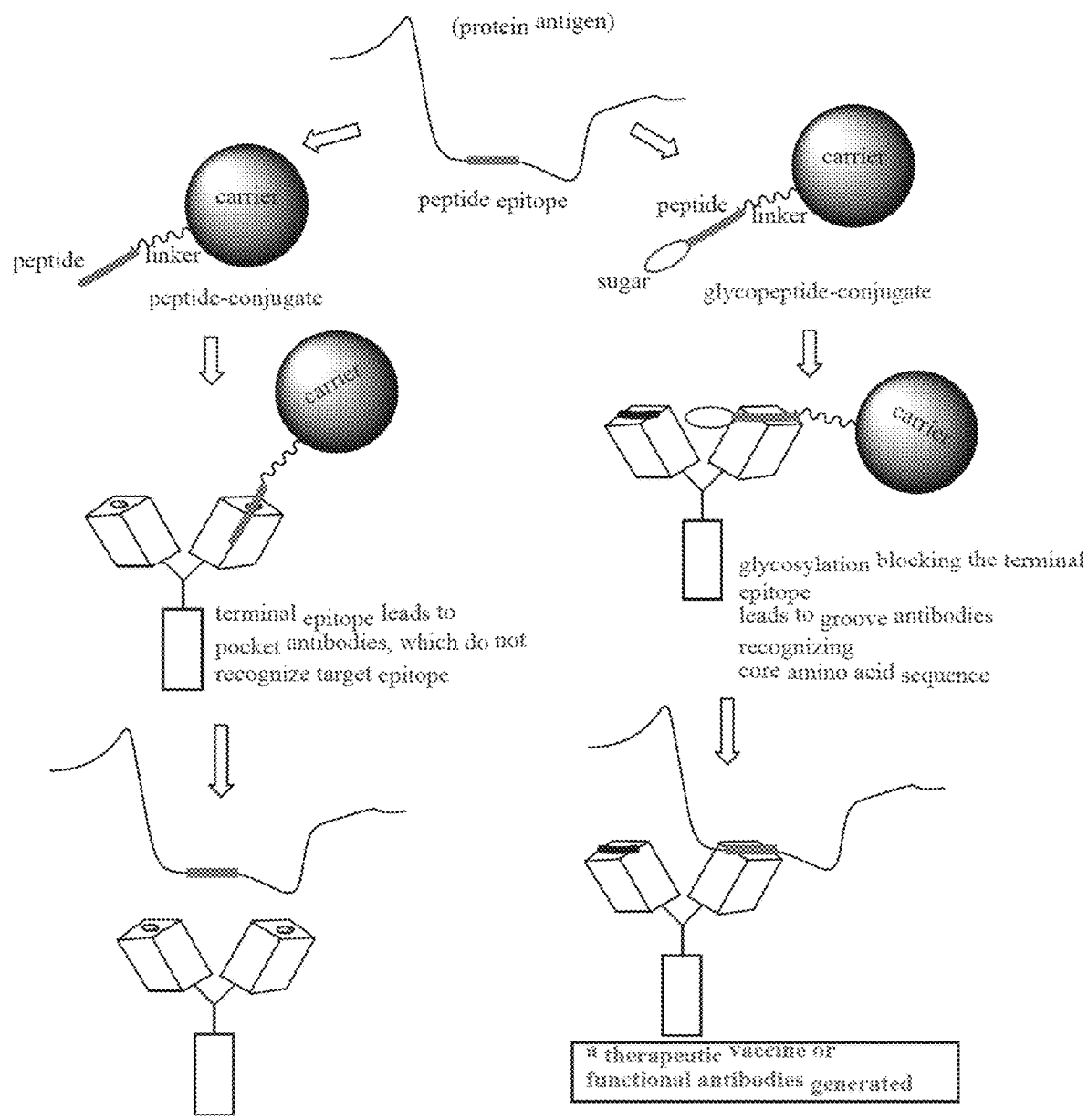
FIG. 1B is a scheme representing the addition of non-immunogenic hydrophilic saccharide at one end of a linear peptide-conjugate for producing the antibodies of the invention.

Peptide conjugate synthesis. The peptide conjugate was prepared according to FIG. 1B via a thio-ether bond between terminal Cys of the (glyco)peptide antigen and bromoacetyl KLH.

Bromoacetylation of KLH. Typically, 20 mg of KLH (Sigma-Aldrich H7017) was solubilized in 2 mL of deionized water at room temperature, and buffer-exchanged to 10 x PBS by an Amicon Ultra centrifugal filter (MWC 30K). To the above solution of KLH in 10 X PBS (2 mL) was added 9 mg of bromoacetic acid N-hydroxysuccinimide ester in DMSO (0.18 mL) and incubated overnight at 4° C. The product was purified by a G-25 column (50×1.6 cm) with PBS as eluent and bromoacetyl KLH obtained was stored in PBS buffer. Similarly, bromoacetyl BSA was also made in parallel and MALDI indicated 9-10 bromoacetyl groups per BSA, we obtained similar ratio of bromoacetyl group present in KLH.

Conjugation: (glyco)peptide antigen with terminal Cys and bromoacetyl KLH are dissolved under the conditions of 0.1M phosphate buffer with 5 mM EDTA-0.01% sodium azide at pH 8.0-8.5 overnight at room temperature. As a reference to estimate the peptide antigen on KLH, bromoacetyl BSA was also coupled with the peptide to give a conjugate with a ratio of peptide:BSA 6-7:1. The peptide antigen coupled to KLH carrier protein was found to have a similar w/w ratio as BSA.

Purification. Typically, a (glyco)peptide antigen with terminal Cys was mixed with equivalent amount of biotin-maleimide (B1267, Sigma), in DMSO at room temperature and the solution was kept for 5 hours, which was diluted with water and lyophilized to give product. The product was characterized by MALDI and no further purification was needed for ELISA.

Example 2: Generation of Anti-Influenza Antibodies

To produce antibodies that target the influenza virus, mice were immunized with the peptide conjugate obtained in Example 1. Hybridomas (monoclonal antibodies) were also prepared and evaluated by ELISA.

Immunizations. 6-week old A/J mice were bled (pre-immune serum) and immunized i.p. and s.c. with 100 μg of antigen (Example 1) in Titermax adjuvant. Three weeks later, a second injection of 100 μg of antigen in Titermax adjuvant was performed and mice were bled 7-10 days later. The serum titer was measured by ELISA. Two months later, a final i.p. booster injection using 100 μg of antigen was performed 4 days prior to fusion experiment.

Fusion of the harvested spleen cells. All manipulations were carried out under sterile conditions. Spleen cells were harvested from immunized mice in IMDM (Hy-Clone) and fused to NS0 myeloma cell line using PEG fusion protocol. To this end, spleen cells and myeloma cells were washed in IMDM, counted in RBC lysing buffer (Sigma) and mixed together at a 5:1 ratio. Pelleted cells were fused together by adding 1 ml of a 50% solution of PEG 4000 (EMD-Millipore) in PBS preheated at 37° C. drop-wise over one minute, and incubated at 37° C. for an additional 90 sec. The reaction was stopped by addition of 30 ml of IMDM at 22° C. over 2 min. After a 10 min incubation, freshly fused cells were spun at 233×g for 10 min. Cells were washed once in IMDM supplemented with 10% heat inactivated FBS (Sigma), and suspended at a concentration of $2\times10^5$ input myeloma cells per ml in HAT selection medium (IMDM containing 20% heat inactivated FBS, penicillin-streptomycin (Sigma), 1 ng/ml mouse IL-6 (Biosource), HAT media supplement (Sigma) and L-glutamine) and incubated at 37° C., 5% $CO_2$. The next day, hybridoma cells were washed and suspended at a concentration of $2\times10^5$ input myeloma cells per ml in semi-solid medium D (StemCell) supplemented with 5% heat inactivated FBS, 1 ng/ml mouse IL-6 and 10 μg/ml FITC-Fab'2 Goat anti-mouse IgG (H+L) (Jackson). The cell mixture was plated in OmniTrays (Nunc) and further incubated for 6-7 days at 37° C., 5% $CO_2$. Secretor clones were then transferred using a mammalian cell clone picker (ClonepixFL, Molecular Devices) into sterile 96-well plates (Costar) containing 200 µl of IMDM supplemented with 20% heat inactivated FBS, penicillin-streptomycin (Sigma), 1 ng/ml mouse IL-6 (Biosource), HT media supplement (Sigma) and L-glutamine and incubated for 2-3 days at 37° C., 5% $CO_2$.

Hybridoma selection. Hybridoma supernatant were screened by ELISA to detect specific binders. To this end, 96-well half-area plates (Costar) were coated with 25 µl of neutravidinat 10 µg/ml in 50 mM carbonate buffer at pH9.8 and incubated 2 hours at room temperature. Microplates were washed 3 times with PBS, blocked with PBS-BSA 1%, washed once with PBS and 25 µl of biotinylated peptide at 5 µg/ml was added and incubated overnight at 4° C. Microplates were washed 4 times with PBS-Tween 20 0.05% and 25 µl of hybridoma supernatant were added and incubated at 37° C., 5% $CO_2$ for 2 hours. Plates were washed 4 times with PBS-Tween 20 0.05% and incubated for 1h at 37° C., 5% $CO_2$ with 25 µl of secondary antibody alkaline phosphatase conjugated F(ab)'$_2$ goat anti-mouse IgG (Fcγ fragment specific) (Jackson Immunoresearch) diluted 1/000 in blocking buffer. After 4 washes with PBS-Tween 20 0.05%, 25 µl of a 1 mg/ml pNPP substrate solution was added and further incubated for one hour at 37° C. $OD_{405nm}$ measurements were taken using a microplate reader (Spectramax 340 PC, Molecular Devices).

From fusions of mouse spleen cells, anti-influenza mAb-producing hybridomas were identified, from which conditioned medium (CM) was collected and evaluated for binding to the peptide (Example 1) by ELISA. Results for the selected clones are shown in Table 1.

TABLE 1

Evaluation of the CM collected from mAb-producing hybridomas by ELISA.

| Clone | Species | Isotype | ELISA on peptide |
|---|---|---|---|
| F211-11H12 | mouse | IgG2A, κ | +++ |
| F211-9D1 | mouse | IgG2A, κ | +++ |
| F211-10A9 | mouse | IgG2A, κ | +++ |

All mAbs were then purified via Protein A spin column, dialyzed twice against PBS and concentrated using an Amicon filter (cut-off MW 30,000). The final concentration of the antibody solutions was determined by nano-drop (280 nm). Clones 11H12, 9D1 and 10A9 were subsequently sequenced using art-known methods.

Sequences are as follows:

11H12 light chain:
(SEQ ID NO: 23)
DIVMSQSPSSLAVSVGEKVTMSCKSSQSLLNSRNQKNHLAWYQQKPGQSP

KLLIYWASTRESGVPDRFTGDGSGTDFTLTISSVKAEDLAVYYCQQYYTY

RTFGGGTKLEIK;

11H12 heavy chain:
(SEQ ID NO: 25)
DVQLQESGPGLVKPSQSLSLTCSVTGYSITSDYYWNWIRQFPGNKLEWMA

YIGYDGTKNYNPSLKNRISITRDTSKNQFFLKLNSVTTDDTATYYCTRDR

ANWDDYFDYWGQGTTLTVSS.

10A9 light chain:
(SEQ ID NO: 19)
DIVMTQSPSSLAMSVGQKVTMSCKSSQSLLNSDTQKNFLAWYQQKPGQSP

KILVYFASTKESGVPDRFIGSGSGTDFTLTITSVQAEDLADYFCQQYYSI

PLTFGAGTKLELK;

10A9 heavy chain:
(SEQ ID NO: 21)
QIQLQQSGPELVKPGAPVKISCKASGYTFTDYYIHWVNQRPGQGLEWIGY

IYPGNGHTVYNQKFKVRATLTADNPSSTAYLQLNSLTSEDSGVYFCAYDL

FNYWGQGTLVTVSA.

9D1 light chain:
(SEQ ID NO: 22)
DIVMSQSPSSLAVSVGEKVTMSCKSSQSLLNSRNQKNHLAWYQQKPGQSP

KLLIYWASTRESGVPDRFSGDGSGTDFTLTISSVKAEDLAVYYCQQYYTY

RTFGGGTKLEIK;

9D1 heavy chain:
(SEQ ID NO: 24)
DVQLQESGPGLVKPSQSLSLTCSVTGYSITSDYYWNWIRQFPGNKLEWMA

YIGYDGSKNYNPSLKNRISITRDTSKNQFFLKLNSVTTDDTATYYCTRDR

ANWDDYFDYWGQGTTLTVSS.

Figure 2A:
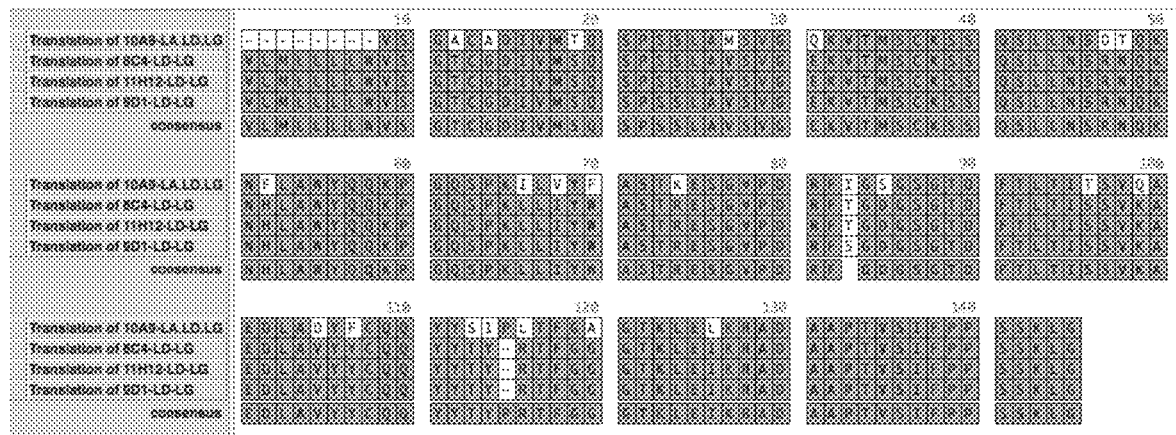
FIGS. 2A-2B are sequence alignments of the variable domains of the antibodies of the present application.
Figure 2B:
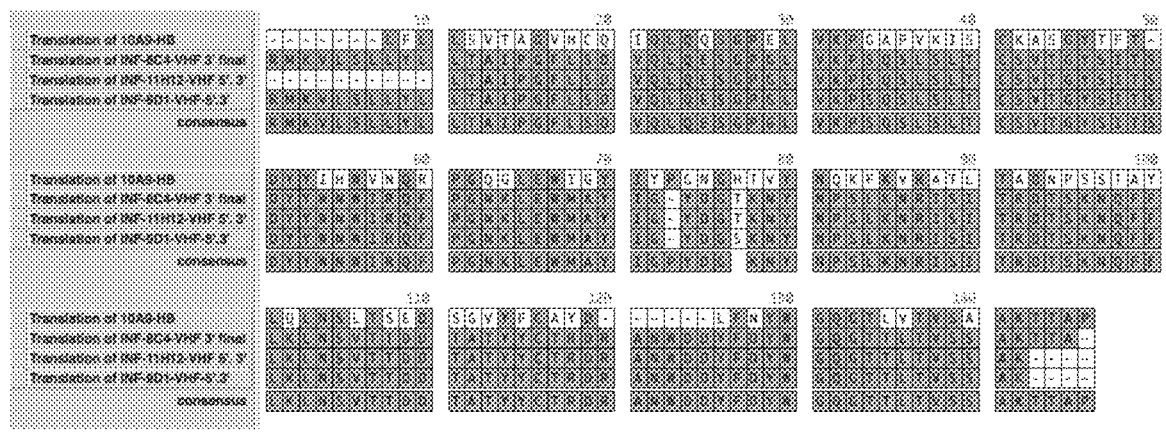

FIG. 2 show the sequence alignments of the variable domains of the 11H12, 9D1 and 10A9 antibodies.

Example 3: Biophysical Characterization of the Anti-HA mAb

The anti-HA mAb of Example 2 were characterized using Differential Scanning calorimetry (DSC) and surface plasmon resonance (SPR). MAb resistance to freeze-thaw cycles were also evaluated.

Figure 3:
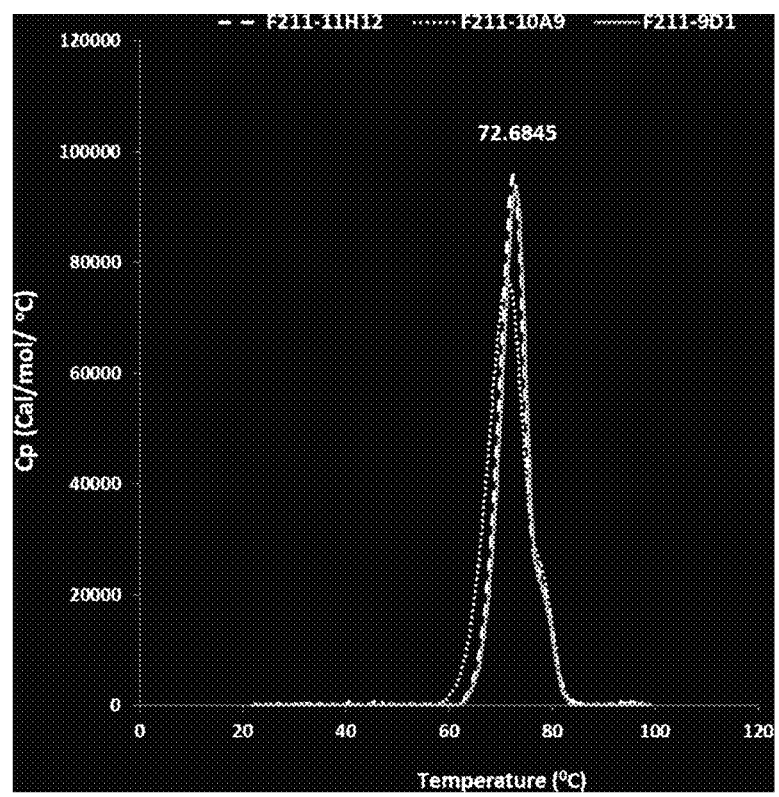
FIG. 3 shows thermograms obtained by Differential Scanning calorimetry (DSC) of the three mAb. Each mAb was scanned from 20 to 100° C.

Thermal stability of the mAb measured by DSC: The mAb were analysed by DSC to determine at which temperature unfolding of the mAb is induced. Each purified mAb was diluted to 0.4 mg/mL in PBS, and a total of 400 uL was used for DSC analysis with a VP-Capillary DSC (Malvern Inc.). At the start of each DSC run, 5 buffer blank injections are performed to stabilize the baseline and a buffer injection precede each mAb injection for referencing. Each sample was scanned from 20 to 100° C. at a 60° C./hr rate, with low feedback, 8 sec filter, 5 min preTstat, and 70 psi nitrogen pressure. The mAb thermograms were referenced and analyzed using Origin 7 software. The melting points of the mAb were found to be between 71.28 and 72.90° C. as reported in Table 2. Thermograms are also shown in FIG. 3.

TABLE 2

Melting points (TM) measured by DSC for each of the 3 mAb

| Sample | Tm (melting point in ° C.) |
|---|---|
| F211-11H12 | 72.68 |
| F211-10A9 | 71.28 |
| F211-9D1 | 72.90 |

Surface Plasmon Resonance (SPR). The binding of the peptide of Example 1 to captured antibody (9D1, 10A9 or 11H12) was determined by SPR using a BIACORE T200 (GE Healthcare) using PBS containing 0.05% Tween 20 (Teknova Inc.) and 3.4 mM EDTA as a running buffer. An anti-mouse-Fc surface was immobilized to approximately 2200 RUs using the Immobilization Wizard within the T200 control software set to a 2000 RU target. Standard amine coupling of 20 ug/mL anti-mouse Fc solution in 10 mM NaOAc pH 4.5 was used. For the binding assay, approximately 350 RUs of antibody to be tested (9D1, 10A9 or 11H12) was captured onto a sheep anti-mouse Fc antibody surface by injecting 20 ug/mL solution for 300 seconds. This was followed by single cycle kinetics injection of peptide using a 2-fold dilution series with a top-nominal concentration of 250 nM for antibody 9D1 and 11H2, and 15 nM for antibody 10A9, or PBST running buffer only for referencing. 180 second injections of each peptide or buffer blank were used at a flow rate of 100 uL/min and with a 2700 second dissociation. Surfaces were regenerated with 10 mM glycine pH 1.5 with a contact time of 120 seconds. Sensorgrams were double referenced and data were analyzed within Biacore T200 evaluation software v3.0 (GE Healthcare). Results of binding affinity for each mAb are shown in Table 3.

TABLE 3

Binding affinity measured by surface plasmon resonance for each of the mAb.

| mAb | KD (M) |
|---|---|
| F211-9D1-2 | $3.93 \times 10^{-10}$ |
| F211-10A9-2 | $3.38 \times 10^{-10}$ |
| F211-11H12-3 | $4.65 \times 10^{-10}$ |

Figure 4A:
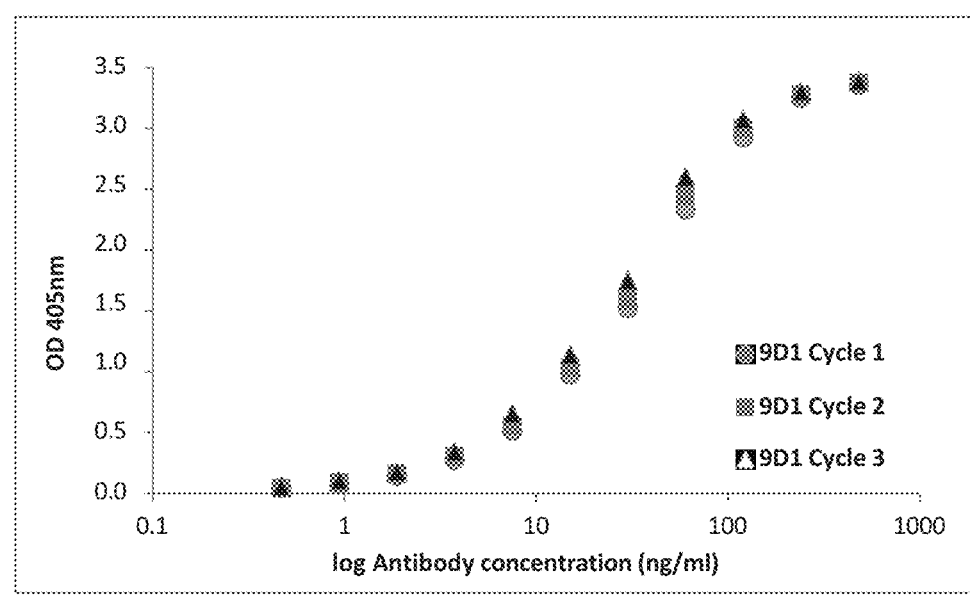
FIGS. 4A-4C show results from ELISA analysis following one to three freeze-thaw cycles. The binding affinity of 9D1 (FIG. 4A), 10A9 (FIG. 4B) and 11H12 (FIG. 4C) was measured using the peptide-conjugate shown in FIG. 1.
Figure 4B:
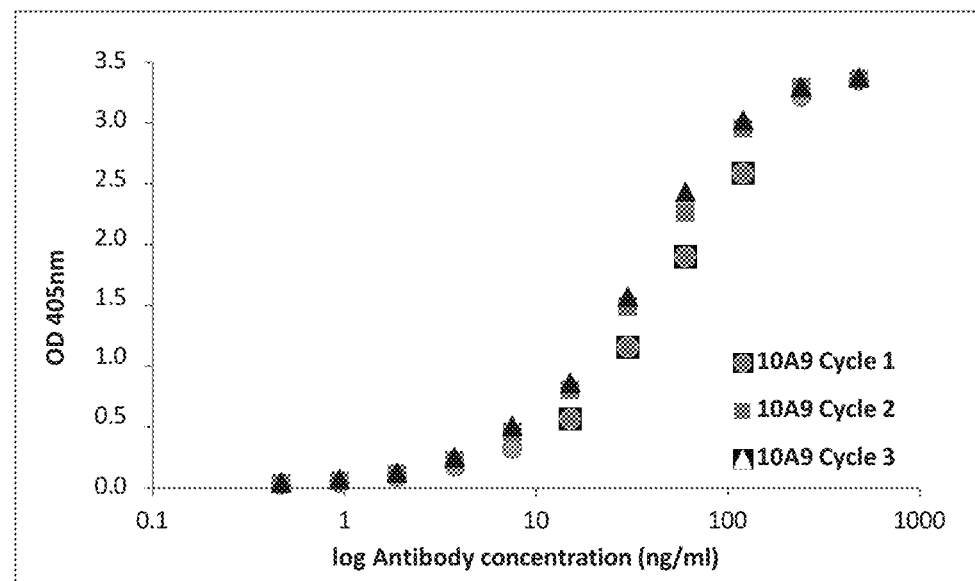
Figure 4C:
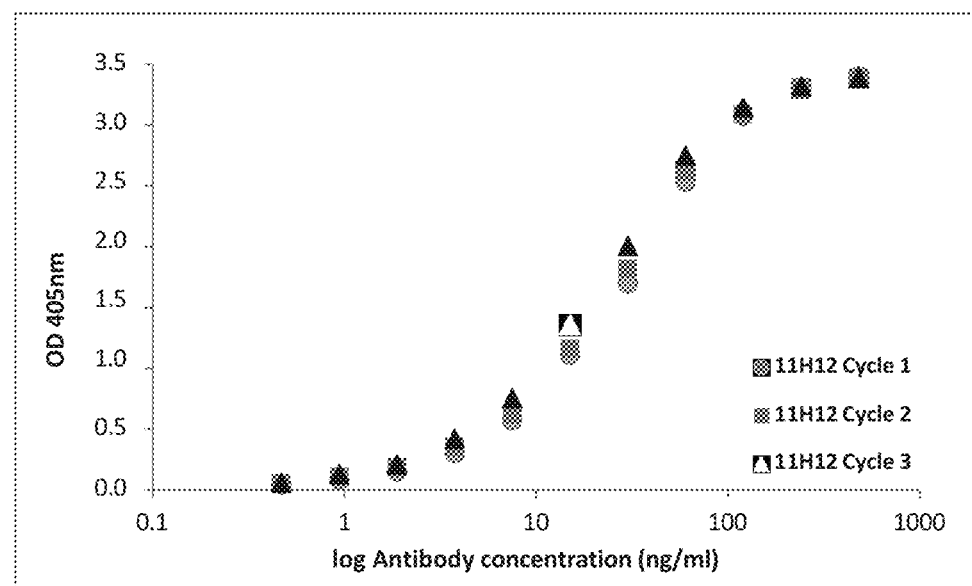

Resistance to freeze-thaw cycles measured by ELISA. The binding affinity of the three mAb following 1, 2 and 3 freeze-thaw cycles was assessed by ELISA. The freeze-thaw cycles were performed by freezing the mAb at −80° C. and thawing at room temperature 1 to 3 times; the mAb were kept at 4° C. after the last thaw. Plates were coated with 1 μg/ml peptide-conjugate (Example 1) overnight at 4° C. After washing, the mAb were serially diluted and added to the plate in concentrations ranging from 2 to 480 ng/ml. AP-conjugated secondary antibodies and p-nitrophenyl phosphate tablets were used for detection. Results shown in FIG. 4 indicate that 1 to 3 freeze-thaw cycles have no detrimental effect on the binding affinity to the peptide-conjugate. KD values are summarized in Table 4.

TABLE 4

KD values obtained after 1 to 3 freeze-thaw cycles with the 4 mAb

| | Cycle 1 | Cycle 2 | Cycle 3 |
|---|---|---|---|
| F211-8C4-2 | $3.25 \times 10^{-8}$ | $2.28 \times 10^{-8}$ | $2.50 \times 10^{-8}$ |
| F211-9D1-2 | $3.57 \times 10^{-8}$ | $3.28 \times 10^{-8}$ | $2.81 \times 10^{-8}$ |
| F211-10A9-2 | $5.62 \times 10^{-8}$ | $3.79 \times 10^{-8}$ | $3.38 \times 10^{-8}$ |
| F211-11H12-3 | $2.98 \times 10^{-8}$ | $2.67 \times 10^{-8}$ | $2.22 \times 10^{-8}$ |

Example 4: Immunoreactivity of Anti-Influenza mAb

The immunoreactivity of the anti-influenza monoclonal antibodies obtained in Example 2 was assessed by Western blot using recombinant HA proteins and viruses. Dot blot assays to determine reactivity of the mAb with multiple strains were also performed.

Western blot using recombinant protein. Four recombinant HA (rHA) proteins from influenza strains were tested:

H5N1/A/Indonesia/05/2005 (Protein Sciences)
H1N1 A/Puerto Rico/08/1934 (Protein Sciences)
B/Brisbane/60/2008 (Protein Sciences)
H7N7/A/Netherlands/219/2003 (Protein Sciences)

The rHA were used to assess the specificity of the monoclonal antibodies of Example 2. The rHA were heat-denatured at 95° C. for 10 min, resolved on a 4-15% gel and transferred to a nitrocellulose membrane. The membranes were blocked in 5% milk and probed overnight at 4° C. with purified primary antibodies (11H12; 10A9, 9D1; anti-GFP negative control) at 2 µg/mL or hybridoma supernatant diluted 1 in 5. Membranes were washed and incubated with infrared-conjugated secondary antibodies and scanned using an Odyssey scanner (LICOR Biosciences, Lincoln, Nebr.). Results of the Western blot analysis are shown in FIG. 5. 11H12 and 9D1 recognized H5N1/A/Indonesia/05/200, H1N1 A/Puerto Rico/08/1934, and B/Brisbane/60/2008. Only the 10A9 mAb recognized the rHA from H7N7/A/Netherlands/219/2003; however, it did not recognize any other rHA. Identical results were obtained from the hybridoma supernatant and purified mAb for each clone, indicating that the purification process did not affect the integrity of the antibodies.

The Western blot analysis was repeated and expanded using the following rHA proteins:

H1N1/A/California/06/2008 (Immune Technology);
H3N2/A/Brisbane/10/2007 (BEI Resources);
H5N1/A/Indonesia/05/2005 (Protein Sciences);
H5N1/A/Vietnam/1203/2004 (Protein Sciences);
H7N7/A/Netherlands/219/2003 (Protein Sciences);
H9N2/A/HongKong/1073/1999 (Protein Sciences); or
B/Brisbane/60/2008 (Protein Sciences).

In this assay, 300 ng rHA were heat-denatured at 95° C. for 10 min in sample buffer (20% SDS), loaded on a 4-15% gel, resolved by SDS-PAGE, and transferred on a nitrocellulose membrane. The membranes were blocked in 5% non-fat milk and further incubated with 2 µg/ml primary antibodies overnight at 4° C. The membranes were probed with either the purified mAb (11H12; 10A9; anti-GFP) or a mixture of 11H12 and 10A9 antibodies. Membranes were washed and incubated with infrared-conjugated secondary antibodies at a dilution of 1:15000, and scanned using an Odyssey scanner (LICOR Biosciences, Lincoln, Nebr.). Results are shown in FIG. 6 and Table 5.

TABLE 5

Reactivity of antibodies with rHA proteins.

| Lane | rHA | 11H12 | 10A9 | Both mAb | Anti-GFP |
|---|---|---|---|---|---|
| 1 | H1N1 A/California/06/2008 | + | ++ | +++ | − |
| 2 | H3N2/A/Brisbane/10/2007 | − | ++ | +++ | − |
| 3 | H5N1 A/Indonesia/05/2005 | +++ | + | +++ | − |
| 4 | H5N1/A/Vietnam/1203/2004 | +++ | + | +++ | − |
| 5 | H7N7/A/Netherlands/219/2003 | − | +++ | +++ | − |
| 6 | H9N2/A/Hong Kong/1073/1999 | + | − | ++ | − |
| 7 | B/Brisbane/60/2008 | +++ | − | +++ | − |

"Lane" refers to the lane on the Western blot shown in FIG. 6.
"+++" indicates that the strain was highly detected by the specified antibody, "++" indicates that the strain was well detected by the specified antibody, "+" indicates that the strain was weakly detected by the specified antibody, while "−" indicates that the strain was not detected by the antibody.

In agreement with the previous Western blot analysis, only the 10A9 mAb recognized the H7N7/A/Netherlands and H3N2/A/Brisbane. 11H12 consistently recognized all other rHA. Use of a cocktail containing both mAb resulted in the detection of all 7 rHA demonstrating that there is no negative interactions (competition) when the mAb are combined. Thus, the antibodies can be used together in a cocktail.

Western blot using viruses. Thirty strains of influenza virus (see Table 6) were produced in eggs or mammalian cells using art-known methods (Chun et al., 2008). Samples were heat-denatured at 95° C. for 10 min, loaded and electrophoresed on a 4-15% gel then transferred to a nitrocellulose membrane. The membranes were blocked in 5% milk and probed with primary antibodies overnight at 4° C. at a concentration of 2 µg/ml. Membranes were next incubated with HRP-conjugated secondary antibodies and signal was revealed by chemiluminescence. Representative results with strains belonging to 13 different HA subtypes are shown in FIG. 7. Results obtained from 40 strains produced using different platforms tested are summarized in Table 6. All of the influenza virus HA subtypes were recognized by at least one of mAb 11H12 or 10A9 demonstrating the universality of the antibodies. In addition, the mAb are able to detect HA from viruses produced in eggs as well as mammalian cells (Table 6).

TABLE 6

Reactivity of antibodies with 40 different influenza strains.

| Strain | Type of Ag | Production platform | 11H12 | 10A9 |
|---|---|---|---|---|
| H1N1 A/Puerto Rico/8/1934 | rHA | Insect cells | Yes | No |
|  | Virus | Eggs | Yes | Yes |
|  | Virus | MDCK cells | Yes | Yes |
|  | Virus | HEK293 cells | Yes | Yes |
|  | VLP | HEK293 cells | Yes | Yes |
| H1N1 A/California/07/2009 | rHA | Insect cells | Yes | Yes |
|  | Virus | Egg | Yes | Yes (low signal) |
|  | Virus | MDCK | Yes | Yes (low signal) |
|  | Virus | HEK293 | Yes | Yes (low signal) |
|  | Virus | Avian | Yes | No |
|  | VLP | Plant | Yes | Yes |
| H1N1 A/Wilson Smith/33 | Virus | HEK293 cells | Yes | No |
| H1N1 Avian like Swine | Virus | MDCK cells | Yes | Yes |
| H1N2 Reassortant human like A/Scotland/410440/94 | Virus | MDCK cells | Yes | Yes |
| H2N2 A/Singapore/1/57 | Virus | Eggs | Yes | Yes |
| H3N1 A/Victoria/361/2011 | VLP | Plant | No | Yes |
| H3N2 A/Wisconsin/67/2005 [2] | rHA | Insect cells | Yes | Yes |
| H3N2 A/Aichi/2/1968 [2] | Virus | HEK293 cells | Yes | Yes |
| H3N2 A/Hong Kong/8/1968 [2] | Virus | HEK293 cells | Yes | Yes |
| H3N2 A/Brisbane/10/2007 | rHA | Insect cells | No | Yes |
| H3N2 A/New York/55/01 | Virus | Eggs | Yes | Yes |
| H3N2 A/Texas/50/2012 | Virus | HEK293 | Yes | Yes (low signal) |
| H3N2 A/Panama/2007/99 | Virus | Egg | Yes | Yes |
| H4N6 A/Duck/Czechoslovakia/56 | Virus | Eggs | No | Yes |
| H5N1 A/Vietnam/1203/2004 | rHA | Insect cells | Yes | No |
| H5N1 A/Indonesia/5/2005 | rHA | Insect cells | Yes | No |
|  | VLP | Plant | Yes | Yes |
| H5N2 A/Finch/England | Virus | MDCK cells | Yes | Yes |
| H5N9 A/Turkey/Wisconsin/68 | Virus | Eggs | Yes | Yes |
| H6N2 A/Turkey/Massachusetts/3740/65 | Virus | Eggs | Yes | Yes |
| H7N7 A/Netherlands/219/2003 | rHA | Insect cells | No | Yes |
| H7N7 A/Equine/Prague/1/56 | Virus | Eggs | Yes | Yes |
| H7N9 A/Anhui/1/2013 | rHA | Human cells | No | Yes |
| H7N9 A/Shanghai/2/2013 | rHA | Human cells | No | Yes |
| H7N9 A/Pigeon/Shanghai/S1069/2013 | rHA | Human cells | No | Yes |
| H7N1 A/Turkey/Italy/977/1999 | Virus | MDCK cells | Yes | Yes |
| H7N3/A/Turkey/Oregon/71 | Virus | Eggs | No | Yes |
| H8N4 A/Turkey/Ontario/6118/68 | Virus | Eggs | Yes | Yes |
| H9N2 A/Hong Kong/1073/1999 | rHA | Insect cells | Yes | No |
| H9N2 A/Turkey/Wisconsin/1/66 | Virus | Eggs | Yes | Yes |
| H10N8 A/Quail/Italy/1117/65 | Virus | Eggs | Yes | Yes |
| H11N6 A/Duck/England/56 | Virus | Eggs | Yes | Yes |
| H12N6 A/Duck/Wisconsin/480/79 | Virus | Eggs | Yes | Yes |
| H12N5 A/Duck/Alberta/60/76 | Virus | MDCK cells | Yes | Yes |
| H13N6 A/Gull/Maryland/704/77 | Virus | Eggs | Yes | Yes |
| B/Malaysia/2506/2004 | Virus | Eggs | Yes | No |
| B/Brisbane/60/2008 | rHA | Insect cells | Yes | No |
| B/Lee/40 | Virus | HEK293 cells | Yes | No |
| B/Massachusetts/2/2012 | Virus | MDCK | Yes | Yes (low signal) |
|  | Virus | HEK293 | Yes | Yes (low signal) |
| B/Florida/04/2006 | Virus | MDCK cells | Yes | Yes |
|  | Virus | Egg | Yes | Yes |

"Yes" indicates that the strain was detected by the specified antibody, while "No" indicates that it was not.

Dot blot using rHA and viruses. Detection of 19 strains belonging to 6 different HA subtypes was also assessed by dot blot. Representative results are shown in FIGS. 8A-C. Labels at the bottom right of each dot correspond to the strain listed in Table 7. As opposed to Western blot analysis where samples are fully denatured with SDS, samples detected by dot blot are mildly denatured with 4M urea for 30 min according to Li et al, 2010. The samples are then placed in a dot blot apparatus and fixed onto a nitrocellulose membrane by applying vacuum. The membranes were blocked in 5% milk and probed overnight at 4° C. with purified primary antibodies (11H12; 10A9, 9D1) at 6 µg/mL. Membranes were washed and incubated with infrared-conjugated secondary antibodies and scanned using an Odyssey scanner (LICOR Biosciences, Lincoln, Nebr.).

establish a standard curve ranging from 160 ng/mL to 20 µg/mL HA. The linear portion of the curve was used to generate an equation of the type y=ax+b (FIG. 9B). Using this equation, six samples were quantified. Samples were run on the same blot at four different dilutions (FIG. 9C) to ensure that they fall within the dynamic range of the standard curve. Samples 1 to 5 were produced by infecting HEK293 cells with H1N1 A/Puerto Rico/8/34 at an MOI of 0.01 and collecting the supernatant. Sample 6 was collected from non-infected cells and was used as a negative control. This example shows that the mAb can be used in conjunction with a dot blot apparatus to quantify viruses given that the appropriate standard is used.

Direct ELISA. Recombinant HA from H5N1 A/Indonesia/05/2005 (Protein Science) was denatured in 8M urea supple-

TABLE 7

List of the strains tested by dot blot (FIG. 8) with mAb 9D1, 10A9 and 11H12, and signal intensity obtained with each mAb (arbitrary fluorescent units)

| Label (FIG. 8) | Type of Antigen | Production platform/Company | Strain full name | 9D1 | 10A9 | 11H12 |
|---|---|---|---|---|---|---|
| 1 | rHA | Prot. Sc.[1] | H1N1 A/puerto rico/8/34 | 21363 | 2522 | 20304 |
| 2 | rHA | Imm. Techn.[2] | H1N1 A/California/06/2008 | 5778 | 2782 | 5119 |
| 3 | rHA | Sino Biol.[3] | H3N2 A/Aichi/2/1968 | 842 | 18095 | 995 |
| 4 | rHA | Prot. Sc.[1] | H3N2 A/Wisconsin67/05 | 70 | 791 | 176 |
| 5 | rHA | Imm. Techn.[2] | H3N2 A/Hong Kong/8/68 | 651 | 5668 | 464 |
| 6 | rHA | BEI Res.[4] | H3N2/A/Brisbane/10/2007 | 362 | 11515 | 280 |
| 7 | rHA | Prot. Sc.[1] | H5N1 A/Indonesia/05/2005 | 10080 | 165 | 22168 |
| 8 | rHA | Prot. Sc.[1] | H5N1/A/Vietnam/1203/2004 | 46752 | 8262 | 45928 |
| 9 | rHA | Prot. Sc.[1] | H7N7/A/Netherlands/219/2003 | 425 | 42049 | 488 |
| 11 | rHA | Prot. Sc.[1] | B/Brisbane/60/2008 | 41083 | 25825 | 38483 |
| 10 | rHA | Prot. Sc.[1] | H9N2/A/HongKong/1073/1999 | 3759 | 2969 | 3573 |
| 12 | Inactivated virus | Egg/NIBSC[5] | H1N1 A/California/06/2008 | 17370 | 227 | 14413 |
| 13 | Inactivated virus | Egg/NIBSC[5] | H3N2/A/Texas | 238 | 412 | 201 |
| 14 | Inactivated virus | Egg/NIBSC[5] | B/Massachusetts | 10499 | 240 | 9927 |
| 15 | Negative ctrl | NRC[6] | Buffer only | 93 | 43 | 91 |
| 16 | Negative ctrl | NRC[6] | Non-related protein | 47 | 34 | 38 |
| 17 | virus | HEK293/NRC[6] | H1N1 A/puerto rico/8/34 | 7808 | 7451 | 6537 |
| 18 | virus | HEK293/NRC[6] | H1N1 A/Wilson Smith/33 | 6006 | 343 | 5057 |
| 19 | virus | HEK293/NRC[6] | H3N2 A/Hong Kong/8/68 | 108 | 319 | 201 |
| 20 | virus | HEK293/NRC[6] | H3N2 A/Aichi/2/1968 | 231 | 833 | 341 |
| 21 | virus | HEK293/NRC[6] | B/Lee | 7195 | 1054 | 6423 |
| 22 | VLP | Plant/MedG[7] | H3N1/A/Victoria/361/2011 | 4292 | 34000 | 3695 |
| 23 | VLP | Plant/MedG[7] | H5N1 A/Indonesia/05/2005 | 46669 | 28633 | 43052 |
| 24 | VLP | Plant/MedG[7] | H1N1 A/California/06/2008 | 55423 | 55141 | 54122 |

[1]Prot. Sc: Protein Sciences;
[2]Imm. Techn: Immune Technology;
[3]Sino Biol.: Sino Biologicals;
[4]BEI Ress.: BEI Resources;
[5]NIBSC: The National Institute for Biological Standards and Control.
[6]NRC: National Research Council Canada;
[7]MedG: Medicago Inc.

The specificity of the antibodies is illustrated by the lack of signal with the negative controls (dots number 15 and 16). Overall, mAb 10A9 has a higher binding affinity for strains of subtype H3 (dots 3-6) and H7 (dot 9) whereas mAb 11H12 and 9D1 have a higher binding affinity for strains of subtype H1 (dots 1-2, 12 and 16) and H5 (dots 7-8).

Example 5: Quantification of HA by Dot-Blot and ELISA

The anti-HA monoclonal antibodies obtained in Example 2 were used to quantify viruses by dot blot, and rHA by ELISA.

Dot blot for quantification. Following the same denaturation and probing procedure described in Example 4, the dot blot technique was used to quantify H1N1 A/Puerto Rico/8/34 viruses produced in HEK293 cells (FIG. 9A). A standard (virus previously quantified by SRID) was used to mented with 10 mM DTT for 30 minutes with shaking. Plates (96-wells flat-bottom from Costar) were coated with 0.25 to 16 µg rHA overnight at 4° C. Antibodies 11H12, 10A9, 9D1, and anti-GFP (negative control) were added at a concentration of 100 ng/mL and incubated at 37° C. for 1 hour. HRP-conjugated secondary antibodies and TMB One component (Bethyl Laboratories) were used to reveal the signal. Results are shown in FIG. 10 and show that 11H12 and 9D1 have the same binding affinity for H5N1/A/Indonesia/05/2005, while 10A9 has a negligible binding affinity to this strain. This example demonstrates that a standard curve can be generated with the mAb in an ELISA assay, indicating applicability for quantification purposes.

Example 6: In Vivo Neutralization by Anti-HA Antibodies

The ability of the anti-influenza mAb obtained in Example 2 to neutralize influenza in vivo was evaluated.

BALB/C mice (n=5 per group) were infected intra-nasally with lethal concentrations of influenza viruses, and mAb were injected at different time points (15 µg mAb per gram of body weight in 100 µl). Mice treated with an anti-HA antibody named Uni-1 produced in rabbits (gift from Xuguang (Sean) Li from Health Canada) was used as a positive control. In the case where the mice were infected with 750 Plaque Forming Units (PFU) of H1N1 A/Puerto Rico/8/34, the mAb were injected 2 hours before infection, 4 hours post-infection and 24 hours post-infection (FIG. 11A). By day 8 post-infection, none of the untreated mice had survived whereas 80% of the mice treated with mAb 11H12 survived. The antibody 10A9 was the least protective against H1N1 A/Puerto Rico/8/34 with only 11% of the mice still alive by day 9 post-infection. In the second case, mice were infected with $10^4$ PFU of H3N2 A/Hong Kong/8/68, and mAb were injected 24 hours before infection, 2 hours before infection, 24 hours post-infection and 72 hours post-infection (FIG. 11B). As a negative control, an isotype control was also included. Untreated mice and mice treated with the isotype control were all dead by day 9 post-infection. On the other hand, mice treated with mAb 10A9 or Uni-1 survived the viral challenge for all the duration of the experiment (14 days). This example suggests that the mAb have a neutralizing capacity in vivo, and could be used as a therapeutic.

Example 7: Production of MAbs in Chinese Hamster Ovary (CHO) Cells

The antibodies from Example 2 were also expressed in CHO cells to facilitate large-scale production using bioreactor technologies that might be required to meet industrial needs for quantification reagents.

After selecting two pan-HA antibodies (11H12 and 10A9), these were sequenced and then plasmids were generated and transfected in CHO cells. The binding affinity and specificity of antibodies produced in CHO pools (FIG. 12B) is similar to the ones of antibodies produced from mouse hybridomas (FIG. 12A), strongly indicating possibility of large scale production.

Antibody production in Chinese Hamster Ovary (CHO) pools. F211-11H12 and F211-10A9 were sequenced by qRT-PCR and plasmids were synthesized (BIO BASIC Inc.). A CHO cell line (CHOBRI55E1-JN, proprietary to Applicant), which is inducible with cumate, was transfected with linear polyethylenimine (PEIMax, Polysciences) at a DNA/PEI ratio of 1 in 5 The resulting stable transfected pools produced antibodies named CHO-11H12 and CHO-10A9. Cells were maintained in PowerCHO media (Lonza) supplemented with 50 µM MSX, and antibody production was performed in BalanCD CHO growth media (Irvine Scientific) supplemented with 50 µM MSX at 32 C.

Dot blot. In brief, samples were denatured in 4M urea for 30 min with shaking at room temperature. After serial dilutions, 100 ul was loaded into the dot-blot wells in duplicate, along with a standard of known concentration previously quantified by SRID. Samples were then filtered through a nitrocellulose membrane using vacuum on a bio-dot apparatus (BioRad). The membrane was blocked in 5% non-fat dry milk in PBS for 1 hour at room temperature with shaking, followed by overnight incubation with 6 µg/ml antibody diluted in Odyssey blocking buffer at 4 C. Infrared-conjugated secondary antibodies were used for detection, along with the Odyssey scanner (LI-COR Biosciences).

Surface Plasmon Resonance (SPR). A BIACORE T200 (GE Healthcare) was used to determine the binding affinity (KD) of antibodies F211-10A9, CHO-10A9, F211-11H12 and CHO-11H12 to the peptide immunogen. All SPR experiments were run in PBS containing 0.05% Tween 20 (Teknova Inc.) and 3.4 mM EDTA as a running buffer. An anti-mouse-Fc surface was immobilized to approximately 2200 RUs using the Immobilization Wizard within the T200 control software set to a 2000 RU target.

Standard amine coupling of 20 µg/mL anti-mouse Fc solution in 10 mM NaOAc pH 4.5 was used. For the binding assay, approximately 350 RUs of antibody to be tested (-10A9 or -11H12) was captured onto a sheep anti-mouse Fc antibody surface by injecting 20 µg/mL solution for 300 seconds. This was followed by a single cycle kinetics injection of peptide using a 2-fold dilution series with a top-nominal concentration of 250 nM for antibodies -11H2, and 15 nM for antibodies -10A9, or PBST running buffer only for referencing. Using a flow rate of 100 µL/min with a 2700 second dissociation, 180 second injections of each peptide or buffer blank were used. The SPR surfaces were regenerated with 10 mM glycine pH 1.5 with a contact time of 120 seconds. Sensorgrams were double referenced and data were analyzed within Biacore T200 evaluation software v3.0 (GE Healthcare).

Hybridoma versus CHO-produced mAb. In order to scale up the production of pan-HA mAb, a different antibody production platform was explored. The variable regions of heavy and light chains of F211-11H12 and F211-10A9 hybridomas were sequenced by qRT-PCR and confirmed by mass spectrometry analysis of the purified mAbs (results not shown). DNA corresponding to the sequences were synthesized, cloned into vectors for full-length mouse IgG expression and transfected in a cumate-inducible CHO cell line using PEI in order to produce stable CHO pools. The two antibodies generated were named CHO-11H12 and CHO-10A9. Their binding affinity was tested by SPR and compared to their hybridomas counterpart; similar KD values were measured for the 4 mAbs, ranging from 3.38E-10 to 6.39E-10 M (Table 8).

TABLE 8

KD values (M) measured by SPR for pan-HA antibodies produced in mouse hybridomas and CHO pools.

| mAb | Average | KD (M) SD |
| --- | --- | --- |
| F211-10A9 | $3.38E^{-10}$ | $7.85E^{-11}$ |
| CHO-10A9 | $3.65E^{-10}$ | $4.21E^{-11}$ |
| F211-11H12 | $4.65E^{-10}$ | $7.17E^{-11}$ |
| CHO-11H12 | $6.39E^{-10}$ | $1.16E^{-10}$ |

The reactivity panel of the CHO-produced mAb cocktail is similar to the one generated by hybridoma-mAbs as demonstrated by dot blot against 18 strains listed in Table 9 (FIG. 12). The intensity of the signal correlates with the binding affinity of the antibody with a given strain. All the strains tested were recognized, except for a recombinant protein from H3N2 A/Wisconsin/67/05 (spot 4) for unknown reason; all other H3N2 strains were efficiently detected. Again, a variation due to the production platform was observed. For instance, the detection differs for the strain expressed as a recombinant protein (spot 5) compared to a virus (spot 19).

The first generation of antibodies used in this study were produced from mouse hybridomas with a yield of about 100 mg/L of culture, but higher levels of production are achievable using mammalian expression systems such as CHO cells. The pan-HA antibodies have therefore been sequenced and expressed in CHO cells. Similar binding affinities and specificities were observed between both types of antibodies. As a result, production can easily be scaled up using CHO cells in large bioreactors if needed.

TABLE 9

List of different strains used in dot blot of FIG. 12.

|  | Dot # | Subtype | Strain |
|---|---|---|---|
| rHA | 1 | H1N1 | A/Puerto Rico/8/34 |
|  | 2 | H1N1 | A/California/06/2008 |
|  | 3 | H3N2 | A/Aichi/2/1968 |
|  | 4 | H3N2 | A/Wisconsin/67/05 |
|  | 5 | H3N2 | A/Hong Kong/8/68 |
|  | 6 | H3N2 | A/Brisbane/10/2007 |
|  | 7 | H5N1 | A/Indonesia/05/2005 |
|  | 8 | H5N1 | A/Vietnam/1203/2004 |
|  | 9 | H7N7 | A/Netherlands/219/2003 |
|  | 10 | H7N9 | A/Anhui/1/2013 |
|  | 11 | H7N9 | A/Shanghai/2/2013 |
|  | 12 | H7N9 | A/Pigeon/Shanghai/S1069/2013 |
|  | 13 | H9N2 | A/Hong Kong/1073/1999 |
|  | 14 | B | Brisbane/60/2008 |
| Sd | 15 | H1N1 | A/California/06/2008 |
|  | 16 | B | Massachusetts/02/2016 |
| Virus | 17 | H1N1 | A/Puerto Rico/8/34 |
|  | 18 | H1N1 | A/Wilson Smith/33 |
| VLP | 19 | H3N2 | A/Hong Kong/8/68 |
|  | 20 | B | Lee/1940 |
|  | 21 | H3N1 | A/Victoria/361/2011 |
|  | 22 | H5N1 | A/Indonesia/05/2005 |
|  | 23 | H1N1 | A/California/06/2008 |
|  | 24 |  | Negative control (non-related protein) |

Legend: rHA = recombinant hemagglutinin, Sd = cell-produced calibrating standards (NIBSC), Virus = viruses produced in-house in HEK293 cells, VLP = viral like particles produced in plants (Medicago, Québec, QC).

Example 8—Primary Sequence Confirmation of Influenza mAbs

We confirmed the amino acid sequence of the following 3 mAbs (produced from mouse hybridomas): F211-11H12-2; F211-10A9-2; and F211-9D1-2.

IgGs were reduced, alkylated, and digested with trypsin. The resulting peptides were analyzed by nano-C18-LC and data-dependent MS-MS/MS on an LTQ-Orbitrap XL mass spectrometer. Peptides were identified by Mascot search on a database containing all 4 mAb sequences. Amino acid sequences identified with a Mascot score >30 are highlighted in bold red on the sequences of FIGS. 13.

The data suggest that the predicted sequences are likely to be correct for all 4 IgGs, especially when combined with the supportive intact mass data. We obtained sequence coverage averaging 75% which is standard in this type of analysis. Most areas that were not covered are areas that produce tryptic peptides that are either too large or too small to be identified under standard MS conditions. There are no obvious differences between 11H12 and 8C4.

Example 9—Delivery of Antibodies Through Recombinant Adeno-Associated Virus (rAAV)

Multiple repeated administrations of antibodies in at-risk population would be impractical and too expensive. Therefore, recombinant Adeno-Associated-Virus (rAAV) is being considered as a delivery system. Using rAAV would allow delivering the genes encoding for the mAb and ensuring their long-term expression. The heavy chain and light chain of the antibodies can be expressed on the same cassette and transfected into cells, along with two other plasmids (Rep/Cap and helper plasmids) to form the rAAV particles. After purification, the AAV can be injected for long term production of the antibodies. This would represent a cost-effective delivery route, especially in immunocompromised or elderly individuals.

CONCLUSION

The approach explored here is to use anti-stem antibodies to address the enduring quantification issue. The pan-HA antibodies have been tested against a large panel of strains including 13 HA influenza A subtypes as well as B subtypes. In addition, the pan-HA cocktail can detect egg-produced viruses, but also new-generation vaccines such as VLPs. Indeed, the host can also have an impact on detection due to different glycosylation patterns.

The monoclonal pan-HA antibodies were generated in mice against a highly conserved sequence found in the fusion peptide. Issues related to heterogeneity such as the ones observed with polyclonal antibodies are thus avoided.

Alternatively, large quantities can be produced in largescale bioreactors from CHO-producing cells to respond to industrial demand. This could be critical in case of a pandemic but could also considerably speed up process development.

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

LISTING OF SEQUENCES

| SEQ ID NO: | Sequence | Description |
|---|---|---|
| 1 | QSLLNSX$_1$X$_2$QKNX$_3$<br>where X$_1$ = R or D, X$_2$ = N or T, X$_3$ = H or F; | CDR L1 consensus |
| 35 | X$_1$AS<br>where X$_1$ = W or F; | CDR L2 |
| 2 | QQYYX$_1$X$_2$X$_3$X$_4$T<br>where X$_1$ = T or S, X$_2$ = Y or I, X$_3$ = P or no amino acid,<br>X$_4$ = R or L, | CDR L3 |
| 3 | GYX$_1$X$_2$TX$_3$DYY<br>where X$_1$ = S or T, X$_2$ = I or F, X$_3$ = S or no amino acid; | CDR H1 consensus |

LISTING OF SEQUENCES

| SEQ ID NO: | Sequence | Description |
|---|---|---|
| 4 | IGYDGX$_1$K<br>Where X$_1$ = S or T, | 9D1 and 11H12 CDR H2 |
| 5 | IYPGNGHT | 10A9 CDR H2 |
| 6 | TRDRANWDDYFDY | 9D1 and 11H12 CDR H3 |
| 7 | AYDLFNY | 10A9 CDR H3 |
| 8 | QSLLNSRNQKNH | 9D1 and 11H12 CDR L1 |
| 9 | QSLLNSDTQKNF | 10A9 CDR L1 |
| 36 | WAS | 9D1 and 11H12 CDR L2 |
| 37 | FAS | 10A9 CDR L2 |
| 10 | QQYYTYXRT<br>where X is P or no amino acid | 9D1 and 11H12 CDR L3 |
| 11 | QQYYSIPLT | 10A9 CDR L3 |
| 12 | GYSITSDYY | 9D1 and 11H12 CDR H1 |
| 13 | GYTFTDYY | 10A9 CDR H1 |
| 14 | QQYYTYRT | 9D1 and 11H12 CDR L3 |
| 15 | IGYDGSK | 9D1 CDR H2 |
| 16 | IGYDGTK | 11H12 CDR H2 |
| 17 | DIVMX$_1$QSPSSLAX$_2$SVGX$_3$KVTMSCKSSQSLLNSX$_4$X$_5$QK<br>NX$_6$LAWYQQKPGQSPKX$_7$LX$_8$YX$_9$ASTX$_{10}$ESGVPDRFX$_{11}$G<br>X$_{12}$GSGTDFTLTIX$_{13}$SVX$_{14}$AEDLAX$_{15}$YX$_{16}$CQQYYX$_{17}$X$_{18}$X$_{19}$<br>X$_{20}$TFGX$_{21}$GTKLEIK<br>where X$_1$ = S or T, X$_2$ = V or M, X$_3$ = E or Q, X$_4$ = R or D, X$_5$ = N or T, X$_6$ = H or F, X$_7$ = L or I, X$_8$ = I or V, X$_9$ = W or F, X$_{10}$ = R or K, X$_{11}$ = S or I, X$_{12}$ = D or S, X$_{13}$ = S or T, X$_{14}$ = K or Q, X$_{15}$ = V or D, X$_{16}$ = Y or F, X$_{17}$ = T or S, X$_{18}$ = Y or I, X$_{19}$ = P or no amino acid, X$_{20}$ = R or L, X$_{21}$ = G or A. | Light chain consensus sequence |
| 18 | DIVMSQSPSSLAVSVGEKVTMSCKSSQSLLNSRNQKNHL<br>AWYQQKPGQSPKLLIYWASTRESGVPDRFX$_1$GDGSGTDF<br>TLTISSVKAEDLAVYYCQQYYTYRTFGGGTKLEIK<br>where X$_1$ = S or T | 9D1 and 11H12 light chain |
| 19 | DIVMTQSPSSLAMSVGQKVTMSCKSSQSLLNSDTQKNFL<br>AWYQQKPGQSPKILVYFASTKESGVPDRFIGSGSGTDFT<br>LTITSVQAEDLADYFCQQYYSIPLTFGAGTKLELK | 10A9 light chain |
| 20 | DVQLQESGPGLVKPSQSLSLTCSVTGYSITSDYYWNWIR<br>QFPGNKLEWMAYIGYDGX$_1$KNYNPSLKNRISITRDTSKNQ<br>FFLKLNSVTTDDTATYYCTRDRANWDDYFDYWGQGTTLT<br>VSS<br>where X$_1$ = S or T | 9D1 and 11H12 heavy chain |
| 21 | QIQLQQSGPELVKPGAPVKISCKASGYTFTDYYIHWVNQR<br>PGQGLEWIGYIYPGNGHTVYNQKFKVRATLTADNPSSTA<br>YLQLNSLTSEDSGVYFCAYDLFNYWGQGTLVTVSA | 10A9 heavy chain |
| 22 | DIVMSQSPSSLAVSVGEKVTMSCKSSQSLLNSRNQKNHL<br>AWYQQKPGQSPKLLIYWASTRESGVPDRFSGDGSGTDF<br>TLTISSVKAEDLAVYYCQQYYTYRTFGGGTKLEIK | 9D1 light chain |
| 23 | DIVMSQSPSSLAVSVGEKVTMSCKSSQSLLNSRNQKNHL<br>AWYQQKPGQSPKLLIYWASTRESGVPDRFTGDGSGTDF<br>TLTISSVKAEDLAVYYCQQYYTYRTFGGGTKLEIK | 11H12 light chain |

LISTING OF SEQUENCES

| SEQ ID NO: | Sequence | Description |
|---|---|---|
| 24 | DVQLQESGPGLVKPSQSLSLTCSVTGYSITSDYYWNWIR QFPGNKLEWMAYIGYDGSKNYNPSLKNRISITRDTSKNQF FLKLNSVTTDDTATYYCTRDRANWDDYFDYWGQGTTLTV SS | 9D1 heavy chain |
| 25 | DVQLQESGPGLVKPSQSLSLTCSVTGYSITSDYYWNWIR QFPGNKLEWMAYIGYDGTKNYNPSLKNRISITRDTSKNQF FLKLNSVTTDDTATYYCTRDRANWDDYFDYWGQGTTLTV SS | 11H12 heavy chain |
| 26 | GLFGAIAGFIEGGW | Conserved peptide sequence |
| 27 | MVLQTQVFISLLLWISGAYG | Signal peptide |
| 28 | MDWTWRILFLVAAATGTHA | Signal peptide |
| 29 | FIG. 13A UPPER | F211-11H12-2 $V_L$ |
| 30 | FIG. 13A LOWER | F211-11H12-2 $V_H$ |
| 31 | FIG. 13B UPPER | F211-10A9-2 $V_L$ |
| 32 | FIG. 13B LOWER | F211-10A9-2 $V_H$ |
| 33 | FIG. 13C UPPER | F211-9D1-2 $V_L$ |
| 34 | FIG. 13C LOWER | F211-9D1-2 $V_H$ |
| 35 | FIG. 14A | 10A9 full sequence |
| 36 | FIG. 14B | 11H12 full sequence |

REFERENCES

All patents, patent applications and publications referred to throughout the application are listed below.

Chothia C, Lesk A M. Canonical structures for the hypervariable regions of immunoglobulins. J Mol Biol. 1987 Aug. 20; 196(4):901-17.

Chun S, Li C, Van Domselaru G, Wang J, Farnsworth A, Cui X, Rode H, Cyr T D, He R, and Li X. (2008) Universal antibodies and their applications to the quantitative determination of virtually all subtypes of the influenza A viral hemagglutinins. Vaccine 26(48): 6068-76.

de Kruif J, Logtenberg T. Leucine zipper dimerized bivalent and bispecific scFv antibodies from a semi-synthetic antibody phage display library. J Biol Chem. 1996 Mar. 29; 271(13):7630-4.

Dreyfus C, Laursen N S, Kwaks T, Zuijdgeest D, K. hayat R, Ekiert D C, Lee J H, Metlagel Z, Bujny M V, Jongeneelen M, van der Vlugt R, Lamrani M, Korse H J, Geelen E, Sabin O, Sieuwerts M, Brakenhoff J P, Vogels R, Li O T, Poon L L, Peiris M, Koudstaal W, Ward A B, Wilson I A, Ooudsmit J, and Friesen R H. (2012) Highly conserved protective epitopes on influenza B viruses. Science 337(6100): 1343-8.

Eisenberg, D., Schwarz, E., Komaromy, M., and Wall, R. Analysis of membrane and surface protein sequences with the hydrophobic moment plot. (1984) J. Mol. Biol. 179, 125-142

Fenner, L., Widmer, A. F., Goy, G., Rudin, S., and Frei, R. Rapid and reliable diagnostic algorithm for detection of Clostridium difficile. (2008) J. Clin. Microbiol. 46, 328-330.

Gonzales N R, DePascalis R, Schlom J, Kashmiri SVS (2005) Tumor Biol 26, 31-43.

Jones P T, Dear P H, Foote J, Neuberger M S, Winter G (1986) Nature 321, 522-525.

Kabat E A, Wu T T. Identical V region amino acid sequences and segments of sequences in antibodies of different specificities. Relative contributions of VH and VL genes, minigenes, and complementarity-determining regions to binding of antibody-combining sites. J Immunol. 1991; 147:1709-19

Kang S M, Song J M, Compans R W. Novel vaccines against influenza viruses. Virus Res. 2011 December; 162(1-2): 31-8.

Lefranc M P, Pommié C, Ruiz M, Giudicelli V, Foulquier E, Truong L, Thouvenin-Contet V, Lefranc G. IMGT unique numbering for immunoglobulin and T cell receptor variable domains and Ig superfamily V-like domains. Dev Comp Immunol. 2003 January; 27(1):55-77. Review.

Li C, Jaentchke B, Song Y, Wang J, Cyr T D, Van Domselaar G, et al. (2010) A simple slot blot for the detection of virtually all subtypes of the influenza A viral hemagglutinins using universal antibodies targeting the fusion peptide. Nat Protoc January; 5(1):14-9.

Merritt, E. A., and Hol, W. G. (1995) Curr. Opin. Struct. Biol. 5, 165-171.

Musher, D. M., Manhas, A., Jain, P., Nuila, F., Waqar, A., Logan, N., Marino, B., Graviss, E. A. Detection of Clostridium difficile toxin: comparison of enzyme immunoassay results with results obtained by cytotoxicity assay. (2007) J. Clin. Microbiol. 45, 2737-2739.

Nicaise M, Valeio-Lepiniec M, Minard P, Desmadril M. (2004) Affinity transfer by CDR grafting on a nonimmunoglobulin scaffold. Protein Sci. 13(7): 1882-1891.

Nielsen U B, Adams G P, Weiner L M, Marks J D. Targeting of bivalent anti-ErbB2 diabody antibody fragments to tumor cells is independent of the intrinsic antibody affinity. Cancer Res. 2000 Nov. 15; 60(22):6434-40.

Padlan E A (1991) A possible procedure for reducing the immunogenicity of antibody variable domains while preserving their ligand-binding properties. Mol Immunol 28, 489-498.

Planche, T. Aghaizu, A., Holliman, R., Riley, P., Poloniecki, J., Breathnach, A., and Krishna, S. (2008) Diagnosis of Clostridium difficile infection by toxin detection kits: a systematic review. Lancet Infect. Dis. 8, 777-784.

Ridgway, J. B., Presta, L. G., and Carter, P. 'Knobs-into-holes' engineering of antibody CH3 domains for heavy chain heterodimerization. (1996) Protein Eng. 9, 617-621.

Queen C, Schneider W P, Selick H E, Payne P W, Landolfi N F, Duncan J F, Avdalovic N M, Levitt M, Junghans R P, Waldmann T A (1989) Proc Natl Acad Sci USA 86, 10029-10033.

Ridgway, J. B., Presta, L. G., and Carter, P. (1996) Protein Eng. 9, 617-621.

Riechmann L, Clark M, Waldmann H, Winter G (1988) Nature 332, 323-327.

Rüssmann, H., Panthel, K., Bader, R. C., Schmitt, C., and Schaumann, R. Evaluation of three rapid assays for detection of Clostridium difficile toxin A and toxin B in stool specimens. (2007) Eur. J. Clin. Microbiol. Infect. Dis. 26, 115-119.

Sloan, L. M., Duresko, B. J., Gustafson, D. R., and Rosenblatt, J. E. Comparison of real-time PCR for detection of the tcdC gene with four toxin immunoassays and culture in diagnosis of Clostridium difficile infection. (2008) J. Clin. Microbiol. 46, 1996-2001.

Tempest P R, Bremmer P, Lambert M, Taylor G, Furze J M, Carr F J, Harris W J (1991) Biotechnology 9, 266-271.

Tsurushita N, Hinton, R P, Kumar S (2005) Design of humanized antibodies: From anti-Tac to Zenapax. Methods 36, 69-83.

Turgeon, D. K., Novicki, T. J., Quick, J., Carlson, L., Miller, P., Ulness, B., Cent, A., Ashley, R., Larson, A., Coyle, M., Limaye, A. P., Cookson, B. T., and Fritsche, T. R. Six rapid tests for direct detection of Clostridium difficile and its toxins in fecal samples compared with the fibroblast cytotoxicity assay. (2003) J. Clin. Microbiol. 41, 667-670.

Zhu X, Wang L, Liu R, Flutter B, Li S, Ding J, Tao H, Liu C, Sun M, Gao B. COMBODY: one-domain antibody multimer with improved avidity. Immunol Cell Biol. 2010 August; 88(6):667-75. doi: 10.1038/icb.2010.21. Epub 2010 Mar. 9.

WO 95/04069; WO/2004/076670; WO2003/046560.

---

The invention claimed is:

1. An isolated or purified antibody or fragment thereof, comprising:
   a) a light chain comprising CDR L1 of sequence QSLLNSRNQKNH (SEQ ID NO:8), CDR L2 of sequence WAS, and CDR L3 of sequence QQYYTYRT (SEQ ID NO:14); and a heavy chain comprising CDR H1 of sequence GYSITSDYY (SEQ ID NO:12), CDR H2 of sequence IGYDGSK (SEQ ID NO:15), and CDR H3 of sequence TRDRANWDDYFDY (SEQ ID NO:6);
   b) a light chain comprising CDR L1 of sequence QSLLNSRNQKNH (SEQ ID NO:8), CDR L2 of sequence WAS, and CDR L3 of sequence QQYYTYRT (SEQ ID NO:14); and a heavy chain comprising CDR H1 of sequence GYSITSDYY (SEQ ID NO:12), CDR H2 of sequence IGYDGTK (SEQ ID NO:16), and CDR H3 of sequence TRDRANWDDYFDY (SEQ ID NO:6); or
   c) a light chain comprising CDR L1 of sequence QSLLNSDTQKNF (SEQ ID NO:9), CDR L2 of sequence FAS, CDRL3 of sequence QQYYSIPLT (SEQ ID NO:11); and a heavy chain comprising CDR H1 of sequence GYTFTDYY (SEQ ID NO:13), CDR H2 of sequence IYPGNGHT (SEQ ID NO:5), and CDR H3 of sequence AYDLFNY (SEQ ID NO:7).

2. The isolated or purified antibody or fragment thereof of claim 1, wherein the variable light (VL) domain comprises a sequence selected from the group consisting of:
DIVMSQSPSSLAVSVGEKVTMSCKSSQSLLNSRNQKNHLAWYQQKPGQSPKLLIYWASTRESGVPDRFX₁GDGSGTDFTLTISSVKAEDLAVYYCQQYYTYRTFGGGT KLEIK (SEQ ID NO:18) where X₁=S or T; and
DIVMTQSPSSLAMSVGQKVTMSCKSSQSLLNSDTQKNFLAWYQQKPGQSPKILVYFASTKESGVPDRFIGSGSGTDFTLTITSVQAEDLADYFCQQYYSIPLTFGAGTKL ELK (SEQ ID NO:19).

3. The isolated or purified antibody or fragment thereof of claim 1, wherein the variable heavy (VH) domain comprises a sequence selected from the group consisting of:
DVQLQESGPGLVKPSQSLSLTCSVTGYSITSDYYWNWIRQFPGNKLEWMAYIGYDGX₁KNYNPSLKNRISITRDTSKNQFFLKLNSVTTDDTATYYCTRDRANWDDYF DYWGQGTTLTVSS (SEQ ID NO:20) X₁=S or T; and
QIQLQQSGPELVKPGAPVKISCKASGYTFTDYYIHWVNQRPGQGLEWIGYIYPGNGHTVYNQKFKVRATLTADNPSSTAYLQLNSLTSEDSGVYFCAYDLFNYWGQGT LVTVSA (SEQ ID NO:21).

4. The isolated or purified antibody or fragment thereof claim 1, wherein the isolated or purified antibody or fragment thereof comprises a sequence selected from the group consisting of
   a) a variable light (V_L) domain of sequence:

```
                              (SEQ ID NO: 22)
DIVMSQSPSSLAVSVGEKVTMSCKSSQSLLNSRNQKNHLAWYQQKPGQSP

KLLIYWASTRESGVPDRFSGDGSGTDFTLTISSVKAEDLAVYYCQQYYT

RTFGGGTKLEIK;
``` and variable heavy (V_H) domain of sequence:

```
                              (SEQ ID NO: 24)
DVQLQESGPGLVKPSQSLSLTCSVTGYSITSDYYWNWIRQFPGNKLEWMA

YIGYDGSKNYNPSLKNRISITRDTSKNQFFLKLNSVTTDDTATYYCTRDR

ANWDDYFDYWGQGTTLTVSS;
``` b) a variable light (V_L) domain of sequence:

```
                              (SEQ ID NO: 23)
DIVMSQSPSSLAVSVGEKVTMSCKSSQSLLNSRNQKNHLAWYQQKPGQSP

KLLIYWASTRESGVPDRFTGDGSGTDFTLTISSVKAEDLAVYYCQQYYTY

XRTFGGGTKLEIK;
``` and variable heavy (V_H) domain of sequence:

```
                              (SEQ ID NO: 25)
DVQLQESGPGLVKPSQSLSLTCSVTGYSITSDYYWNWIRQFPGNKLEWMA

YIGYDGTKNYNPSLKNRISITRDTSKNQFFLKLNSVTTDDTATYYCTRDR

ANWDDYFDYWGQGTTLTVSS;
``` and
   (c) a variable light (V_L) domain of sequence:

```
                              (SEQ ID NO: 19)
DIVMTQSPSSLAMSVGQKVTMSCKSSQSLLNSDTQKNFLAWYQQKPGQSP

KILVYFASTKESGVPDRFIGSGSGTDFTLTITSVQAEDLADYFCQQYYSI

PLTFGAGTKLELK;
``` and variable heavy (V_H) domain of sequence:

```
                              (SEQ ID NO: 21)
QIQLQQSGPELVKPGAPVKISCKASGYTFTDYYIHWVNQRPGQGLEWIGY

IYPGNGHTVYNQKFKVRATLTADNPSSTAYLQLNSLTSEDSGVYFCAYDL

FNYWGQGTLVTVSA;
```

5. The isolated or purified antibody or fragment thereof of claim 1, wherein the antibody or fragment thereof specifically binds to the peptide: GLFGAIAGFIEGGW (SEQ ID NO:26).

6. The isolated or purified antibody or fragment thereof of claim 1, wherein the antibody or fragment thereof is a full-length IgG, Fv, scFv, Fab, or F(ab')₂, and/or wherein the antibody or fragment thereof comprises framework regions from IgA, IgD, IgE, IgG, or IgM.

7. The isolated or purified antibody or fragment thereof of claim 1, wherein the antibody or fragment thereof is a chimeric antibody or fragment thereof.

8. A nucleic acid molecule encoding the isolated or purified antibody or fragment thereof of claim 1, or a vector comprising the nucleic acid molecule.

9. The isolated or purified antibody or fragment thereof of claim 1, wherein the antibody or fragment thereof is immobilized onto a surface.

10. The isolated or purified antibody or fragment thereof of claim 1, wherein the antibody or fragment thereof is linked to a cargo molecule.

11. A composition comprising one or more than one isolated or purified antibody or fragment thereof of claim 1 and a pharmaceutically-acceptable carrier, diluent, or excipient.

12. An in vitro method of detecting influenza hemagglutinin (HA), comprising:
   a) contacting a biological sample or a viral suspension, with an isolated or purified antibody or fragment thereof according to claim 1 linked to a detectable agent; and
   b) detecting the detectable agent linked to the antibody or fragment thereof bound to hemagglutinin in the biological sample or a viral suspension.

13. A method of treating influenza in a subject, comprising administering a pharmaceutically acceptable dose of an isolated or purified antibody or fragment thereof of claim 1 to the subject.

14. A kit for detecting influenza HA comprising a support and an isolated or purified labelled-antibody or fragment thereof according to claim 1.

15. An in vitro method for quantifying influenza HA, comprising:
   a) contacting a biological sample suspected of comprising influenza HA with an isolated or purified antibody or fragment thereof according to claim 1 linked to a detectable agent; and
   b) quantifying the detectable agent linked to the antibody or fragment thereof.

16. A kit for measuring influenza HA comprising: one or more than one antibody as defined in claim 1; and a detection reagent for detecting the antibody bound to said influenza HA in a biological sample; a measuring reagent for measuring a level of the detection agent.

17. An isolated or purified antibody or fragment thereof, wherein the antibody is selected from:
   mAb 11H12 comprising sequences SEQ ID NO: 29 and 30;
   mAb 10A9 comprising sequences SEQ ID NO: 31 and 32; and
   mAb 9D1 comprising sequences SEQ ID NO: 33 and 34.

18. The isolated or purified antibody or fragment thereof of claim 7, wherein the chimeric antibody or fragment thereof constant domain is from human IgG1 or wherein the chimeric antibody or fragment thereof comprises human kappa 1 light chain and human IgG1 heavy chain constant domains.

19. The isolated or purified antibody or fragment thereof of claim 10, wherein the cargo molecule is a detectable agent, a therapeutic agent, a drug, a peptide, an enzyme, a growth factor, a cytokine, a receptor trap, an antibody or fragment thereof, a chemical compound, a carbohydrate moiety, DNA-based molecules, a neutralizing agent, viral vector, one or more liposomes or nanocarriers loaded with any of the previously recited types of cargo molecules, or one or more nanoparticle, nanowire, nanotube, or quantum dots.

* * * * *

SEQUENCE LISTING

```
<160> NUMBER OF SEQ ID NOS: 36

<210> SEQ ID NO 1
<211> LENGTH: 12
<212> TYPE: PRT
<213> ORGANISM: Artificial Sequence
<220> FEATURE:
<223> OTHER INFORMATION: Complementarity determining region (CDR) L1
      sequence
<220> FEATURE:
<221> NAME/KEY: MISC_FEATURE
<222> LOCATION: (7)..(7)
<223> OTHER INFORMATION: Wherein X is R or D
<220> FEATURE:
<221> NAME/KEY: MISC_FEATURE
<222> LOCATION: (8)..(8)
<223> OTHER INFORMATION: Wherein X is N or T
<220> FEATURE:
<221> NAME/KEY: MISC_FEATURE
<222> LOCATION: (12)..(12)
<223> OTHER INFORMATION: Wherein X is H or F

<400> SEQUENCE: 1

Gln Ser Leu Leu Asn Ser Xaa Xaa Gln Lys Asn Xaa
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Complementarity determining region (CDR) L3
      sequence
<220> FEATURE:
<221> NAME/KEY: MISC_FEATURE
<222> LOCATION: (5)..(5)
<223> OTHER INFORMATION: Wherein X is T or S
<220> FEATURE:
<221> NAME/KEY: MISC_FEATURE
<222> LOCATION: (6)..(6)
<223> OTHER INFORMATION: Wherein X is Y or I
<220> FEATURE:
<221> NAME/KEY: MISC_FEATURE
<222> LOCATION: (7)..(7)
```

```
<223> OTHER INFORMATION: Wherein X is P or no amino acid
<220> FEATURE:
<221> NAME/KEY: MISC_FEATURE
<222> LOCATION: (8)..(8)
<223> OTHER INFORMATION: Wherein X is R or L

<400> SEQUENCE: 2

Gln Gln Tyr Tyr Xaa Xaa Xaa Xaa Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Complementarity determining region (CDR) H1
      sequence
<220> FEATURE:
<221> NAME/KEY: MISC_FEATURE
<222> LOCATION: (3)..(3)
<223> OTHER INFORMATION: Wherein X is S or T
<220> FEATURE:
<221> NAME/KEY: MISC_FEATURE
<222> LOCATION: (4)..(4)
<223> OTHER INFORMATION: Wherein X is I or F
<220> FEATURE:
<221> NAME/KEY: MISC_FEATURE
<222> LOCATION: (6)..(6)
<223> OTHER INFORMATION: Wherein X is S or no amino acid

<400> SEQUENCE: 3

Gly Tyr Xaa Xaa Thr Xaa Asp Tyr Tyr
1               5

<210> SEQ ID NO 4
<211> LENGTH: 7
<212> TYPE: PRT
<213> ORGANISM: Artificial Sequence
<220> FEATURE:
<223> OTHER INFORMATION: Complementarity determining region (CDR) H2
      sequence
<220> FEATURE:
<221> NAME/KEY: MISC_FEATURE
<222> LOCATION: (6)..(6)
<223> OTHER INFORMATION: Wherein X is S or T

<400> SEQUENCE: 4

Ile Gly Tyr Asp Gly Xaa Lys
1               5

<210> SEQ ID NO 5
<211> LENGTH: 8
<212> TYPE: PRT
<213> ORGANISM: Artificial Sequence
<220> FEATURE:
<223> OTHER INFORMATION: Complementarity determining region (CDR) H2
      sequence

<400> SEQUENCE: 5

Ile Tyr Pro Gly Asn Gly His Thr
1               5

<210> SEQ ID NO 6
<211> LENGTH: 13
<212> TYPE: PRT
<213> ORGANISM: Artificial Sequence
<220> FEATURE:
<223> OTHER INFORMATION: Complementarity determining region (CDR) H3
      sequence
```

```
<400> SEQUENCE: 6

Thr Arg Asp Arg Ala Asn Trp Asp Asp Tyr Phe Asp Tyr
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Complementarity determining region (CDR) H3
      sequence

<400> SEQUENCE: 7

Ala Tyr Asp Leu Phe Asn Tyr
1               5

<210> SEQ ID NO 8
<211> LENGTH: 12
<212> TYPE: PRT
<213> ORGANISM: Artificial Sequence
<220> FEATURE:
<223> OTHER INFORMATION: Complementarity determining region (CDR) L1
      sequence

<400> SEQUENCE: 8

Gln Ser Leu Leu Asn Ser Arg Asn Gln Lys Asn His
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Complementarity determining region (CDR) L1
      sequence

<400> SEQUENCE: 9

Gln Ser Leu Leu Asn Ser Asp Thr Gln Lys Asn Phe
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Complementarity determining region (CDR) L3
      sequence
<220> FEATURE:
<221> NAME/KEY: MISC_FEATURE
<222> LOCATION: (7)..(7)
<223> OTHER INFORMATION: Wherein X is P or no amino acid

<400> SEQUENCE: 10

Gln Gln Tyr Tyr Thr Tyr Xaa Arg Thr
1               5

<210> SEQ ID NO 11
<211> LENGTH: 9
<212> TYPE: PRT
<213> ORGANISM: Artificial Sequence
<220> FEATURE:
<223> OTHER INFORMATION: Complementarity determining region (CDR) L3
      sequence

<400> SEQUENCE: 11

Gln Gln Tyr Tyr Ser Ile Pro Leu Thr
1               5
```

<210> SEQ ID NO 12
<211> LENGTH: 9
<212> TYPE: PRT
<213> ORGANISM: Artificial Sequence
<220> FEATURE:
<223> OTHER INFORMATION: Complementarity determining region (CDR) H1
      sequence

<400> SEQUENCE: 12

Gly Tyr Ser Ile Thr Ser Asp Tyr Tyr
1               5

<210> SEQ ID NO 13
<211> LENGTH: 8
<212> TYPE: PRT
<213> ORGANISM: Artificial Sequence
<220> FEATURE:
<223> OTHER INFORMATION: Complementarity determining region (CDR) H1
      sequence

<400> SEQUENCE: 13

Gly Tyr Thr Phe Thr Asp Tyr Tyr
1               5

<210> SEQ ID NO 14
<211> LENGTH: 8
<212> TYPE: PRT
<213> ORGANISM: Artificial Sequence
<220> FEATURE:
<223> OTHER INFORMATION: Complementarity determining region (CDR) L3
      sequence

<400> SEQUENCE: 14

Gln Gln Tyr Tyr Thr Tyr Arg Thr
1               5

<210> SEQ ID NO 15
<211> LENGTH: 7
<212> TYPE: PRT
<213> ORGANISM: Artificial Sequence
<220> FEATURE:
<223> OTHER INFORMATION: Complementarity determining region (CDR) H2
      sequence

<400> SEQUENCE: 15

Ile Gly Tyr Asp Gly Ser Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Complementarity determining region (CDR) H2
      sequence

<400> SEQUENCE: 16

Ile Gly Tyr Asp Gly Thr Lys
1               5

<210> SEQ ID NO 17
<211> LENGTH: 113
<212> TYPE: PRT
<213> ORGANISM: Artificial Sequence
<220> FEATURE:
<223> OTHER INFORMATION: Sequence from variable light domain (VL)
<220> FEATURE:

```
<221> NAME/KEY: MISC_FEATURE
<222> LOCATION: (5)..(5)
<223> OTHER INFORMATION: Wherein X is S or T
<220> FEATURE:
<221> NAME/KEY: MISC_FEATURE
<222> LOCATION: (13)..(13)
<223> OTHER INFORMATION: Wherein X is V or M
<220> FEATURE:
<221> NAME/KEY: MISC_FEATURE
<222> LOCATION: (17)..(17)
<223> OTHER INFORMATION: Wherein X is E or Q
<220> FEATURE:
<221> NAME/KEY: MISC_FEATURE
<222> LOCATION: (33)..(33)
<223> OTHER INFORMATION: Wherein X is R or D
<220> FEATURE:
<221> NAME/KEY: MISC_FEATURE
<222> LOCATION: (34)..(34)
<223> OTHER INFORMATION: Wherein X is N or T
<220> FEATURE:
<221> NAME/KEY: MISC_FEATURE
<222> LOCATION: (38)..(38)
<223> OTHER INFORMATION: Wherein X is H or F
<220> FEATURE:
<221> NAME/KEY: MISC_FEATURE
<222> LOCATION: (52)..(52)
<223> OTHER INFORMATION: Wherein X is L or I
<220> FEATURE:
<221> NAME/KEY: MISC_FEATURE
<222> LOCATION: (54)..(54)
<223> OTHER INFORMATION: Wherein X is I or V
<220> FEATURE:
<221> NAME/KEY: MISC_FEATURE
<222> LOCATION: (56)..(56)
<223> OTHER INFORMATION: Wherein X is W or F
<220> FEATURE:
<221> NAME/KEY: MISC_FEATURE
<222> LOCATION: (60)..(60)
<223> OTHER INFORMATION: Wherein X is R or K
<220> FEATURE:
<221> NAME/KEY: MISC_FEATURE
<222> LOCATION: (69)..(69)
<223> OTHER INFORMATION: Wherein X is S or I
<220> FEATURE:
<221> NAME/KEY: MISC_FEATURE
<222> LOCATION: (71)..(71)
<223> OTHER INFORMATION: Wherein X is D or S
<220> FEATURE:
<221> NAME/KEY: MISC_FEATURE
<222> LOCATION: (82)..(82)
<223> OTHER INFORMATION: Wherein X is S or T
<220> FEATURE:
<221> NAME/KEY: MISC_FEATURE
<222> LOCATION: (85)..(85)
<223> OTHER INFORMATION: Wherein X is K or Q
<220> FEATURE:
<221> NAME/KEY: MISC_FEATURE
<222> LOCATION: (91)..(91)
<223> OTHER INFORMATION: Wherein X is V or D
<220> FEATURE:
<221> NAME/KEY: MISC_FEATURE
<222> LOCATION: (93)..(93)
<223> OTHER INFORMATION: Wherein X is Y or F
<220> FEATURE:
<221> NAME/KEY: MISC_FEATURE
<222> LOCATION: (99)..(99)
<223> OTHER INFORMATION: Wherein X is T or S
<220> FEATURE:
<221> NAME/KEY: MISC_FEATURE
<222> LOCATION: (100)..(100)
<223> OTHER INFORMATION: Wherein X is Y or I
<220> FEATURE:
<221> NAME/KEY: MISC_FEATURE
<222> LOCATION: (101)..(101)
<223> OTHER INFORMATION: Wherein X is P or no amino acid
<220> FEATURE:
<221> NAME/KEY: MISC_FEATURE
<222> LOCATION: (102)..(102)
<223> OTHER INFORMATION: Wherein X is R or L
```

```
<220> FEATURE:
<221> NAME/KEY: MISC_FEATURE
<222> LOCATION: (106)..(106)
<223> OTHER INFORMATION: Wherein X is G or A

<400> SEQUENCE: 17

Asp Ile Val Met Xaa Gln Ser Pro Ser Ser Leu Ala Xaa Ser Val Gly
1               5                   10                  15

Xaa Lys Val Thr Met Ser Cys Lys Ser Ser Gln Ser Leu Leu Asn Ser
                20                  25                  30

Xaa Xaa Gln Lys Asn Xaa Leu Ala Trp Tyr Gln Gln Lys Pro Gly Gln
        35                  40                  45

Ser Pro Lys Xaa Leu Xaa Tyr Xaa Ala Ser Thr Xaa Glu Ser Gly Val
    50                  55                  60

Pro Asp Arg Phe Xaa Gly Xaa Gly Ser Gly Thr Asp Phe Thr Leu Thr
65              70                  75                  80

Ile Xaa Ser Val Xaa Ala Glu Asp Leu Ala Xaa Tyr Xaa Cys Gln Gln
        85                  90                  95

Tyr Tyr Xaa Xaa Xaa Xaa Thr Phe Gly Xaa Gly Thr Lys Leu Glu Ile
            100                 105                 110

Lys

<210> SEQ ID NO 18
<211> LENGTH: 112
<212> TYPE: PRT
<213> ORGANISM: Artificial Sequence
<220> FEATURE:
<223> OTHER INFORMATION: Sequence from variable light domain (VL)
<220> FEATURE:
<221> NAME/KEY: MISC_FEATURE
<222> LOCATION: (69)..(69)
<223> OTHER INFORMATION: Wherein X is S or T

<400> SEQUENCE: 18

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Asn Ser
                20                  25                  30

Arg Asn Gln Lys Asn His Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Xaa Gly Asp Gly Ser Gly Thr Asp Phe Thr Leu Thr
65              70                  75                  80

Ile Ser Ser Val Lys Ala Glu Asp Leu Ala Val Tyr Tyr Cys Gln Gln
        85                  90                  95

Tyr Tyr Thr Tyr Arg Thr Phe Gly Gly Gly Thr Lys Leu Glu Ile Lys
            100                 105                 110

<210> SEQ ID NO 19
<211> LENGTH: 113
<212> TYPE: PRT
<213> ORGANISM: Artificial Sequence
<220> FEATURE:
<223> OTHER INFORMATION: Sequence from variable light domain (VL)

<400> SEQUENCE: 19

Asp Ile Val Met Thr Gln Ser Pro Ser Ser Leu Ala Met Ser Val Gly
1               5                   10                  15
```

```
Gln Lys Val Thr Met Ser Cys Lys Ser Ser Gln Ser Leu Leu Asn Ser
            20                  25                  30

Asp Thr Gln Lys Asn Phe Leu Ala Trp Tyr Gln Gln Lys Pro Gly Gln
            35                  40                  45

Ser Pro Lys Ile Leu Val Tyr Phe Ala Ser Thr Lys Glu Ser Gly Val
 50                  55                  60

Pro Asp Arg Phe Ile Gly Ser Gly Ser Gly Thr Asp Phe Thr Leu Thr
 65                  70                  75                  80

Ile Thr Ser Val Gln Ala Glu Asp Leu Ala Asp Tyr Phe Cys Gln Gln
                85                  90                  95

Tyr Tyr Ser Ile Pro Leu Thr Phe Gly Ala Gly Thr Lys Leu Glu Leu
            100                 105                 110

Lys

<210> SEQ ID NO 20
<211> LENGTH: 120
<212> TYPE: PRT
<213> ORGANISM: Artificial Sequence
<220> FEATURE:
<223> OTHER INFORMATION: Sequence from variable heavy domain (VH)
<220> FEATURE:
<221> NAME/KEY: MISC_FEATURE
<222> LOCATION: (57)..(57)
<223> OTHER INFORMATION: Wherein X is S or T

<400> SEQUENCE: 20

Asp Val Gln Leu Gln Glu Ser Gly Pro Gly Leu Val Lys Pro Ser Gln
 1               5                  10                  15

Ser Leu Ser Leu Thr Cys Ser Val Thr Gly Tyr Ser Ile Thr Ser Asp
            20                  25                  30

Tyr Tyr Trp Asn Trp Ile Arg Gln Phe Pro Gly Asn Lys Leu Glu Trp
            35                  40                  45

Met Ala Tyr Ile Gly Tyr Asp Gly Xaa Lys Asn Tyr Asn Pro Ser Leu
 50                  55                  60

Lys Asn Arg Ile Ser Ile Thr Arg Asp Thr Ser Lys Asn Gln Phe Phe
 65                  70                  75                  80

Leu Lys Leu Asn Ser Val Thr Thr Asp Asp Thr Ala Thr Tyr Tyr Cys
                85                  90                  95

Thr Arg Asp Arg Ala Asn Trp Asp Asp Tyr Phe Asp Tyr Trp Gly Gln
            100                 105                 110

Gly Thr Thr Leu Thr Val Ser Ser
            115                 120

<210> SEQ ID NO 21
<211> LENGTH: 114
<212> TYPE: PRT
<213> ORGANISM: Artificial Sequence
<220> FEATURE:
<223> OTHER INFORMATION: Sequence from variable heavy domain (VH)

<400> SEQUENCE: 21

Gln Ile Gln Leu Gln Gln Ser Gly Pro Glu Leu Val Lys Pro Gly Ala
 1               5                  10                  15

Pro Val Lys Ile Ser Cys Lys Ala Ser Gly Tyr Thr Phe Thr Asp Tyr
            20                  25                  30

Tyr Ile His Trp Val Asn Gln Arg Pro Gly Gln Gly Leu Glu Trp Ile
            35                  40                  45
```

-continued

Gly Tyr Ile Tyr Pro Gly Asn Gly His Thr Val Tyr Asn Gln Lys Phe
            50                  55                  60

Lys Val Arg Ala Thr Leu Thr Ala Asp Asn Pro Ser Ser Thr Ala Tyr
 65                  70                  75                  80

Leu Gln Leu Asn Ser Leu Thr Ser Glu Asp Ser Gly Val Tyr Phe Cys
                 85                  90                  95

Ala Tyr Asp Leu Phe Asn Tyr Trp Gly Gln Gly Thr Leu Val Thr Val
             100                 105                 110

Ser Ala

<210> SEQ ID NO 22
<211> LENGTH: 112
<212> TYPE: PRT
<213> ORGANISM: Artificial Sequence
<220> FEATURE:
<223> OTHER INFORMATION: Sequence of variable light domain (VL)

<400> SEQUENCE: 22

Asp Ile Val Met Ser Gln Ser Pro Ser Ser Leu Ala Val Ser Val Gly
 1               5                  10                  15

Glu Lys Val Thr Met Ser Cys Lys Ser Ser Gln Ser Leu Leu Asn Ser
                 20                  25                  30

Arg Asn Gln Lys Asn His Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
         50                  55                  60

Pro Asp Arg Phe Ser Gly Asp Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Thr Tyr Arg Thr Phe Gly Gly Gly Thr Lys Leu Glu Ile Lys
             100                 105                 110

<210> SEQ ID NO 23
<211> LENGTH: 112
<212> TYPE: PRT
<213> ORGANISM: Artificial Sequence
<220> FEATURE:
<223> OTHER INFORMATION: Sequence of variable light domain (VL)

<400> SEQUENCE: 23

Asp Ile Val Met Ser Gln Ser Pro Ser Ser Leu Ala Val Ser Val Gly
 1               5                  10                  15

Glu Lys Val Thr Met Ser Cys Lys Ser Ser Gln Ser Leu Leu Asn Ser
                 20                  25                  30

Arg Asn Gln Lys Asn His Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
         50                  55                  60

Pro Asp Arg Phe Thr Gly Asp Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Thr Tyr Arg Thr Phe Gly Gly Gly Thr Lys Leu Glu Ile Lys
             100                 105                 110

<210> SEQ ID NO 24

```
<211> LENGTH: 120
<212> TYPE: PRT
<213> ORGANISM: Artificial Sequence
<220> FEATURE:
<223> OTHER INFORMATION: Sequence of variable heavy domain (VH)

<400> SEQUENCE: 24

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asp
            20                  25                  30

Tyr Tyr Trp Asn Trp Ile Arg Gln Phe Pro Gly Asn Lys Leu Glu Trp
        35                  40                  45

Met Ala Tyr Ile Gly Tyr Asp Gly Ser Lys Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Asp Thr Ala Thr Tyr Tyr Cys
                85                  90                  95

Thr Arg Asp Arg Ala Asn Trp Asp Asp Tyr Phe Asp Tyr Trp Gly Gln
            100                 105                 110

Gly Thr Thr Leu Thr Val Ser Ser
            115                 120

<210> SEQ ID NO 25
<211> LENGTH: 120
<212> TYPE: PRT
<213> ORGANISM: Artificial Sequence
<220> FEATURE:
<223> OTHER INFORMATION: Sequence of variable heavy domain (VH)

<400> SEQUENCE: 25

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asp
            20                  25                  30

Tyr Tyr Trp Asn Trp Ile Arg Gln Phe Pro Gly Asn Lys Leu Glu Trp
        35                  40                  45

Met Ala Tyr Ile Gly Tyr Asp Gly Thr Lys Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Asp Thr Ala Thr Tyr Tyr Cys
                85                  90                  95

Thr Arg Asp Arg Ala Asn Trp Asp Asp Tyr Phe Asp Tyr Trp Gly Gln
            100                 105                 110

Gly Thr Thr Leu Thr Val Ser Ser
            115                 120

<210> SEQ ID NO 26
<211> LENGTH: 14
<212> TYPE: PRT
<213> ORGANISM: Artificial Sequence
<220> FEATURE:
<223> OTHER INFORMATION: Antibody, or fragment thereof, binding peptide

<400> SEQUENCE: 26

Gly Leu Phe Gly Ala Ile Ala Gly Phe Ile Glu Gly Gly Trp
1               5                   10
```

<210> SEQ ID NO 27
<211> LENGTH: 20
<212> TYPE: PRT
<213> ORGANISM: Artificial Sequence
<220> FEATURE:
<223> OTHER INFORMATION: Signal peptide

<400> SEQUENCE: 27

```
Met Val Leu Gln Thr Gln Val Phe Ile Ser Leu Leu Trp Ile Ser
1               5                   10                  15

Gly Ala Tyr Gly
            20
```

<210> SEQ ID NO 28
<211> LENGTH: 19
<212> TYPE: PRT
<213> ORGANISM: Artificial Sequence
<220> FEATURE:
<223> OTHER INFORMATION: Signal peptide

<400> SEQUENCE: 28

```
Met Asp Trp Thr Trp Arg Ile Leu Phe Leu Val Ala Ala Thr Gly
1               5                   10                  15

Thr His Ala
```

<210> SEQ ID NO 29
<211> LENGTH: 469
<212> TYPE: PRT
<213> ORGANISM: Artificial Sequence
<220> FEATURE:
<223> OTHER INFORMATION: Sequence from mAbs

<400> SEQUENCE: 29

```
Arg Met Lys Val Leu Ser Leu Leu Tyr Leu Leu Thr Ala Ile Pro Gly
1               5                   10                  15

Phe Leu Ser Asp Val Gln Leu Gln Glu Ser Gly Pro Gly Leu Val Lys
                20                  25                  30

Pro Ser Gln Ser Leu Ser Leu Thr Cys Ser Val Thr Gly Tyr Ser Ile
            35                  40                  45

Thr Ser Asp Tyr Tyr Trp Asn Trp Ile Arg Gln Phe Pro Gly Asn Lys
        50                  55                  60

Leu Glu Trp Met Ala Tyr Ile Gly Tyr Asp Gly Thr Lys Asn Tyr Asn
65                  70                  75                  80

Pro Ser Leu Lys Asn Arg Ile Ser Ile Thr Arg Asp Thr Ser Lys Asn
                85                  90                  95

Gln Phe Phe Leu Lys Leu Asn Ser Val Thr Thr Asp Thr Ala Thr
            100                 105                 110

Tyr Tyr Cys Thr Arg Asp Arg Ala Asn Trp Asp Tyr Phe Asp Tyr
        115                 120                 125

Trp Gly Gln Gly Thr Thr Leu Thr Val Ser Ser Ala Lys Thr Thr Ala
    130                 135                 140

Pro Ser Val Tyr Pro Leu Ala Pro Val Cys Gly Asp Thr Thr Gly Ser
145                 150                 155                 160

Ser Val Thr Leu Gly Cys Leu Val Lys Gly Tyr Phe Pro Glu Pro Val
                165                 170                 175

Thr Leu Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205
```

Val Thr Ser Ser Thr Trp Pro Ser Gln Ser Ile Thr Cys Asn Val Ala
    210                 215                 220

His Pro Ala Ser Ser Thr Lys Val Asp Lys Lys Ile Glu Pro Arg Gly
225                 230                 235                 240

Pro Thr Ile Lys Pro Cys Pro Pro Cys Lys Cys Pro Ala Pro Asn Leu
                245                 250                 255

Leu Gly Gly Pro Ser Val Phe Ile Phe Pro Pro Lys Ile Lys Asp Val
                260                 265                 270

Leu Met Ile Ser Leu Ser Pro Ile Val Thr Cys Val Val Asp Val
    275                 280                 285

Ser Glu Asp Asp Pro Asp Val Gln Ile Ser Trp Phe Val Asn Asn Val
    290                 295                 300

Glu Val His Thr Ala Gln Thr Gln Thr His Arg Glu Asp Tyr Asn Ser
305                 310                 315                 320

Thr Leu Arg Val Val Ser Ala Leu Pro Ile Gln His Gln Asp Trp Met
                325                 330                 335

Ser Gly Lys Glu Phe Lys Cys Lys Val Asn Asn Lys Asp Leu Pro Ala
                340                 345                 350

Pro Ile Glu Arg Thr Ile Ser Lys Pro Lys Gly Ser Val Arg Ala Pro
                355                 360                 365

Gln Val Tyr Val Leu Pro Pro Pro Glu Glu Glu Met Thr Lys Lys Gln
    370                 375                 380

Val Thr Leu Thr Cys Met Val Thr Asp Phe Met Pro Glu Asp Ile Tyr
385                 390                 395                 400

Val Glu Trp Thr Asn Asn Gly Lys Thr Glu Leu Asn Tyr Lys Asn Thr
                405                 410                 415

Glu Pro Val Leu Asp Ser Asp Gly Ser Tyr Phe Met Tyr Ser Lys Leu
                420                 425                 430

Arg Val Glu Lys Lys Asn Trp Val Arg Asn Ser Tyr Ser Cys Ser
                435                 440                 445

Val Val His Glu Gly Leu His Asn His His Thr Thr Lys Ser Phe Ser
    450                 455                 460

Arg Thr Pro Gly Lys
465

<210> SEQ ID NO 30
<211> LENGTH: 233
<212> TYPE: PRT
<213> ORGANISM: Artificial Sequence
<220> FEATURE:
<223> OTHER INFORMATION: Sequence from mAbs

<400> SEQUENCE: 30

Val Leu Met Leu Leu Leu Leu Trp Val Ser Gly Thr Cys Gly Asp Ile
1               5                   10                  15

Val Met Ser Gln Ser Pro Ser Ser Leu Ala Val Ser Val Gly Glu Lys
                20                  25                  30

Val Thr Met Ser Cys Lys Ser Ser Gln Ser Leu Leu Asn Ser Arg Asn
                35                  40                  45

Gln Lys Asn His Leu Ala Trp Tyr Gln Gln Lys Pro Gly Gln Ser Pro
            50                  55                  60

Lys Leu Leu Ile Tyr Trp Ala Ser Thr Arg Glu Ser Gly Val Pro Asp
65                  70                  75                  80

Arg Phe Thr Gly Asp Gly Ser Gly Thr Asp Phe Thr Leu Thr Ile Ser
                85                  90                  95

-continued

```
Ser Val Lys Ala Glu Asp Leu Ala Val Tyr Tyr Cys Gln Gln Tyr Tyr
            100                 105                 110

Thr Tyr Arg Thr Phe Gly Gly Gly Thr Lys Leu Glu Ile Lys Arg Ala
        115                 120                 125

Asp Ala Ala Pro Thr Val Ser Ile Phe Pro Pro Ser Ser Glu Gln Leu
    130                 135                 140

Thr Ser Gly Gly Ala Ser Val Val Cys Phe Leu Asn Asn Phe Tyr Pro
145                 150                 155                 160

Lys Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
            180                 185                 190

Ser Met Ser Ser Thr Leu Thr Leu Thr Lys Asp Glu Tyr Glu Arg His
        195                 200                 205

Asn Ser Tyr Thr Cys Glu Ala Thr His Lys Thr Ser Thr Ser Pro Ile
    210                 215                 220

Val Lys Ser Phe Asn Arg Asn Glu Cys
225                 230

<210> SEQ ID NO 31
<211> LENGTH: 449
<212> TYPE: PRT
<213> ORGANISM: Artificial Sequence
<220> FEATURE:
<223> OTHER INFORMATION: Sequence from mAbs

<400> SEQUENCE: 31

Ala Gly Val His Cys Gln Ile Gln Leu Gln Gln Ser Gly Pro Glu Leu
1               5                   10                  15

Val Lys Pro Gly Ala Pro Val Lys Ile Ser Cys Lys Ala Ser Gly Tyr
            20                  25                  30

Thr Phe Thr Asp Tyr Tyr Ile His Trp Val Asn Gln Arg Pro Gly Gln
        35                  40                  45

Gly Leu Glu Trp Ile Gly Tyr Ile Tyr Pro Gly Asn Gly His Thr Val
    50                  55                  60

Tyr Asn Gln Lys Phe Lys Val Arg Ala Thr Leu Thr Ala Asp Asn Pro
65                  70                  75                  80

Ser Ser Thr Ala Tyr Leu Gln Leu Asn Ser Leu Thr Ser Glu Asp Ser
                85                  90                  95

Gly Val Tyr Phe Cys Ala Tyr Asp Leu Phe Asn Tyr Trp Gly Gln Gly
            100                 105                 110

Thr Leu Val Thr Val Ser Ala Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220
```

```
Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
                260                 265                 270

Pro Asp Val Gln Ile Ser Trp Phe Val Asn Asn Val Glu Val His Thr
            275                 280                 285

Ala Gln Thr Gln Thr His Arg Glu Asp Tyr Asn Ser Thr Leu Arg Val
        290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
                340                 345                 350

Leu Pro Pro Pro Glu Glu Glu Met Thr Lys Lys Gln Val Thr Leu Thr
            355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
                420                 425                 430

Gly Leu His Asn His His Thr Thr Lys Ser Phe Ser Arg Thr Pro Gly
            435                 440                 445

Lys

<210> SEQ ID NO 32
<211> LENGTH: 226
<212> TYPE: PRT
<213> ORGANISM: Artificial Sequence
<220> FEATURE:
<223> OTHER INFORMATION: Sequence from mAbs

<400> SEQUENCE: 32

Val Ser Gly Ala Cys Ala Asp Ile Val Met Thr Gln Ser Pro Ser Ser
1               5                   10                  15

Leu Ala Met Ser Val Gly Gln Lys Val Thr Met Ser Cys Lys Ser Ser
                20                  25                  30

Gln Ser Leu Leu Asn Ser Asp Thr Gln Lys Asn Phe Leu Ala Trp Tyr
            35                  40                  45

Gln Gln Lys Pro Gly Gln Ser Pro Lys Ile Leu Val Tyr Phe Ala Ser
        50                  55                  60

Thr Lys Glu Ser Gly Val Pro Asp Arg Phe Ile Gly Ser Gly Ser Gly
65                  70                  75                  80

Thr Asp Phe Thr Leu Thr Ile Thr Ser Val Gln Ala Glu Asp Leu Ala
                85                  90                  95

Asp Tyr Phe Cys Gln Gln Tyr Tyr Ser Ile Pro Leu Thr Phe Gly Ala
                100                 105                 110

Gly Thr Lys Leu Glu Leu Lys Arg Ala Asp Ala Ala Pro Thr Val Ser
            115                 120                 125
```

```
Ile Phe Pro Pro Ser Ser Glu Gln Leu Thr Ser Gly Gly Ala Ser Val
130                 135                 140

Val Cys Phe Leu Asn Asn Phe Tyr Pro Lys Asp Ile Asn Val Lys Trp
145                 150                 155                 160

Lys Ile Asp Gly Ser Glu Arg Gln Asn Gly Val Leu Asn Ser Trp Thr
                165                 170                 175

Asp Gln Asp Ser Lys Asp Ser Thr Tyr Ser Met Ser Ser Thr Leu Thr
                180                 185                 190

Leu Thr Lys Asp Glu Tyr Glu Arg His Asn Ser Tyr Thr Cys Glu Ala
            195                 200                 205

Thr His Lys Thr Ser Thr Ser Pro Ile Val Lys Ser Phe Asn Arg Asn
210                 215                 220

Glu Cys
225
```

<210> SEQ ID NO 33
<211> LENGTH: 469
<212> TYPE: PRT
<213> ORGANISM: Artificial Sequence
<220> FEATURE:
<223> OTHER INFORMATION: Sequence from mAbs

<400> SEQUENCE: 33

```
Arg Met Lys Val Leu Ser Leu Leu Tyr Leu Leu Thr Ala Ile Pro Gly
1               5                   10                  15

Phe Leu Ser Asp Val Gln Leu Gln Glu Ser Gly Pro Gly Leu Val Lys
                20                  25                  30

Pro Ser Gln Ser Leu Ser Leu Thr Cys Ser Val Thr Gly Tyr Ser Ile
            35                  40                  45

Thr Ser Asp Tyr Tyr Trp Asn Trp Ile Arg Gln Phe Pro Gly Asn Lys
50                  55                  60

Leu Glu Trp Met Ala Tyr Ile Gly Tyr Asp Gly Ser Lys Asn Tyr Asn
65                  70                  75                  80

Pro Ser Leu Lys Asn Arg Ile Ser Ile Thr Arg Asp Thr Ser Lys Asn
                85                  90                  95

Gln Phe Phe Leu Lys Leu Asn Ser Val Thr Thr Asp Asp Thr Ala Thr
            100                 105                 110

Tyr Tyr Cys Thr Arg Asp Arg Ala Asn Trp Asp Asp Tyr Phe Asp Tyr
        115                 120                 125

Trp Gly Gln Gly Thr Thr Leu Thr Val Ser Ser Ala Lys Thr Thr Ala
130                 135                 140

Pro Ser Val Tyr Pro Leu Ala Pro Val Cys Gly Asp Thr Thr Gly Ser
145                 150                 155                 160

Ser Val Thr Leu Gly Cys Leu Val Lys Gly Tyr Phe Pro Glu Pro Val
                165                 170                 175

Thr Leu Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Thr Ser Ser Thr Trp Pro Ser Gln Ser Ile Thr Cys Asn Val Ala
210                 215                 220

His Pro Ala Ser Ser Thr Lys Val Asp Lys Lys Ile Glu Pro Arg Gly
225                 230                 235                 240

Pro Thr Ile Lys Pro Cys Pro Pro Cys Lys Cys Pro Ala Pro Asn Leu
                245                 250                 255
```

```
Leu Gly Gly Pro Ser Val Phe Ile Phe Pro Pro Lys Ile Lys Asp Val
            260                 265                 270

Leu Met Ile Ser Leu Ser Pro Ile Val Thr Cys Val Val Val Asp Val
        275                 280                 285

Ser Glu Asp Asp Pro Asp Val Gln Ile Ser Trp Phe Val Asn Asn Val
290                 295                 300

Glu Val His Thr Ala Gln Thr Gln Thr His Arg Glu Asp Tyr Asn Ser
305                 310                 315                 320

Thr Leu Arg Val Val Ser Ala Leu Pro Ile Gln His Gln Asp Trp Met
                325                 330                 335

Ser Gly Lys Glu Phe Lys Cys Lys Val Asn Asn Lys Asp Leu Pro Ala
            340                 345                 350

Pro Ile Glu Arg Thr Ile Ser Lys Pro Lys Gly Ser Val Arg Ala Pro
        355                 360                 365

Gln Val Tyr Val Leu Pro Pro Glu Glu Glu Met Thr Lys Lys Gln
370                 375                 380

Val Thr Leu Thr Cys Met Val Thr Asp Phe Met Pro Glu Asp Ile Tyr
385                 390                 395                 400

Val Glu Trp Thr Asn Asn Gly Lys Thr Glu Leu Asn Tyr Lys Asn Thr
                405                 410                 415

Glu Pro Val Leu Asp Ser Asp Gly Ser Tyr Phe Met Tyr Ser Lys Leu
            420                 425                 430

Arg Val Glu Lys Lys Asn Trp Val Glu Arg Asn Ser Tyr Ser Cys Ser
        435                 440                 445

Val Val His Glu Gly Leu His Asn His His Thr Thr Lys Ser Phe Ser
    450                 455                 460

Arg Thr Pro Gly Lys
465

<210> SEQ ID NO 34
<211> LENGTH: 233
<212> TYPE: PRT
<213> ORGANISM: Artificial Sequence
<220> FEATURE:
<223> OTHER INFORMATION: Sequence from mAbs

<400> SEQUENCE: 34

Val Leu Met Leu Leu Leu Leu Trp Val Ser Gly Thr Cys Gly Asp Ile
1               5                   10                  15

Val Met Ser Gln Ser Pro Ser Ser Leu Ala Val Ser Val Gly Glu Lys
            20                  25                  30

Val Thr Met Ser Cys Lys Ser Ser Gln Ser Leu Leu Asn Ser Arg Asn
        35                  40                  45

Gln Lys Asn His Leu Ala Trp Tyr Gln Gln Lys Pro Gly Gln Ser Pro
    50                  55                  60

Lys Leu Leu Ile Tyr Trp Ala Ser Thr Arg Glu Ser Gly Val Pro Asp
65                  70                  75                  80

Arg Phe Ser Gly Asp Gly Ser Gly Thr Asp Phe Thr Leu Thr Ile Ser
                85                  90                  95

Ser Val Lys Ala Glu Asp Leu Ala Val Tyr Tyr Cys Gln Gln Tyr Tyr
            100                 105                 110

Thr Tyr Arg Thr Phe Gly Gly Gly Thr Lys Leu Glu Ile Lys Arg Ala
        115                 120                 125

Asp Ala Ala Pro Thr Val Ser Ile Phe Pro Pro Ser Ser Glu Gln Leu
    130                 135                 140
```

Thr Ser Gly Gly Ala Ser Val Val Cys Phe Leu Asn Asn Phe Tyr Pro
145                 150                 155                 160

Lys Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
            180                 185                 190

Ser Met Ser Ser Thr Leu Thr Leu Thr Lys Asp Glu Tyr Glu Arg His
        195                 200                 205

Asn Ser Tyr Thr Cys Glu Ala Thr His Lys Thr Ser Thr Ser Pro Ile
    210                 215                 220

Val Lys Ser Phe Asn Arg Asn Glu Cys
225                 230

<210> SEQ ID NO 35
<211> LENGTH: 731
<212> TYPE: PRT
<213> ORGANISM: Artificial Sequence
<220> FEATURE:
<223> OTHER INFORMATION: mAb 10A9 sequence

<400> SEQUENCE: 35

Met Glu Thr Asp Thr Leu Leu Leu Trp Val Leu Leu Leu Trp Val Pro
1               5                   10                  15

Gly Ser Thr Gly Gln Ile Gln Leu Gln Gln Ser Gly Pro Glu Leu Val
            20                  25                  30

Lys Pro Gly Ala Pro Val Lys Ile Ser Cys Lys Ala Ser Gly Tyr Thr
        35                  40                  45

Phe Thr Asp Tyr Tyr Ile His Trp Val Asn Gln Arg Pro Gly Gln Gly
    50                  55                  60

Leu Glu Trp Ile Gly Tyr Ile Tyr Pro Gly Asn Gly His Thr Val Tyr
65                  70                  75                  80

Asn Gln Lys Phe Lys Val Arg Ala Thr Leu Thr Ala Asp Asn Pro Ser
                85                  90                  95

Ser Thr Ala Tyr Leu Gln Leu Asn Ser Leu Thr Ser Glu Asp Ser Gly
            100                 105                 110

Val Tyr Phe Cys Ala Tyr Asp Leu Phe Asn Tyr Trp Gly Gln Gly Thr
        115                 120                 125

Leu Val Thr Val Ser Ala Ala Lys Thr Thr Ala Pro Ser Val Tyr Pro
130                 135                 140

Leu Ala Pro Val Cys Gly Asp Thr Thr Gly Ser Ser Val Thr Leu Gly
145                 150                 155                 160

Cys Leu Val Lys Gly Tyr Phe Pro Glu Pro Val Thr Leu Thr Trp Asn
                165                 170                 175

Ser Gly Ser Leu Ser Ser Gly Val His Thr Phe Pro Ala Val Leu Gln
            180                 185                 190

Ser Asp Leu Tyr Thr Leu Ser Ser Ser Val Thr Val Thr Ser Ser Thr
        195                 200                 205

Trp Pro Ser Gln Ser Ile Thr Cys Asn Val Ala His Pro Ala Ser Ser
    210                 215                 220

Thr Lys Val Asp Lys Lys Ile Glu Pro Arg Gly Pro Thr Ile Lys Pro
225                 230                 235                 240

Cys Pro Pro Cys Lys Cys Pro Ala Pro Asn Leu Leu Gly Gly Pro Ser
                245                 250                 255

Val Phe Ile Phe Pro Pro Lys Ile Lys Asp Val Leu Met Ile Ser Leu
            260                 265                 270

-continued

Ser Pro Ile Val Thr Cys Val Val Asp Val Ser Glu Asp Pro
        275                 280                 285

Asp Val Gln Ile Ser Trp Phe Val Asn Val Glu Val His Thr Ala
    290                 295                 300

Gln Thr Gln Thr His Arg Glu Asp Tyr Asn Ser Thr Leu Arg Val Val
305                 310                 315                 320

Ser Ala Leu Pro Ile Gln His Gln Asp Trp Met Ser Gly Lys Glu Phe
                325                 330                 335

Lys Cys Lys Val Asn Asn Lys Asp Leu Pro Ala Pro Ile Glu Arg Thr
                340                 345                 350

Ile Ser Lys Pro Lys Gly Ser Val Arg Ala Pro Gln Val Tyr Val Leu
            355                 360                 365

Pro Pro Pro Glu Glu Glu Met Thr Lys Lys Gln Val Thr Leu Thr Cys
    370                 375                 380

Met Val Thr Asp Phe Met Pro Glu Asp Ile Tyr Val Glu Trp Thr Asn
385                 390                 395                 400

Asn Gly Lys Thr Glu Leu Asn Tyr Lys Asn Thr Glu Pro Val Leu Asp
                405                 410                 415

Ser Asp Gly Ser Tyr Phe Met Tyr Ser Lys Leu Arg Val Glu Lys Lys
            420                 425                 430

Asn Trp Val Glu Arg Asn Ser Tyr Ser Cys Ser Val Val His Glu Gly
        435                 440                 445

Leu His Asn His His Thr Thr Lys Ser Phe Ser Arg Thr Pro Gly Arg
    450                 455                 460

Lys Arg Arg Ala Pro Val Lys Gln Thr Leu Asn Phe Asp Leu Leu Lys
465                 470                 475                 480

Leu Ala Gly Asp Val Glu Ser Asn Pro Gly Pro Met Glu Thr Asp Thr
                485                 490                 495

Leu Leu Leu Trp Val Leu Leu Leu Trp Val Pro Gly Ser Thr Gly Asp
            500                 505                 510

Ile Val Met Thr Gln Ser Pro Ser Ser Leu Ala Met Ser Val Gly Gln
        515                 520                 525

Lys Val Thr Met Ser Cys Lys Ser Ser Gln Ser Leu Leu Asn Ser Asp
530                 535                 540

Thr Gln Lys Asn Phe Leu Ala Trp Tyr Gln Gln Lys Pro Gly Gln Ser
545                 550                 555                 560

Pro Lys Ile Leu Val Tyr Phe Ala Ser Thr Lys Glu Ser Gly Val Pro
                565                 570                 575

Asp Arg Phe Ile Gly Ser Gly Ser Gly Thr Asp Phe Thr Leu Thr Ile
            580                 585                 590

Thr Ser Val Gln Ala Glu Asp Leu Ala Asp Tyr Phe Cys Gln Gln Tyr
        595                 600                 605

Tyr Ser Ile Pro Leu Thr Phe Gly Ala Gly Thr Lys Leu Glu Leu Lys
    610                 615                 620

Arg Ala Asp Ala Ala Pro Thr Val Ser Ile Phe Pro Pro Ser Ser Glu
625                 630                 635                 640

Gln Leu Thr Ser Gly Gly Ala Ser Val Val Cys Phe Leu Asn Asn Phe
                645                 650                 655

Tyr Pro Lys Asp Ile Asn Val Lys Trp Lys Ile Asp Gly Ser Glu Arg
            660                 665                 670

Gln Asn Gly Val Leu Asn Ser Trp Thr Asp Gln Asp Ser Lys Asp Ser
        675                 680                 685

```
Thr Tyr Ser Met Ser Ser Thr Leu Thr Leu Thr Lys Asp Glu Tyr Glu
            690                 695                 700
Arg His Asn Ser Tyr Thr Cys Glu Ala Thr His Lys Thr Ser Thr Ser
705                 710                 715                 720
Pro Ile Val Lys Ser Phe Asn Arg Asn Glu Cys
                725                 730
```

<210> SEQ ID NO 36
<211> LENGTH: 736
<212> TYPE: PRT
<213> ORGANISM: Artificial Sequence
<220> FEATURE:
<223> OTHER INFORMATION: mAb 11H12 sequence

<400> SEQUENCE: 36

```
Met Glu Thr Asp Thr Leu Leu Leu Trp Val Leu Leu Leu Trp Val Pro
1               5                   10                  15
Gly Ser Thr Gly Asp Val Gln Leu Gln Glu Ser Gly Pro Gly Leu Val
            20                  25                  30
Lys Pro Ser Gln Ser Leu Ser Leu Thr Cys Ser Val Thr Gly Tyr Ser
        35                  40                  45
Ile Thr Ser Asp Tyr Tyr Trp Asn Trp Ile Arg Gln Phe Pro Gly Asn
    50                  55                  60
Lys Leu Glu Trp Met Ala Tyr Ile Gly Tyr Asp Gly Thr Lys Asn Tyr
65                  70                  75                  80
Asn Pro Ser Leu Lys Asn Arg Ile Ser Ile Thr Arg Asp Thr Ser Lys
                85                  90                  95
Asn Gln Phe Phe Leu Lys Leu Asn Ser Val Thr Thr Asp Asp Thr Ala
            100                 105                 110
Thr Tyr Tyr Cys Thr Arg Asp Arg Ala Asn Trp Asp Asp Tyr Phe Asp
        115                 120                 125
Tyr Trp Gly Gln Gly Thr Thr Leu Thr Val Ser Ser Ala Lys Thr Thr
    130                 135                 140
Ala Pro Ser Val Tyr Pro Leu Ala Pro Val Cys Gly Asp Thr Thr Gly
145                 150                 155                 160
Ser Ser Val Thr Leu Gly Cys Leu Val Lys Gly Tyr Phe Pro Glu Pro
                165                 170                 175
Val Thr Leu Thr Trp Asn Ser Gly Ser Leu Ser Ser Gly Val His Thr
            180                 185                 190
Phe Pro Ala Val Leu Gln Ser Asp Leu Tyr Thr Leu Ser Ser Ser Val
        195                 200                 205
Thr Val Thr Ser Ser Thr Trp Pro Ser Gln Ser Ile Thr Cys Asn Val
    210                 215                 220
Ala His Pro Ala Ser Ser Thr Lys Val Asp Lys Lys Ile Glu Pro Arg
225                 230                 235                 240
Gly Pro Thr Ile Lys Pro Cys Pro Pro Cys Lys Cys Pro Ala Pro Asn
                245                 250                 255
Leu Leu Gly Gly Pro Ser Val Phe Ile Phe Pro Pro Lys Ile Lys Asp
            260                 265                 270
Val Leu Met Ile Ser Leu Ser Pro Ile Val Thr Cys Val Val Val Asp
        275                 280                 285
Val Ser Glu Asp Asp Pro Asp Val Gln Ile Ser Trp Phe Val Asn Asn
    290                 295                 300
Val Glu Val His Thr Ala Gln Thr Gln Thr His Arg Glu Asp Tyr Asn
305                 310                 315                 320
```

-continued

```
Ser Thr Leu Arg Val Ser Ala Leu Pro Ile Gln His Gln Asp Trp
            325                 330                 335

Met Ser Gly Lys Glu Phe Lys Cys Lys Val Asn Asn Lys Asp Leu Pro
        340                 345                 350

Ala Pro Ile Glu Arg Thr Ile Ser Lys Pro Lys Gly Ser Val Arg Ala
        355                 360                 365

Pro Gln Val Tyr Val Leu Pro Pro Glu Glu Met Thr Lys Lys
    370                 375                 380

Gln Val Thr Leu Thr Cys Met Val Thr Asp Phe Met Pro Glu Asp Ile
385                 390                 395                 400

Tyr Val Glu Trp Thr Asn Asn Gly Lys Thr Glu Leu Asn Tyr Lys Asn
                405                 410                 415

Thr Glu Pro Val Leu Asp Ser Asp Gly Ser Tyr Phe Met Tyr Ser Lys
            420                 425                 430

Leu Arg Val Glu Lys Lys Asn Trp Val Glu Arg Asn Ser Tyr Ser Cys
        435                 440                 445

Ser Val Val His Glu Gly Leu His Asn His His Thr Thr Lys Ser Phe
    450                 455                 460

Ser Arg Thr Pro Gly Arg Lys Arg Arg Ala Pro Val Lys Gln Thr Leu
465                 470                 475                 480

Asn Phe Asp Leu Leu Lys Leu Ala Gly Asp Val Glu Ser Asn Pro Gly
                485                 490                 495

Pro Met Glu Thr Asp Thr Leu Leu Leu Trp Val Leu Leu Leu Trp Val
            500                 505                 510

Pro Gly Ser Thr Gly Asp Ile Val Met Ser Gln Ser Pro Ser Ser Leu
        515                 520                 525

Ala Val Ser Val Gly Glu Lys Val Thr Met Ser Cys Lys Ser Ser Gln
    530                 535                 540

Ser Leu Leu Asn Ser Arg Asn Gln Lys Asn His Leu Ala Trp Tyr Gln
545                 550                 555                 560

Gln Lys Pro Gly Gln Ser Pro Lys Leu Leu Ile Tyr Trp Ala Ser Thr
                565                 570                 575

Arg Glu Ser Gly Val Pro Asp Arg Phe Thr Gly Asp Gly Ser Gly Thr
            580                 585                 590

Asp Phe Thr Leu Thr Ile Ser Ser Val Lys Ala Glu Asp Leu Ala Val
        595                 600                 605

Tyr Tyr Cys Gln Gln Tyr Tyr Thr Tyr Arg Thr Phe Gly Gly Gly Thr
    610                 615                 620

Lys Leu Glu Ile Lys Arg Ala Asp Ala Ala Pro Thr Val Ser Ile Phe
625                 630                 635                 640

Pro Pro Ser Ser Glu Gln Leu Thr Ser Gly Gly Ala Ser Val Val Cys
                645                 650                 655

Phe Leu Asn Asn Phe Tyr Pro Lys Asp Ile Asn Val Lys Trp Lys Ile
            660                 665                 670

Asp Gly Ser Glu Arg Gln Asn Gly Val Leu Asn Ser Trp Thr Asp Gln
        675                 680                 685

Asp Ser Lys Asp Ser Thr Tyr Ser Met Ser Ser Thr Leu Thr Leu Thr
    690                 695                 700

Lys Asp Glu Tyr Glu Arg His Asn Ser Tyr Thr Cys Glu Ala Thr His
705                 710                 715                 720

Lys Thr Ser Thr Ser Pro Ile Val Lys Ser Phe Asn Arg Asn Glu Cys
                725                 730                 735
```